United States Patent
Brünn

(10) Patent No.: US 11,976,110 B2
(45) Date of Patent: *May 7, 2024

(54) MEANS AND METHODS FOR THE DETERMINATION OF THE BIOLOGICAL ACTIVITY OF NEUROTOXIN POLYPEPTIDES IN CELLS

(71) Applicant: MERZ PHARMA GmbH & CO. KGaA, Frankfurt am Main (DE)

(72) Inventor: Cornelia Brünn, Frankfurt (DE)

(73) Assignee: MERZ PHARMA GmbH & CO. KGaA, Frankfurt (DE)

( * ) Notice: Subject to any disclaimer, the term of this patent is extended or adjusted under 35 U.S.C. 154(b) by 420 days.

This patent is subject to a terminal disclaimer.

(21) Appl. No.: 14/901,123

(22) PCT Filed: Jun. 26, 2014

(86) PCT No.: PCT/EP2014/063531
§ 371 (c)(1),
(2) Date: Dec. 28, 2015

(87) PCT Pub. No.: WO2014/207109
PCT Pub. Date: Dec. 31, 2014

(65) Prior Publication Data
US 2016/0202245 A1   Jul. 14, 2016

(30) Foreign Application Priority Data
Jun. 28, 2013 (EP) .................... 13174176

(51) Int. Cl.
*G01N 33/53* (2006.01)
*C07K 16/18* (2006.01)
*G01N 21/64* (2006.01)
*G01N 33/50* (2006.01)

(52) U.S. Cl.
CPC ......... *C07K 16/18* (2013.01); *G01N 21/6428* (2013.01); *G01N 33/5014* (2013.01); *G01N 33/5058* (2013.01); *G01N 33/5073* (2013.01); *C07K 2317/34* (2013.01); *G01N 2021/6441* (2013.01); *G01N 2333/33* (2013.01); *G01N 2333/952* (2013.01)

(58) Field of Classification Search
CPC ............... C07K 16/18; C07K 2317/34; G01N 21/6428; G01N 33/5014; G01N 33/5058; G01N 33/5073; G01N 2021/6441; G01N 2333/33; G01N 2333/952
See application file for complete search history.

(56) References Cited

U.S. PATENT DOCUMENTS

| | | |
|---|---|---|
| 7,229,605 B2 | 6/2007 | Holland et al. |
| 8,198,034 B2 * | 6/2012 | Fernandez-Salas ........................ C07K 16/1282 435/7.1 |
| 8,420,352 B2 | 4/2013 | Oyler |
| 8,609,413 B2 | 12/2013 | Suter |
| 8,778,623 B2 | 7/2014 | Johnson |
| 9,102,901 B2 | 8/2015 | Wang |
| 9,217,172 B2 | 12/2015 | Johnson |

(Continued)

FOREIGN PATENT DOCUMENTS

| | | |
|---|---|---|
| EP | 1597584 | 2/2004 |
| EP | 2015065 | 4/2006 |

(Continued)

OTHER PUBLICATIONS

Sigma catalog((2002; retrieved from https://www.sigmaaldrich.com/content/dam/sigma-aldrich/docs/Sigma/Datasheet/5/s9684dat.pdf).*
Meng et al. (Analytical Biochemistry 345 (2005) 227-236).*
E. A. Padlan, Adv Prot Chem 49:57-133; 1996.*
Corada et al., Blood, 2001; 97:1679-84.*
Research and Diagnostic Antibodies Catalog (2005; retrieved from http://www.rdabs.com/files/Antibodies/Monoclonal%20Abs.pdf.*

(Continued)

*Primary Examiner* — Carmencita M Belei
(74) *Attorney, Agent, or Firm* — HUESCHEN AND SAGE

(57) ABSTRACT

The present invention pertains to a method for directly determining the biological activity of a Neurotoxin polypeptide in cells, comprising the steps of: a) incubating cells susceptible to Neurotoxin intoxication with a Neurotoxin polypeptide for a time and under conditions which allow for the Neurotoxin polypeptide to exert its biological activity; b) fixing the cells and, optionally, permeabilizing the cells with a detergent; c) contacting the cells with at least a first capture antibody specifically binding to the non-cleaved and Neurotoxin-cleaved substrate and with at least a second capture antibody specifically binding to the cleavage site of the Neurotoxin-cleaved substrate, under conditions which allow for binding of said capture antibodies to said substrates; d) contacting the cells with at least a first detection antibody specifically binding to the first capture antibody, under conditions which allow for binding of said first detection antibody to said first capture antibody, thus forming first detection complexes, and at least a second detection antibody specifically binding to the second capture antibody, under conditions which allow for binding of said second detection antibody to said second capture antibody, thus forming second detection complexes; e) determining the amount of the first and second detection complexes of step d), and f) calculating the amount of substrate cleaved by said Neurotoxin polypeptide in said cells by means of the second detection complexes, thereby determining the biological activity of said Neurotoxin polypeptide in said cells. The invention further provides for a kit for carrying out the method of the invention.

12 Claims, 3 Drawing Sheets

Specification includes a Sequence Listing.

(56) References Cited

U.S. PATENT DOCUMENTS

| | | |
|---|---|---|
| 9,579,362 B2 | 2/2017 | Nevalaita |
| 10,725,025 B2 | 7/2020 | Jatzke |
| 2003/0032891 A1 | 2/2003 | Jenkins |
| 2006/0099672 A1 | 5/2006 | Dolly |
| 2008/0032931 A1 | 2/2008 | Steward |
| 2010/0167286 A1 | 7/2010 | Reijo Pera |
| 2010/0216181 A1 | 8/2010 | Daigh |
| 2010/0233802 A1 | 9/2010 | Zhu |
| 2010/0279403 A1 | 11/2010 | Rajesh |
| 2011/0008397 A1 | 1/2011 | Cohen |
| 2011/0046092 A1 | 2/2011 | Suter |
| 2011/0053244 A1 | 3/2011 | Oyler |
| 2012/0276063 A1 | 11/2012 | Meyer |
| 2012/0282647 A1 | 11/2012 | Mander |
| 2014/0248644 A1 | 9/2014 | Wang |
| 2015/0044709 A1 | 2/2015 | Eisele |
| 2016/0289731 A1 | 10/2016 | Eisele |
| 2017/0059558 A1 | 3/2017 | Eisele |
| 2018/0045733 A1 | 2/2018 | Eisele |
| 2018/0238861 A1 | 8/2018 | Jatzke |
| 2019/0023771 A1 | 1/2019 | Bruenn |

FOREIGN PATENT DOCUMENTS

| | | | |
|---|---|---|---|
| EP | 1926744 | 6/2008 | |
| GB | 2398636 | 8/2004 | |
| GB | 2416849 | 2/2006 | |
| WO | WO 9533850 | 12/1995 | |
| WO | WO2004031773 | 4/2004 | |
| WO | WO2005007185 | 1/2005 | |
| WO | WO 2005/076785 | 8/2005 | |
| WO | WO2006020208 | 2/2006 | |
| WO | WO2009114748 | 9/2009 | |
| WO | WO2010099539 | 9/2010 | |
| WO | WO2010105234 | 9/2010 | |
| WO | WO2011022438 | * 2/2011 | ............ G01N 33/53 |
| WO | WO2011025852 | 3/2011 | |
| WO | WO2011047265 | 4/2011 | |
| WO | WO2011056971 | 5/2011 | |
| WO | WO 2012123370 | 9/2012 | |
| WO | WO2012135621 | 10/2012 | |
| WO | WO2014079878 | 5/2014 | |

OTHER PUBLICATIONS

Sigma catalog 2006 (2006; retrieved from web, Jun. 19, 2020).*

Stahl (Journal of Biomolecular Screening 2007, 12(3) pp. 370-377.*

Armbruster, David, A., et al., "Limit of Blank, Limit of Detection and Limit of Quantitation", Clin. Biochem. Rev., vol. 29, Suppl (i), Aug. 2008, pp. s49-s52.

Arnon, Stephen, S., et al., "Botulinum toxin as a biological weapon, medical and public health management", JAMA, vol. 285, No. 8, Feb. 2001, pp. 1059-1070.

Baldwin, Michael, R., et al., "Association of Botulinum neurotoxin serotypes A and B with synaptic vesicle protein complexes", Biochemistry, 46, 2007, pp. 3200-3210.

Cai, Shuowei, et al., "Botulism diagnostics: from clinical symptoms to in vitro assays", Critical Reviews in Microbiology, 33, 2007, pp. 109-125.

Couesnon, Aurelie, et al., "Expression of botulinum neurotoxins A and E, and associated non-toxin genes, during the transition phase and stability at high temperature: analysis by quantitative reverse transcription-PCR", Microbiology, 152, 20-06, pp. 759-770.

Dressler, Dirk, et al., "Mouse diaphragm assay for detection of antibodies against botulinum toxin type B", Movement Disorders, vol. 20, No. 12, 2005, pp. 1617-1619.

Fernandez-Salas, Ester, et al., "Botulinum neurotoxin serotype a specific cell-based potency assay to replace the mouse bioassay", PLoS One, vol. 7, Iss. 11, Nov. 2012, e49516, pp. 1-13.

Fischer, Audrey, et al., "Single molecule detection of intermediates during botulinum neurotoxin translocation across membranes", PNAS, vol. 104, No. 25, Jun. 19, 2007, pp. 10447-10452.

Gee, Kyle, R., et al., "Fluorogenic substrates based on fluorinated umbelliferones for continuous assays of phosphatases and $\beta$-galactosidases", Analytical Biochemistry, vol. 273, Iss. 1, Aug. 1999, pp. 41-48.

Hemmerlein, Barnhard, et al., "Overexpression of Eag1 potassium channels in clinical tumours", Molecular Cancer, 5:41, 2006, pp. 1-13.

Jost, Wolfgang, H., et al., "Botulinum neurotoxin type A free of complexing proteins (Xeomin) in focal dystonia", Drugs, 67(5), 2007, pp. 669-683.

Keller, J.E., "Recovery from botulinum neurotoxin poisoning in vivo", Neuroscience, 139, 2006, pp. 629-637.

Krieglstein, Kerstin, et al., "Arrangement of disulfide bridges and positions of sulfhydryl groups in tetanus toxin", Eur. J. Biochem., 188, 1990, pp. 39-45.

Krieglstein, Kerstin, G., et al., "Covalent structure of botulinum neurotoxin type A: location of sulfhydryl groups, and disulfide bridges and identification of C-termini of light and heavy chains", Journal of Protein Chemistry, vol. 13, No. 1, 1994, pp. 49-57.

Krieglstein, Kerstin, G., et al., "Limited proteolysis of tetanus toxin", Eur. J. Biochem, 202, 1991, pp. 41-51.

Needleman, Saul, B., et al., "A general method applicable to the search for similarities in the amino acid sequence of two proteins", J. Mol. Biol., 48, 1970, pp. 443-453.

Pearce, L. Bruce, et al., "Measurement of botulinum toxin activity: evaluation of the lethality assay", Toxicology and Applied Pharmacology, 128, 1994, pp. 69-77.

Pellet, Sabine, et al., "Sensitive and quantitative detection of botulinum neurotoxin in neurons derived from mouse embryonic stem cells", Biochem. Biophys. Res. Commun., 404(1), Jan. 7, 2011, pp. 388-392.

Silberstein, Stephen, "Botulinum neurotoxins: origins and basic mechanisms of action", Pain Practice, vol. 4, Iss. 1S, 2004, pp. S19-S26.

Staughan, Donald, W., "Progress in applying the three Rs to the potency testing of botulinum toxin type A", ATLA, 34, 2006, pp. 305-313.

Tuuminen, Tamara, et al., "3-p-hydroxyphenylpropionic acid—a sensitive fluorogenic substrate for automated fluorometric enzyme immunoassays", Journal of Immunoassay, 12:1, 1991, pp. 29-46.

Whitemarsh, Regina, C.M., "Novel application of human neurons derived from induced pluripotent stem cells for highly sensitive botulinum neurotoxin detection", Toxicological Sciences, 126(2), 2012, pp. 426-435.

Yu, Junying, et al., "Human induced pluripotent stem cells free of vector and transgene sequences", Science, 324(5928), May 8, 2009, pp. 797-801.

Funakoshi Product Catalog, "Kit for semiquantifying two proteins on cultured cells". Published Mar. 2, 2009.

Jamieson, et al. "Development and validation of cell-based Elisa for the quantification of trastuzumab in human plasma", Journal of Immunological Methods, 345:106-111, 2009.

Nuss, et al. "Botulinum Neurotoxin Serotype A Cleavage-Sensitive Antibodies", Journal of Biomolecular Screening, 15(1):42-52, 2-10.

R&D Systems Product Catalog, "Cell-Based Elisa", published 2007.

Rheaume, et al. "A Highly Specific Monoclonal Antibody for Botulinum Neurotoxin Type A-Cleaved Snap25" Toxins, 7:2354-2370, 2015.

Yang, et al. "Development of a quantitative cell-based Elisa, for a humanized anti-IL-2/IL-15 receptor $\beta$ antibody (HuMik$\beta$1), and correlation with functional activity using an antigen-transfected murine cell line", Journal of Immunological Methods, 311:71-80, 2006.

Berntsson, Ronnie P.A. et al, Structure of dual receptor binding to botulinum neurotoxin B, Nature Communication, 2013, vol. 4(2058), pp. 1-13.

Boroff, Daniel., A., et al., Journal of Bacteriology, No. 1956, vol. 92, No. 5, p. 1580-1581, "Statistical analysis of a rapid in vivo method for the titration of the toxin of Clostridium botulinum".

Chang et al., Naunyn-Schmiedeberg's Arch. Pharmacol. vol. 282, p. 129-142 (1974).

(56) References Cited

OTHER PUBLICATIONS

Ekong, Theresa, A., et al., Microbiology, 1997, vol. 143, pp. 3337-3347, "Recombinanat Snap-25 is an effective substrate for Clostridium botulinum type A toxin endopeptidase activity in vitro".
Ellies, M., (English translation) Laryngo-Rhino-Otol, 2003, vol. 82, pp. 713-714, "Tierexperimentelle und klinische untersuchungen zur sekretionshemmung der kopfspeicheldrüsen durch botulinum toxin A".
Ellies, M., Laryngo-Rhino-otol, 2003, vol. 82, pp. 713-714, "Tierexperimentelle und klinische untersuchungen zur sekretionshemmung der kopfspeicheldrüsen durch botulinum toxin A".
Evans, E.R., et al., Journal of Applied Microbiology, 2009, vol. 107. pp. 1384-1391, "An assay for botulinum toxin types A, B and F that requires both functional binding and catalytic activities within the neurotoxin".
Fan, Frank, et al., Assay and Drug Development Technologies, vol. 5, No. 1, 2007, pp. 127-136, "Bioluminescent assays for high-troughput screening".
Göschel et al., Exp. Neurol., vol. 147, p. 1, 1997.
Gossen, Manfred, et al., Proc. Natl. Acad. Sci. USA, Jun. 1992, vol. 89, pp. 6547-6551, "Tight control of gene expression in mammalian cells by tetracycline-responsive promoters".
Habermann, E., Naunyn-Schmiedeberg's Arch. Pharmacol., 1974, vol. 281, pp. 47-56, "I-labeled neurotoxin from Clostridium botulinum A: preparation, binding to synaptosomes and ascent to the spinal cord".
Hester, Mark E. et al., Molecular Therapy, vol. 19(10) pp. 1905-1912, Oct. 2011.
Hughes, R., et al., J. Physiol. 1962, vol. 160, pp. 221-233, "Influence of nerve-ending activity and of drugs on the rate of paralysis of rat diaphragm preparatioins by CL. botulinum type A toxin".
International Preliminary Report on Patentability for PCT/EP2013/074276 dated Jun. 4, 2015.
International Search Report With Written Opinion for PCT/EP2010/006967 dated Jan. 24, 2011.
International Search Report and Written Opinion for PCT/US2012/057825 dated Nov. 8, 2012.
International Search Report for PCT/EP2013/074276 dated Feb. 13, 2014.
Jacky, Birgitte P.S. et al, PLOS Pathogens, May 2013, vol. 9(5)e1003369, pp. 1-17, Identification of fibroblast growth factor receptor 3 (FGFR3) as a protein receptor for botulinum neurotoxin serotype A (BoNT/A).
James et al., Am. J. Physiol. Gastrointest. Liver Physiol. vol. 285, p. G291-G297 (2003).
Jones, R.G.A, et al., "Development of improved Snap25 endopeptidase immuno-assays for botulinum type A and E toxins", Journal of Immunological Methods 329, 2008, pp. 92-101.
Karumbayaram, et al., Stem Cells, vol. 27, No. 4, p. 806-811, 2009.
Keller J., et al., Biochemistry, vol. 43, No. 2, p. 526-532, Jan. 20, 2004.
Keller, James E., et al., FEBS Letters 456, 1999, pp. 137-142, "Persistence of botulinum neurotoxin action in cultured spinal cord cells".
Kiris, et al., Stem Cell Res., vol. 6, No. 3, p. 195-205, May 2011.
Kondo, Hisashi, et al., Japan, J. Med. Sci. Biol., 1984, vol. 37, pp. 131-135, "Titration of botulinum toxins for lethal toxicity by intravenous injection into mice".
Lamanna, Carl, et al., Infection and Immunity, Apr. 1970, vol. 1, No. 4, pp. 423-424 "Dependence of time to death on molecular size of botulinum toxin".
Malizio, Carl J., et al., Methods in Molecular Biology, 2000, vol. 145: Bactrial Toxins: methods and Protocols, pp. 27-39, "Purification of Clostridium botulinum type A neurotoxin".

McNutt, Patrick, et al., Biochemical and Biophysical Research Communications, 2011, vol. 405, pp. 85-90.
Miraglia, Loren, J., et al., Combinatorial Chemistry & High Throughtput Screening, 2011, vol. 14, pp. 648-657 "Seeing the light: luminescent reporter gene assays".
Monnier, G., et al., (English Translation) Readapt. Med. Phys. 2003, vol. 46, pp. 338-345 "Hypersialorrhée, hypersudation et toxine botulique sialorrhea, hyperhidrosis and botulinum toxin".
Monnier, G., et al., Readapt. Med. Phys. 2003, vol. 46, pp. 338-345 "Hypersialorrhée, hypersudation et toxine botulique sialorrhea, hyperhidrosis and botulinum toxin".
Pearce L. Bruce, et al., Toxicon Elmsford, vol. 35, No. 9, p. 1373-1412, Sep. 1, 1997.
Pellett, et al., FEBS Lett., vol. 581, No. 25, p. 4803-4808, 2007.
Pellett, et al., Journal of Pharmacological and Toxicological Methods, vol. 61, No. 3, p. 304-310, May 1, 2010.
Pellizzari, R., et al., Toxicology Letters, vol. 102-103, p. 191-197, Dec. 28, 1998.
Purkiss, et al. Clostridium botulinum Neurotoxins Act with a Wide Range of Potencies on SH-SY5Y Human Neuroblastoma Cells. Neuro Toxicology 22:447-453, 2001.
Rassetti-Escargueil C., et al., Journal of The International Society on Toxinology Apr. vol. 53, No. 5, p. 503-511, Apr. 2009.
Schiavo, Giampietro, et al., Physiological Reviews, Apr. 2000, vol. 80, No. 2, pp. 717-766 "Neurotoxins affecting neuroexocytosis".
Schokett, Penny, et al., Current Protocols in Molecular Biology 1997, Suppl. 60, pp. 16.14.1-16.14.9 "Inducible gene expression using an autoregulatory, tetracycline-controlled system".
Sheridan, R.E., et al., Applied Toxicology, vol. 19, Suppl. 1, p. S29-S33, Dec. 1999.
Takahashi, K et al., Cell, vol. 131, Nov. 30, 2007, pp. 861-872, Induction of pluripotent stem cells from adult human fibroblasts by defined factors.
Vertiev, et al., "Effective expression of fragments of a botulinum neurotoxin type A gene, coding for the L-chain and H-chain in *E. coli*, with formation of products causing protective immunity to administration of the toxin", Mol Gen Mikrobiol Virusol, vol. 4, 2000, pp. 3-7.
Williamson. L.C., et al., Journal of Biological Chemistry, American Society for Biochemisty and Molecular Biology, vol. 271, No. 13, p. 7694-7699, Mar. 29, 1996.
Wohlfarth, K., et al., Naunyn-Schmiedebergs Archives of Pharmacology, vol. 355, No. 3, p. 335-340, Mar. 1997.
Barash and Arnon, J. Infect. Dis., (2014), vol. 209, No. 2, pp. 183-191.
Creative Diagnostics; Product Literature for Anti-Snap-25 monoclonal antibody, clone C318M (DMAB4345), pp. 1-2; Retreived from the Internet on Jul. 28, 2020.
Dover, N. et al.. J Infect Dis, (2014), vol. 209, No. 2, pp. 192-202.
Hill et al., J Bacteriol., (2007), vol. 189, No. 3, pp. 818-832.
International Search Report in International Application No. PCT/EP2015/053403, dated Apr. 17, 2015.
Kroken, et al. J. Biolog. Chem., (2011), vol. 286, No. 30, 26828-26837.
McNutt, et al., Cell Based Assay for Neurotoxins, Chapter 12, pp. 247-271, Springer Science+Business Media Dordrecht, 2015, P. Gopalakrishnakone et al (eds) Biological Toxins and Bioterrorism, Toxicology.
Pellett, Sabina, Curr. Top. Microbiol. Immunol., 2013, 364:257-285.
Sawyer, Peptide Based Drug Design, ACS, (1995), pp. 378-422.
Vlaev, et al. Appl Microbiol. Biotechnol., 2013, 97:5303-5313.
Yowler, et al. J. Biolog. Chem., 2002, vol. 277, pp. 32815-32819.
Zhu, et al. Cell & Developmental Biology, vol. 13, pp. 121-128, 2002.

* cited by examiner

MEANS AND METHODS FOR THE DETERMINATION OF THE BIOLOGICAL ACTIVITY OF NEUROTOXIN POLYPEPTIDES IN CELLS

The present invention pertains to a method for directly determining the biological activity of a Neurotoxin polypeptide in cells, comprising the steps of: a) incubating cells susceptible to Neurotoxin intoxication with a Neurotoxin polypeptide for a time and under conditions which allow for the Neurotoxin polypeptide to exert its biological activity; b) fixing the cells and, optionally, permeabilizing the cells with a detergent; c) contacting the cells with at least a first capture antibody specifically binding to the non-cleaved and Neurotoxin-cleaved substrate and with at least a second capture antibody specifically binding to the cleavage site of the Neurotoxin-cleaved substrate, under conditions which allow for binding of said capture antibodies to said substrates; d) contacting the cells with at least a first detection antibody specifically binding to the first capture antibody, under conditions which allow for binding of said first detection antibody to said first capture antibody, thus forming first detection complexes, and at least a second detection antibody specifically binding to the second capture antibody, under conditions which allow for binding of said second detection antibody to said second capture antibody, thus forming second detection complexes; e) determining the amount of the first and second detection complexes of step d), and f) calculating the amount of substrate cleaved by said Neurotoxin polypeptide in said cells by means of the second detection complexes, thereby determining the biological activity of said Neurotoxin polypeptide in said cells. The invention further provides for a kit for carrying out the method of the invention.

*Clostridium botulinum* and *Clostridium tetani* produce highly potent Neurotoxins, i.e. Botulinum toxins (BoNTs) and Tetanus toxin (TeNT), respectively. These Clostridial Neurotoxins (CNTs) specifically bind to neuronal cells and disrupt neurotransmitter release. Each toxin is synthesized as an inactive unprocessed approximately 150 kDa single-chain protein. The posttranslational processing involves formation of disulfide bridges, and limited proteolysis (nicking) by the bacterial protease(s). Active Neurotoxin consists of two chains, an N-terminal light chain of approx. 50 kDa and a heavy chain of approx. 100 kDa linked by a disulfide bond. CNTs structurally and functionally consist of three domains, i.e. the catalytic light chain, the heavy chain encompassing the translocation domain (N-terminal half) and the receptor binding domain (C-terminal half); see, e.g., Krieglstein 1990, Eur. J. Biochem. 188, 39; Krieglstein 1991, Eur. J. Biochem. 202, 41; Krieglstein 1994, J. Protein Chem. 13, 49. The Botulinum Neurotoxins are synthesized as molecular complexes comprising the 150 kDa Neurotoxin protein and associated non-toxic proteins. The complex sizes differ based on the Clostridial strain and the distinct Neurotoxin serotypes ranging from 300 kDa, over 500 kDa, and 900 kDa. The non-toxic proteins in these complexes stabilize the Neurotoxin and protect it against degradation; see Silberstein 2004, Pain Practice 4, S19-S26.

*Clostridium botulinum* secretes seven antigenically distinct serotypes designated A to G of the Botulinum Neurotoxin (BoNT). All serotypes together with the related Tetanus Neurotoxin (TeNT) secreted by *Clostridium tetani*, are $Zn^{2+}$-endoproteases that block synaptic exocytosis by cleaving SNARE proteins; see Couesnon, 2006, Microbiology, 152, 759. CNTs cause the flaccid muscular paralysis seen in botulism and tetanus; see Fischer 2007, PNAS 104, 10447.

Despite its toxic effects, Botulinum toxin complex has been used as a therapeutic agent in a large number of diseases. Botulinum toxin serotype A was approved for human use in the United States in 1989 for the treatment of strabism, blepharospasm, and other disorders. It is commercially available as Botulinum toxin A (BoNT/A) protein preparation, for example, under the trade name BOTOX (Allergan, Inc.) or under the trade name DYSPORT/RELOXIN (Ipsen, Ltd). An improved, complex-free Botulinum toxin A preparation is commercially available under the trade name XEOMIN (Merz Pharmaceuticals, LLC). For therapeutic applications, the preparation is injected directly into the muscle to be treated. At physiological pH, the toxin is released from the protein complex and the desired pharmacological effect takes place. The effect of Botulinum toxin is only temporary, which is the reason why repeated administration of Botulinum toxin may be required to maintain a therapeutic affect.

The Clostridial Neurotoxins weaken voluntary muscle strength and are effective therapy for strabism, focal dystonia, including cervical dystonia, and benign essential blepharospasm. They have been further shown to relief hemifacial spasm, and focal spasticity, and moreover, to be effective in a wide range of other indications, such as gastrointestinal disorders, hyperhidrosis, and cosmetic wrinkle correction; see Jost 2007, Drugs 67, 669.

During the manufacturing process of Clostridial Neurotoxins, the qualitative and quantitative determination of said Neurotoxins as well as the quality control of the biologically active Neurotoxin polypeptides is of particular importance. In addition, governmental agencies accept only simple, reliable, and validated Botulinum toxin activity assays. At present the mouse $LD_{50}$ bioassay, a lethality test, remains the "gold standard" used by pharmaceutical manufacturers to analyze the potency of their preparations; see Arnon et al. (2001), JAMA 285, 1059-1070. However, in recent years, considerable effort has been undertaken to seek for alternative approaches to alleviate the need for animal testing and all the disadvantages, costs and ethical concerns associated with this type of animal-based assays. In addition, the regulatory agencies are engaging pharmaceutical companies to apply the three "Rs" principle to the potency testing of Botulinum Neurotoxins: "Reduce, Refine, Replace"; see Straughan, Altern. Lab. Anim. (2006), 34, 305-313. As a consequence, cell-based test systems have been developed in order to provide reasonable alternatives to methods using live animals. Yet, only three cellular test systems are available for the determination of Neurotoxin biological activity thus far which have been shown to be sufficiently sensitive to Neurotoxin polypeptides. These cell-based test systems include the use of primary neurons isolated from rodent embryos which are differentiated in vitro (Pellett et al. (2011), Biochem. Biophys. Res. Commun. 404, 388-392), neuronal differentiated induced pluripotent stem cells (Whitemarsh et al. (2012), Toxicol. Sci. 126, 426-35), and a subclone of the SiMa cell line (WO 2010/105234 A1).

However, the isolation of primary neurons requires the killing of animals and is laborious and time consuming. Further, test systems using different primary neurons show large variances. Similarly, the generation of neuronal differentiated induced pluripotent stem cells is difficult and time consuming. In addition, storage of such cells is very problematic. Assays using tumor cell lines are frequently not sensitive enough to BoNT. Moreover, complex differentiation protocols are required for said tumor cell lines which result in large variances and/or high failure rates of assays using said cell lines.

Assays for determining the biological activity of Clostridial Neurotoxins described in the art include Western blot analysis in which the Neurotoxin activity is quantified by the amount of cleaved Neurotoxin substrate in cell lysates. In other assays, the activity of Clostridial Neurotoxins is measured by an electrochemoluminescence (ECL) sandwich ELISA; see WO 2009/114748 A1. Also in this case, the biological activity of the Clostridial Neurotoxin is determined by the detection of cleaved Clostridial Neurotoxin substrate after isolation from the cell lysate. Further, the Neurotoxin substrate has to be concentrated, in both assays.

In light of the above, further test systems for the determination of Neurotoxin polypeptide activity acceptable to governmental agencies and/or providing for an alternative to animal-based test systems are highly desirable.

Thus, the technical problem underlying the present invention may be seen as the provision of means and methods complying with the aforementioned needs. The technical problem is solved by the embodiments characterized in the claims and herein below.

The present invention relates, in a first aspect, to a method for directly determining the biological activity of a Neurotoxin polypeptide in cells, comprising the steps of:
a) incubating cells susceptible to Neurotoxin intoxication with a Neurotoxin polypeptide for a time and under conditions which allow for the Neurotoxin polypeptide to exert its biological activity;
b) fixing the cells and, optionally, permeabilizing the cells with a detergent;
c) contacting the cells with at least a first capture antibody specifically binding to the non-cleaved and Neurotoxin-cleaved substrate and with at least a second capture antibody specifically binding to the cleavage site of the Neurotoxin-cleaved substrate, under conditions which allow for binding of said capture antibodies to said substrates;
d) contacting the cells with at least a first detection antibody specifically binding to the first capture antibody, under conditions which allow for binding of said first detection antibody to said first capture antibody, thus forming first detection complexes and at least a second detection antibody specifically binding to the second capture antibody, under conditions which allow for binding of said second detection antibody to said second capture antibody, thus forming second detection complexes;
e) determining the amount of the first and second detection complexes of steps d); and
f) calculating the amount of substrate cleaved by said Neurotoxin polypeptide in said cells by means of the second detection complexes, thereby determining the biological activity of said Neurotoxin polypeptide in said cells.

The method of the invention allows for the direct determination of the biological activity of a Neurotoxin polypeptide in cells. This means that no lysis of the cells and no isolation or concentration of the cleaved Neurotoxin substrate from cell lysates is necessary any longer, as in the methods described in the art. For example, in the Western blot analysis-based assay of the art, the Neurotoxin substrate is concentrated by the separation and concentration of the components of the respective sample in the SDS polyacrylamide gel. In the aforementioned ECL sandwich ELISA described in the art, the concentration of the Neurotoxin substrate is carried out by using antibodies which bind specifically to the cleaved Neurotoxin substrate on a microtiter plate to which the cell lysate is added. The cleaved Neurotoxin substrate is isolated from the lysate by binding of the mentioned antibody which results in a concentration of said cleaved Clostridial Neurotoxin substrate. In contrast, the cleaved Neurotoxin substrate, as exemplified for SNAP-25, can be directly detected in the cell, in the method of the invention. To this end, cells which are susceptible to Neurotoxin intoxication as defined in more detail elsewhere herein are incubated with a Neurotoxin polypeptide for a time and under conditions which allow for the Neurotoxin polypeptide to exert its biological activity. In a next step, the cells are fixed, for example, by addition of a fixation agent such as methanol, ethanol, acetone, formaldehyde or mixtures of the mentioned fixation agents. Optionally, the cells can be permeabilized by using at least one detergent as defined elsewhere herein such as Triton X-100, Tween 20, Saponin, Digitonin or n-Octyl-β-glucopyranoside. The detergent can be comprised in an appropriate buffer such as PBS. Thereafter, the cells are contacted with at least a first capture antibody which specifically binds to the non-cleaved and Neurotoxin-cleaved substrate and with at least a second capture antibody specifically binding to the cleavage site of the Neurotoxin-cleaved substrate, under conditions which allow for binding of said capture antibodies to said substrates. Herein, the first capture antibody is able to determine the total content or amount of Neurotoxin substrate in the cells, by binding specifically to an appropriate epitope present in both the non-cleaved and Neurotoxin-cleaved Neurotoxin substrate. The second capture antibody recognizes and binds specifically to an epitope present only in the cleaved Neurotoxin substrate, for example, by binding specifically to the Neurotoxin-cleaved site in the Neurotoxin substrate. Alternatively, the cells can be contacted with a mixture of said first and second capture antibodies, i.e. the cells are contacted with at least a first capture antibody and at least a second capture antibody simultaneously, under the mentioned conditions. In the next step, the cells are contacted with at least a first detection antibody specifically binding to the first capture antibody under conditions which allow for binding of said first detection antibody to said first capture antibody, thus forming first detection complexes. In a subsequent step, the cells are contacted with at least a second detection antibody specifically binding to the second capture antibody, under conditions which allow for binding of said second detection antibody to said second capture antibody, thus forming second detection complexes. Alternatively, the cells can be contacted with a mixture of said first and second detection antibodies, i.e. the cells are contacted with at least a first detection antibody and at least a second detection antibody simultaneously, under the mentioned conditions. Alternatively, after permeabilization of the cells, they can be contacted with a mixture of said first and second capture antibodies and said first and second detection antibodies simultaneously, under the mentioned conditions. In the next step, the amounts of the first and second detection complexes are determined. Finally, the amount of substrate cleaved by said Neurotoxin polypeptide in said cells is calculated by means of the second detection complexes. Thereby, the biological activity of said Neurotoxin polypeptide is determined directly in the cells.

In the following, the method of the invention is described in more detail. For cell culture, the cells susceptible to Neurotoxin intoxication as defined herein, such as neuronal cells, SiMa cells or iPS-derived neurons, are first seeded on 96 well microtiter plates. SiMa cells are differentiated to a neuronal phenotype, for example, according to the procedures disclosed in WO 2010/105234, and iPS-derived neurons are differentiated to a neuronal phenotype, e.g., according to assays described in WO 2012/135621. Then, the cells are intoxicated with a Neurotoxin polypeptide, such as BoNT/A, for about 72 hours. In the subsequent step, the cells are fixed on the microtiter plate, prior to the ELISA assay. For fixing the cells, for example ice-cold methanol (−20° C.) can be added to the cells for 20 minutes at −20° C.

For performing the ELISA assay, the cells are first washed. As a wash buffer, e.g., 0.1% Triton X-100 in 10 mM PBS buffer (pH 7.4) can be used. Thereafter, endogenous proteases are quenched by a quenching buffer such as 0.6% $H_2O_2$ in 10 mM PBS (pH 7.4), followed by another wash step. In the following step, free binding sites on the microtiter plate are blocked by an appropriate blocking buffer such as, for instance, 2% BSA in 10 mM PBS buffer (pH 7.4) and 0.05% Triton X-100. Then, the cells are permeabilized, by using an appropriate detergent. As a permeabilization buffer, e.g., 0.5% Triton X-100 in 10 mM PBS buffer can be utilized. Permeabilization allows the diffusion of the antibodies through the pores formed in the cells. Thereafter, the cells are washed by washing buffer as mentioned above.

In the next step, the permeabilized cells are incubated, e.g., with a mixture of two different antibodies. The mixture comprises a first capture antibody specifically binding to the non-cleaved and Neurotoxin-cleaved substrate and a second capture antibody specifically binding to the cleavage site of the Neurotoxin-cleaved substrate. Said first and second capture antibodies can also be applied subsequently. For example, the first capture antibody can specifically bind to both non-cleaved and Neurotoxin-cleaved SNAP-25, thereby allowing for the quantification of the total amount or content of SNAP-25 in the cells. Further, this first capture antibody can be used for the normalization of the amount of cleaved SNAP-25 in the cells, upon evaluation as described herein. The second capture antibody specifically binds to the cleavage site of the Neurotoxin-cleaved substrate and therefore allows the determination and detection of the cleaved Neurotoxin substrate, such as BoNT/A-cleaved SNAP-25.

The following detection of the total Neurotoxin substrate and the Neurotoxin-cleaved Neurotoxin substrate in the method of the invention can be carried out directly on the microtiter plate or cell culture dish, i.e. within the cells. Advantageously, it is therefore not necessary to prepare cell extracts and to isolate and/or concentrate the Neurotoxin substrate from the cell lysate in the method of the invention, as in the methods described in the art. Thereafter, the cells are washed in order to remove excess antibody not bound to the respective antigen. In the subsequent step, the permeabilized cells are contacted with at least a first detection antibody and at least a second detection antibody. Said antibodies can be applied as a mixture, i.e. simultaneously, or subsequently. The first detection antibody specifically binds to the first capture antibody. Thereby, first detection complexes are being formed. The first detection antibody can be directed against the species from which the first capture antibody is derived from. For example, in case the rabbit polyclonal anti-SNAP-25 antibody S9684 (Sigma) is used as a first capture antibody specifically binding to the non-cleaved and BoNT/A-cleaved substrate SNAP-25, an anti-rabbit alkaline phosphatase-conjugated antibody can be used as a first detection antibody. The second detection antibody specifically binds to the second capture antibody. Thereby, second detection complexes are being formed. The second detection antibody can be directed against the species from which the second capture antibody is derived from. For instance, in case the mouse monoclonal antibody (mAb) 20-2-5 of the invention described elsewhere herein is used as a second capture antibody specifically binding to the BoNT/A-cleaved SNAP-25, an anti-mouse horseradish peroxidase (HRP)-conjugated antibody can be used as a second detection antibody. It is evident to those skilled in the art that the first detection antibody and the second detection antibody are conjugated with different enzymes in order to allow for the specific detection of the respective first and second capture antibody as used in the method of the invention. For instance, the HRP-based detection as described elsewhere herein can be used for the BoNT/A-cleaved SNAP-25 and the alkaline phosphatase-based detection for the total (BoNT/A-cleaved and non-cleaved) SNAP-25. Thereafter, the cells are washed again. In a subsequent step, a fluorogenic HRP substrate is added to the cells. As a HRP substrate, e.g., Amplex UltraRed (Invitrogen) can be used which is excited at 540 nm and which emits at 600 nm. Incubation with the HRP substrate is carried out for a time sufficient for sufficient conversion of substrate by the horseradish peroxidase. Subsequent to the incubation with the HRP substrate, for example, the AP substrate DiFMUP (6,8-difluoro-4-methylumbelliferyl phosphate; excitation 360 nm; emission 450 nm) can be added to the HRP substrate and the cells are incubated with a mixture of said two substrates. Incubation with said AP substrate is carried out for a time which allows for sufficient conversion of substrate by the alkaline phosphatase. As known in the art, a substrate has to be converted in an amount which is sufficient so that the measured signal is at least as high as the mean value of the blank plus three standard deviations of the mean, according to the definition of limit of detection. The limit of detection can be determined as described in the literature; see, e.g., Armbruster and Pry, Clinical Biochem. Rev. 2008, 29 (Supplement 1): S49-S52. Because the pH optimum of the alkaline phosphatase is in the alkaline region, the corresponding substrate buffer is strongly alkaline. If the alkaline phosphatase substrate is added to the HRP substrate, the reaction of the horseradish peroxidase is stopped by the alkaline pH and the alkaline phosphatase converts DiFMUP. Converted HRP substrate is not influenced by the alkaline pH. Finally, the fluorescence of the two substrates is measured as follows:

Amplex UltraRed: Excitation 540 nm; emission 600 nm
DiFMUP: Excitation 360 nm; emission 450 nm As appreciated by those skilled in the art, only those fluorogenic substrates are appropriate for detection of the first and second capture antibody in the method of the invention which exhibit different excitation/emission wave lengths of the used substrates. Only in this case, they allow for the specific detection of each antigen, i.e. the total Neurotoxin substrate (such as non-cleaved and Neurotoxin-cleaved SNAP-25) and the cleaved Neurotoxin substrate (such as Neurotoxin-cleaved SNAP-25). Thereby, it is possible to quantify the total content of Neurotoxin substrate and the content of cleaved Neurotoxin substrate in every well or cell culture dish at the same time. In light of this, it is advantageously possible to automatize the method of the invention. As set forth elsewhere herein it is envisaged that the fluorogenic substrates chosen for the method of the invention exhibit a sufficient shift between the excitation/emission spectra in order to allow for the specific detection of the respective substrate. This requirement is fulfilled, for example, for the HRP substrate Amplex and its derivatives and for the AP substrate DiFMUP. Whereas, in an optimal case, there is no overlap between the excitation/emission spectra of the used fluorogenic substrates, it has been experienced that an overlap of up to 30% in the peak area of the excitation spectra of the used fluorogenic substrates is tolerable.

As further acknowledged by those skilled in the art, the method of the present invention allows for the direct detection and quantification of Neurotoxin substrate cleaved by the Neurotoxin polypeptide in the cells, thereby determining the biological activity of said Neurotoxin polypeptide in said cells. Advantageously, the method of the invention does not require the preparation of cell lysates or extracts and the isolation or concentration of the cleaved Neurotoxin substrate from the cell lysates/extracts, which is necessary for the methods known in the art. As a consequence of this, sample material can be saved. Further, the sample preparation and the number of samples can be reduced by the method of the invention since the amount of total Neurotoxin substrate and the amount of cleaved Neurotoxin substrate in the sample can be determined at the same time. In the assays described in the art, the samples have to be subdivided in order to detect both antigens, i.e. total Neurotoxin substrate and cleaved Neurotoxin substrate, separately from each other. The method of the invention renders the subdivision of the sample unnecessary. Thereby, inhomogeneities resulting from the subdivision of samples can be avoided and sample material can be saved. Furthermore, antigens can be degraded in the assays described in the art which can falsify the detection of the cleaved Neurotoxin substrate. This is because in the assays described in the art, the cells are incubated with detergent-containing lysis buffers which, however, are not able to inactivate the Neurotoxin polypeptide or other endogenous proteases resulting in degradation of the Neurotoxin substrate upon longer storage of the samples. Stronger lysis buffers cannot be used in the ECL sandwich ELISA described in the prior art due to the required use of the cell lysate in said assay. This is because the aggregation of the above-mentioned antigens can result in unspecific adsorption of the antigens to the plastic surface of the cell culture dishes or microtiter plates which in turn disturbs the detection of the antigens by appropriate antibodies. Since the antibodies for the detection of the antigens get into contact with the lysate, too, the antibodies can also aggregate. In this case, no reliable and accurate detection of the antigen is possible anymore. The present inventors have experienced such degradation reactions by using Western blot assays for the detection of the biological activity of Neurotoxin activity described in the art. Upon longer storage of lysates at −20° C., in comparison to fresh lysate samples the detection signal of total SNAP-25 has been found to be strongly reduced and the ratio of cleaved Neurotoxin substrate SNAP-25 to un-cleaved Neurotoxin substrate SNAP-25 had shifted due to degradation processes during the freezing. It has been found by the present inventors that the degradation of the Neurotoxin substrate and/or the instability of the samples can be avoided by directly fixing the cells on the cell culture dish because both the Neurotoxin substrate and the Neurotoxin or other endogenous proteases are inactivated immediately by aggregation on the cell culture dish. This can be achieved by using, for example, fixing of the cells by methanol or other fixatives or fixation agents known in the art, such as ethanol, acetone, formaldehyde or mixtures thereof or other fixation agents described herein. The analysis of the stability of, e.g., parental SiMa cells (human neuroblastoma cells; DSMZ no.: ACC 164) and iPS-derived neurons (Whitemarsh et al. (2012), Toxicol. Sci. 126, 426-35) using this fixation method did not reveal any differences between fresh and cell culture dishes stored seven days in the refrigerator.

As used herein, the singular forms "a", "an" and "the" include both singular and plural reference unless the context clearly dictates otherwise. By way of example, "a cell" refers to one or more than one cell.

As used herein, the term "about" when qualifying a value of a stated item, number, percentage, or term refers to a range of plus or minus 10 percent, 9 percent, 8 percent, 7 percent, 6 percent, 5 percent, 4 percent, 3 percent, 2 percent or 1 percent of the value of the stated item, number, percentage, or term. Preferred is a range of plus or minus 10 percent.

The terms "comprising", "comprises" and "comprised of" as used herein are synonyms with "including", "includes" or "containing", "contains", and are inclusive or open-ended and do not exclude additional, non-recited members, elements or method steps. Evidently, the term "comprising" encompasses the term "consisting of". More specifically, the term "comprise" as used herein means that the claim encompasses all the listed elements or method steps, but may also include additional, unnamed elements or method steps. For example, a method comprising steps a), b) and c) encompasses, in its narrowest sense, a method which consists of steps a), b) and c). The phrase "consisting of" means that the composition (or device, or method) has the recited elements (or steps) and no more. In contrast, the term "comprises" can encompass also a method including further steps, e.g., steps d) and e), in addition to steps a), b) and c).

In case numerical ranges are used herein such as "in a concentration between 1 and 5 micromolar", the range includes not only 1 and 5 micromolar, but also any numerical value in between 1 and 5 micromolar, for example, 2, 3 and 4 micromolar.

The term "in vitro" as used herein denotes outside, or external to, the animal or human body. The term "in vitro" as used herein should be understood to include "ex vivo". The term "ex vivo" typically refers to tissues or cells removed from an animal or human body and maintained or propagated outside the body, e.g., in a culture vessel. The term "in vivo" as used herein denotes inside, or internal to, the animal or human body.

The term "Neurotoxin polypeptide" as used herein denotes *Clostridium botulinum* and *Clostridium tetani* Neurotoxins, i.e. Botulinum toxins (BoNTs) and Tetanus toxin (TeNT). More specifically, said term encompasses BoNT/A, BoNT/B, BoNT/C1, BoNT/D, BoNT/E, BoNT/F, BoNT/G, and Tetanus Neurotoxin (TeNT). The Neurotoxin polypeptide and, in particular, its light chain and heavy chain are derivable from one of the antigenically different serotypes of Botulinum Neurotoxins indicated above. In an aspect, said light and heavy chain of the neurotoxin polypeptide are the light and heavy chain of a neurotoxin selected from the group consisting of: BoNT/A, BoNT/B, BoNT/C1, BoNT/D, BoNT/E, BoNT/F, BoNT/G or TeNT. In another aspect, the polynucleotide encoding said Neurotoxin polypeptides comprises a nucleic acid sequence as shown in SEQ ID NO: 1 (BoNT/A), SEQ ID NO: 3 (BoNT/B), SEQ ID NO: 5 (BoNT/C1), SEQ ID NO: 7 (BoNT/D), SEQ ID NO: 9 (BoNT/E), SEQ ID NO: 11 (BoNT/F), SEQ ID NO: 13 (BoNT/G) or SEQ ID NO: 15 (TeNT). Moreover, encompassed is, in an aspect, a polynucleotide comprising a nucleic acid sequence encoding an amino acid sequence as shown in any one of SEQ ID NO: 2 (BoNT/A), SEQ ID NO: 4 (BoNT/B), SEQ ID NO: 6 (BoNT/C1), SEQ ID NO: 8 (BoNT/D), SEQ ID NO: 10 (BoNT/E), SEQ ID NO: 12 (BoNT/F), SEQ ID NO: 14 (BoNT/G) or SEQ ID NO: 16 (TeNT). Further encompassed is in an aspect of the means and methods of the present invention, a Neurotoxin polypeptide comprising or consisting of an amino acid sequence selected from the group consisting of: SEQ ID NO: 2 (BoNT/A), SEQ ID NO: 4 (BoNT/B), SEQ ID NO: 6 (BoNT/C1), SEQ ID NO: 8 (BoNT/D), SEQ ID NO: 10 (BoNT/E), SEQ ID NO: 12 (BoNT/F), SEQ ID NO: 14 (BoNT/G) and SEQ ID NO: 16 (TeNT).

In another aspect, the said polynucleotide is a variant of the aforementioned polynucleotides comprising one or more nucleotide substitutions, deletions and/or additions which in still another aspect may result in a polypeptide having one or more amino acid substitutions, deletions and/or additions. Moreover, a variant polynucleotide of the invention shall in another aspect comprise a nucleic acid sequence variant being at least 40%, at least 50%, at least 60%, at least 70%, at least 75%, at least 80%, at least 85%, at least 90%, at least 95%, at least 96%, at least 97%, at least 98% or at least 99% identical to the nucleic acid sequence as shown in any one of SEQ ID NOs: 1, 3, 5, 7, 9, 11, 13 or 15 or a nucleic acid sequence variant which encodes an amino acid sequence being at least 40%, at least 50%, at least 60%, at least 70%, at least 75%, at least 80%, at least 85%, at least 90%, at least 95%, at least 96%, at least 97%, at least 98% or at least 99% identical to the amino acid sequence as shown in any one of SEQ ID NOs: 2, 4, 6, 8, 10, 12, 14, or 16. The term "identical" as used herein refers to sequence identity characterized by determining the number of identical amino acids between two nucleic acid sequences or two amino acid sequences wherein the sequences are aligned so that the highest order match is obtained. It can be calculated using published techniques or methods codified in computer programs such as, for example, BLASTP, BLASTN or FASTA (Altschul 1990, J Mol Biol 215, 403). The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wisconsin, USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. In an aspect, each of the aforementioned variant polynucleotides encodes a polypeptide retaining one or more and, in another aspect, all of the biological properties of the respective Neurotoxin polypeptide, i.e. the BoNT/A, BoNT/B, BoNT/C1, BoNT/D, BoNT/E, BoNT/F, BoNT/G or Tetanus Neurotoxin (TeNT). Those of skill in the art will appreciate that full biological activity is maintained only after proteolytic activation, even though it is conceivable that the unprocessed precursor can exert some biological functions or be partially active. "Biological properties" as used herein refers to (a) receptor binding, (b) internalization, (c) translocation across the endosomal membrane into the cytosol, and/or (d) endoproteolytic cleavage of proteins involved in synaptic vesicle membrane fusion. In vivo assays for assessing biological activity include the mouse LD50 assay and the ex vivo mouse hemidiaphragm assay as described by Pearce et al. (Pearce 1994, Toxicol. Appl. Pharmacol. 128: 69-77) and Dressler et al. (Dressler 2005, Mov. Disord. 20:1617-1619, Keller 2006, Neuroscience 139: 629-637). The biological activity is commonly expressed in Mouse Units (MU). As used herein, 1 MU is the amount of neurotoxic component, which kills 50% of a specified mouse population after intraperitoneal injection, i.e. the mouse i.p. LD50. In a further aspect, the variant polynucleotides can encode Neurotoxins having improved or altered biological properties, e.g., they may comprise cleavage sites which are improved for enzyme recognition or may be improved for receptor binding or any other property specified above.

Accordingly, the term "biological activity of a Neurotoxin polypeptide" as used herein means the biological properties characteristic for a Neurotoxin polypeptide, namely, a) receptor binding, (b) internalization, (c) translocation across the endosomal membrane into the cytosol, and/or (d) endoproteolytic cleavage of proteins involved in synaptic vesicle membrane fusion. It is envisaged that the Neurotoxin polypeptide as used herein exhibits at least one of the properties a) to d) mentioned above, preferably endoproteolytic cleavage of proteins involved in synaptic vesicle membrane fusion, or two or three or all four biological properties listed in a) to d).

Aspects of the present disclosure comprise, in part, a cell from an established cell line. As used herein, the term "cell" refers to any eukaryotic cell susceptible to Neurotoxin intoxication by a Neurotoxin such as, e.g., BoNT/A, or any eukaryotic cell that can uptake a Neurotoxin. The term cell encompasses cells from a variety of organisms, such as, e.g., murine, rat, porcine, bovine, equine, primate and human cells; from a variety of cell types such as, e.g., neuronal and non-neuronal; and can be isolated from or part of a heterogeneous cell population, tissue or organism. As used herein, the term "established cell line" is synonymous with "immortal cell line," or "transformed cell line" and refers to a cell culture of cells selected for indefinite propagation from a cell population derived from an organism, tissue, or organ source. By definition, an established cell line excludes a cell culture of primary cells. As used herein, the term "primary cells" are cells harvested directly from fresh tissues or organs and do not have the potential to propagate indefinitely. For example, primary neuronal cells can be used in the method of the invention. An established cell line can comprise a heterogeneous population of cells or a uniform population of cells. An established cell line derived from a single cell is referred to as a clonal cell line. An established cell line can be one whose cells endogenously express all component necessary for the cells to undergo the overall cellular mechanism whereby a Neurotoxin, such as BoNT/A, proteolytically cleaves a substrate, such as SNAP-25, and encompasses the binding of a Neurotoxin to a Neurotoxin receptor, such as BoNT/A, to a BoNT/A receptor, the internalization of the neurotoxin/receptor complex, the translocation of the Neurotoxin light chain from an intracellular vesicle into the cytoplasm and the proteolytic cleavage of a Neurotoxin substrate. Alternatively, an established cell line can be one whose cells have had introduced from an exogenous source at least one component necessary for the cells to undergo the overall cellular mechanism whereby a Neurotoxin, such as BoNT/A, proteolytically cleaves a substrate, such as SNAP-25, and encompasses the binding of a Neurotoxin to a receptor, such as BoNT/A to a BoNT/A receptor, the internalization of the neurotoxin/receptor complex, the translocation of the Neurotoxin light chain from an intracellular vesicle into the cytoplasm and the proteolytic cleavage of a Neurotoxin substrate. Also referred to as a genetically-engineered cell line, cells from such an established cell line may, e.g., express an exogenous FGFR2, an exogenous FGFR3, an exogenous SV2, an exogenous Neurotoxin substrate such as SNAP-25, or any combination thereof.

The term "cell(s) susceptible to Neurotoxin intoxication" as denoted herein means a cell that can undergo the overall cellular mechanisms whereby a Neurotoxin polypeptide (e.g., BoNT/A) cleaves a Neurotoxin substrate (e.g., the BoNT/A substrate SNAP-25) and encompasses the binding of the Neurotoxin to its corresponding receptor (e.g., binding of BoNT/A to the BoNT/A receptor), the internalization of the Neurotoxin/receptor complex, the translocation of the Neurotoxin light chain from an intracellular vesicle into the cytoplasm and the proteolytic cleavage of the Neurotoxin substrate. Assays for determining the biological activity of Neurotoxin polypeptides are well known in the art and also described elsewhere herein; see, e.g., Pellett et al. (2011), Biochem. Biophys. Res. Commun. 404, 388-392; Whitemarsh et al. (2012), Toxicol. Sci. 126, 426-35. Accordingly, a "cell susceptible to Neurotoxin intoxication" as used herein means a Neurotoxin sensitive cell. The mentioned term comprises a cell or a cell line, for example, an isolated, primary cell or a cell line thereof or a cell of an established cell line or an established cell line, for example, tumor cells or tumor cell lines which are capable of differentiating to neuronal cells, such as neuroblastoma cells or neuroblastoma cell lines as defined elsewhere herein. For example, said neuroblastoma cell line can be a SiMa cell line which is commercially available from DSMZ (ACC 164). Specific clones of the cell line SiMa are furthermore disclosed in WO 2010/105234. Other neuroblastoma cell lines which can be used in the method of the invention can be obtained from ATCC or DSMZ, under the following ATCC or DSMZ numbers: Cell line N1E-115 under CRL-2263, cell line Neuro2a under CCL-131, cell line SH-SY5Y under CRL-2266, cell line PC12 under CRL-1721, cell line MHH-NB-11 under ACC 157 (DSMZ) and cell line SK-N-BE(2) under CRL-2271. Other tumor cells which are susceptible to Neurotoxin intoxication are P-19 cells (murine embryonal carcinoma cell line) (DSMZ no. ACC 316). Further encompassed by cells susceptible to Neurotoxin intoxication are induced pluripotent stem cell (iPS)-derived neurons, preferably human induced pluripotent stem cell (iPS)-derived neurons; see, e.g., Whitemarsh et al. (2012), loc. cit. Such human iPS-derived neurons are also commercially available, for instance, from Cellular Dynamics. Methods of generating iPS cells are described, for example, in Yu et al. (Science 2009 May 8; 324(5928): 797-801. Epub 2009), WO 2011/056971 and WO 2011/025852. In some aspects, iPS are differentiated into neurons using suitable methods, e.g., those described in WO 2012/135621 and U.S. Patent Applications US 2010/0279403 and US 2010/0216181.

The term "fixing the cells" means fixing the cells using methods described in the art. Generally, fixation is a chemical process by which biological tissues are preserved from decay, thereby preventing autolysis. Fixation terminates any ongoing biochemical reactions, and may also increase the mechanical strength or stability of the treated tissues. Fixation preserves a sample of biological material such as a tissue or cells as close to its natural state as possible in the process of preparing said tissue or cells for examination or analysis. To this end, a fixative usually acts to disable intrinsic biomolecules—particularly proteolytic enzymes—which otherwise digests or damages the sample. Further, a fixative typically protects a sample from extrinsic damage. Fixatives are toxic to most common microorganisms including bacteria that might exist in a tissue or cell culture or which might otherwise colonize the fixed tissue or cell culture. In addition, many fixatives chemically alter the fixed material to make it less palatable either indigestible or toxic to opportunistic microorganisms. Finally, fixatives often alter the cells or tissues on a molecular level to increase their mechanical strength or stability. This increased strength and rigidity can help preserve the morphology such as shape and structure of the sample as it is processed for further analysis. It is evident to those skilled in the art that the choice of fixative and fixation protocol may depend on the additional processing steps and final analyses that are planned. For example, immunohistochemistry uses antibodies that bind specifically to a specific protein target, the antigen. Prolonged fixation can chemically mask these targets and prevent antibody binding. In these cases, for example, a quick fixation method using cold formalin can be used. Alternatively, the cells can be fixed by adding ice-cold methanol (−20° C.). Besides aldehydes such as formaldehyde or glutaraldehyde and alcohols such as ethanol or methanol, oxidizing agents, Hepes-glutamic acid buffer-mediated organic solvent protection effect (HOPE) fixative, acetone, or mixtures thereof, such as a mixture of methanol and acetone, methanol and ethanol, paraformaldehyde and Triton X-100, or paraformaldehyde and methanol, can be used in fixation protocols. In one aspect of the method of the invention, fixing the cells is carried out by the addition of a fixation agent selected from the group consisting of: methanol, ethanol, acetone, formaldehyde or mixtures thereof. To ensure and/or support free access of the antibody to its antigen, the cells can, optionally, be permeabilized by using an appropriate permeabilization buffer comprising at least one detergent, such as Triton X-100. A permeabilization buffer which can be used in the method of the invention is, e.g., 0.5% Triton X-100 in 10 mM PBS buffer. In other aspects of the methods of the invention, the cells can be permeabilized by using a permeabilization buffer such as PBS comprising at least one detergent selected from Tween 20, Saponin, Digitonin or n-Octyl-β-glucopyranoside. In other aspects, mixtures of two or more of the detergents mentioned herein can be used in the said permeabilization buffer. In general, fixation strengths and times are considerably shorter for cells than on the thicker, structurally complex tissue sections. For immunocytochemistry, sample preparation essentially entails fixing the target cells to the slide, cell culture dish or microtiter plate. Perfect fixation would immobilize the antigens, while retaining authentic cellular and subcellular architecture and permitting unhindered access of antibodies to all cells and subcellular compartments. Wide ranges of fixatives as exemplified above are commonly used, and the correct choice of method will depend on the nature of the antigen being examined and on the properties of the antibody used. Fixation methods fall generally into two classes: organic solvents and cross-linking reagents. Organic solvents such as alcohols and acetone remove lipids and dehydrate the cells, while precipitating the proteins on the cellular architecture. Cross-linking reagents such as paraformaldehyde form intermolecular bridges, normally through free amino groups, thus creating a network of linked antigens. Cross-linkers preserve cell structure better than organic solvents, but may reduce the antigenicity of some cell components, and often require the addition of a permeabilization step as indicated above, to allow access of the antibody to the specimen. Fixation with both methods may denature protein antigens, and for this reason, antibodies prepared against denatured proteins may be more useful for cell staining. The appropriate fixation method should be chosen according to the relevant application. Fixing methods of cells are well described in the art (see, e.g., Methods in cell biology, Volume 37: Antibodies in cell biology; Edited by David J. Asai; 1993, Academic Press Inc.).

The term "contacting" as used in accordance with the method of the invention means bringing the cells and the respective antibodies in physical proximity as to allow physical and/or chemical interaction. Suitable conditions which allow for specific interaction are well known to the person skilled in the art. Evidently, said conditions will depend on the antibodies and the cells to be applied in the method of the present invention and can be adapted routinely by the person skilled in the art. Moreover, a time being sufficient to allow interaction can also be determined by the skilled worker without further ado. It is to be understood that between the individual steps of contacting the cells and the respective antibodies recited in the method of the present invention, washing steps may be performed in order to obtain suitable conditions for contacting. For example, after contacting the cells with at least a first capture antibody specifically to the non-cleaved and Neurotoxin-cleaved substrate and with at least a second capture antibody specifically binding to the cleavage site of the Neurotoxin-cleaved substrate in step c) of the method of the invention, a washing step can be incorporated to remove the remaining solution and/or excess first and second capture antibody, prior to applying the first detection antibody and/or second detection antibody. Similarly, after bringing the cells into contact with the first and/or second detection antibody in the method of the invention, a wash step can be included. An appropriate wash buffer is, for example, 0.1% Triton X-100 in 10 mM PBS buffer (pH 7.4). More specifically, the term "contacting" as used herein, refers to bringing the cells into contact with at least a first capture antibody specifically binding to the non-cleaved and Neurotoxin-cleaved substrate and with at least a second capture antibody specifically binding to the cleavage site of the Neurotoxin-cleaved substrate, under conditions which allow for binding of said capture antibodies to said substrates, in step c) of the method of the invention. The first and second capture antibody can be applied to the cells simultaneously, for example, as a mixture, or subsequently. "Contacting" further refers to bringing into contact the cells with at least a first detection antibody specifically binding to the first capture antibody, under conditions which allow for binding of said first detection antibody to said first capture antibody, and at least a second detection antibody specifically binding to the second capture antibody, under conditions which allow for binding of said second detection antibody to said second capture antibody, in step d) of the method of the invention. Thereby, first and second detection complexes are being formed. Alternatively, the first and second detection antibodies can also be applied subsequently.

As used herein, the term "antibody" refers to a molecule generated by an immune system that was made in response to a particular antigen that specifically binds to that antigen, and includes both naturally occurring antibodies and non-naturally occurring antibodies. An "antibody" as used herein encompasses a monoclonal antibody, a polyclonal antibody, a single chain antibody, a dimer or a multimer, a chimerized antibody, a bispecific antibody, a bispecific single chain antibody, a multispecific antibody, a synthetic antibody, a humanized antibody, a bifunctional antibody, a cell-associated antibody like an Ig receptor, a linear antibody, a diabody, a minibody, or a fragment of any of said antibodies. Fragments of said antibodies include, e.g., Fab, Fv, or scFv fragments, or chemically modified derivatives of any of these fragments. Antibodies can be manufactured by using methods which are described in the art; see, for example, Harlow and Lane "Antibodies, A Laboratory Manual", CSH Press, Cold Spring Harbor, 1988. Monoclonal antibodies can be prepared by the techniques originally described in Köhler 1975, Nature 256, 495, and Galfré 1981, Meth. Enzymol. 73, 3. Said techniques comprise the fusion of mouse myeloma cells to spleen cells derived from immunized mammals. Antibodies can be further improved by techniques well known in the art. For example, surface plasmon resonance as employed in the Biacore system can be used to increase the efficiency of phage antibodies which bind to the epitope; see, e.g., Schier 1996, Human Antibodies Hybridomas 7, 97; Malmborg 1995, J. Immunol. Methods 183, 7. Antibodies as used herein also comprise functional equivalents of antibodies, i.e. agents which are capable of specifically binding to the desired epitopes or parts of the Neurotoxin substrates. In an aspect, such functional equivalents comprise binding proteins specifically binding to Neurotoxin substrates or domains thereof which are capable of mediating the said specific binding. An antibody as used herein can be a full-length immunoglobulin molecule comprising the VH and VL domains, as well as a light chain constant domain (CL) and heavy chain constant domains, CH1, CH2 and CH3, or an immunologically active fragment of a full-length immunoglobulin molecule, such as, e.g., a Fab fragment, a F(ab')$_2$ fragment, a Fc fragment, a Fd fragment, or a Fv fragment. An antibody can be derived from any vertebrate species (e.g., human, goat, horse, donkey, murine, rat, rabbit, or chicken), and can be of any type (e.g., IgG, IgE, IgM, IgD, or IgA), class (e.g., IgA, IgD, IgE, IgG, or IgM) or subclass (IgG1, IgG2, IgG3, IgG4, IgA1 or IgA2). For general disclosure on the structure of naturally occurring antibodies, non-naturally occurring antibodies, and antigenic compound-binding fragments thereof, see, e.g., Plueckthun in The Pharmacology of Monoclonal Antibodies, vol. 113, Rosenburg and Moore eds., Springer-Verlag, New York, pp. 269-315 (1994); Borrabeck, Antibody Engineering 2d ed. (Oxford University Press). Naturally-occurring antibodies are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The complete antigen-recognition and antigen-binding site is contained within the variable domains of the antibody, i.e., the Fv fragment. This fragment includes a dimer of one heavy chain variable domain (VH) and one light chain variable domain (VL) in tight, non-covalent association. Each domain comprises four framework regions (FR), which largely adopting a beta-sheet configuration, connected by three hypervariable regions, which form loops connecting, and in some cases form part of, the beta-sheet structure. Each hypervariable region comprises an amino acid sequence corresponding to a complementarity determining region (CDRs). Collectively, it the three-dimensional configuration of the six CDR regions that define an antigen-binding site on the surface of the VH-VL dimer that confers antigen-binding specificity. See e.g., Cyrus Chothia, et al., Conformations of Immunoglobulin Hypervariable Regions, Nature 342(6252): 877-883 (1989); Elvin A. Kabat, et al Sequences of Proteins of Immunological Interest, 5th Ed. Public Health Service, National Institutes of Health, Bethesda, Md. (1991). The constant domains of the antibody are not involved directly in binding an antibody to an antigen, but exhibit various effector functions, such as participation of the antibody in antibody dependent cellular cytotoxicity.

"Selective binding" or "specific binding" as used herein includes binding properties such as, e.g., binding affinity, binding specificity, and binding avidity; see, e.g., David J. King, Applications and Engineering of Monoclonal Antibodies, pp. 240 (1998). Binding affinity refers to the length of time the antibody resides at its epitope binding site, and can be viewed as the strength with which an antibody binds its epitope. Binding affinity can be described an antibody's equilibrium dissociation constant (KD), which is defined as the ratio Kd/Ka at equilibrium. Ka is the antibody's association rate constant and Kd is the antibody's dissociation rate constant. Binding affinity is determined by both the association and the dissociation and alone neither high association nor low dissociation can ensure high affinity. The association rate constant (Ka), or on-rate constant (Kon), measures the number of binding events per unit time, or the propensity of the antibody and the antigen to associate reversibly into its antibody-antigen complex. The association rate constant is expressed in $M^{-1}$ $s^{-1}$, and is symbolized as follows: [Ab]×[Ag]×Kon. The larger the association rate constant, the more rapidly the antibody binds to its antigen, or the higher the binding affinity between antibody and antigen. The dissociation rate constant (Kd), or off-rate constant (Koff), measures the number of dissociation events per unit time propensity of an antibody-antigen complex to separate (dissociate) reversibly into its component molecules, namely the antibody and the antigen. The dissociation rate constant is expressed in $s^{-1}$, and is symbolized as follows: [Ab+Ag]×Koff. The smaller the dissociation rate constant, the more tightly bound the antibody is to its antigen, or the higher the binding affinity between antibody and antigen. The equilibrium dissociation constant (KD) measures the rate at which new antibody-antigen complexes formed equals the rate at which antibody-antigen complexes dissociate at equilibrium. The equilibrium dissociation constant is expressed in M, and is defined as Koff/Kon=[Ab]×[Ag]/[Ab+Ag], where [Ab] is the molar concentration of the antibody, [Ag] is the molar concentration of the antigen, and [Ab+Ag] is the of molar concentration of the antibody-antigen complex, where all concentrations are of such components when the system is at equilibrium. The smaller the equilibrium dissociation constant, the more tightly bound the antibody is to its antigen, or the higher the binding affinity between antibody and antigen. Thus, in one aspect of the method of the invention, the first capture antibody specifically binding to the non-cleaved and Neurotoxin-cleaved substrate can have an association rate constant of, e.g., less than $1\times10^5$ $M^{-1}$ $s^{-1}$, less than $1\times10^6$ $M^{-1}$ $s^{-1}$, less than $1\times10^7$ $M^{-1}$ $s^{-1}$ or less than $1\times10^8$ $M^{-1}$ $s^{-1}$. In another aspect, the first capture antibody specifically binding to the non-cleaved and Neurotoxin-cleaved substrate can have an association rate constant of, e.g., more than $1\times10^5$ $M^{-1}$ $s^{-1}$, more than $1\times10^6$ $M^{-1}$ $s^{-1}$, more than $1\times10^7$ $M^{-1}$ $s^{-1}$ or more than $1\times10^8$ $M^{-1}$ $s^{-1}$. In a further aspect, the first capture antibody specifically binding to the non-cleaved and Neurotoxin-cleaved substrate can have a disassociation rate constant of, e.g., less than $1\times10^{-3}$ $M^{-1}$ $s^{-1}$, less than $1\times10^{-4}$ $M^{-1}$ $s^{-1}$, less than $1\times10^{-5}$ $M^1$ $s^{-1}$ or less than $1\times10^{-6}$ $M^{-1}$ $s^{-1}$. In a still further aspect, the first capture antibody specifically binding to the non-cleaved and Neurotoxin-cleaved substrate can have a disassociation rate constant of, e.g., more than $1\times10^{-3}$ $M^{-1}$ $s^{-1}$, more than $1\times10^{-4}$ $M^{-1}$ $s^{-1}$, more than $1\times10^{-5}$ $M^{-1}$ $s^{-1}$ or more than $1\times10^{-6}$ $M^{-1}$ $s^{-1}$. In a further aspect, the second capture antibody specifically binding to the specifically binding to the cleavage site of the Neurotoxin-cleaved substrate can have an association rate constant of, e.g., less than $1\times10^5$ $M^{-1}$ $s^{-1}$, less than $1\times10^6$ $M^{-1}$ $s^{-1}$, less than $1\times10^7$ $M^{-1}$ $s^{-1}$ or less than $1\times10^8$ $M^{-1}$ $s^{-1}$. In another aspect, the second capture antibody specifically binding to the specifically binding to the cleavage site of the Neurotoxin-cleaved substrate can have an association rate constant of, e.g., more than $1\times10^5$ $M^{-1}$ $s^{-1}$, more than $1\times10^6$ $M^{-1}$ $s^{-1}$ more than $1\times10^7$ $M^{-1}$ $s^{-1}$ or more than $1\times10^8$ $M^{-1}$ $s^{-1}$. In a further aspect, the second capture antibody specifically binding to the specifically binding to the cleavage site of the Neurotoxin-cleaved substrate can have a disassociation rate constant of, e.g., less than $1\times10^{-3}$ $M^{-1}$ $s^{-1}$, less than $1\times10^{-4}$ $M^{-1}$ $s^{-1}$, less than $1\times10^{-5}$ $M^{-1}$ $s^{-1}$ or less than $1\times10^{-6}$ $M^{-1}$ $s^{-1}$. In a still further aspect, the second capture antibody specifically binding to the specifically binding to the cleavage site of the Neurotoxin-cleaved substrate can have a disassociation rate constant of, e.g., more than $1\times10^{-3}$ $M^{-1}$ $s^{-1}$, more than $1\times10^{-4}$ $M^{-1}$ $s^{-1}$, more than $1\times10^{-5}$ $M^{-1}$ $s^{-1}$ or more than $1\times10^{-6}$ $M^{-1}$ $s^{-1}$.

A target antigen such as the Neurotoxin-cleaved or non-cleaved Neurotoxin substrates SNAP-25, VAMP/Synaptobrevin, or Syntaxin generally has one or more binding sites, also called epitopes, which are recognized by the CDR-formed antigen-binding site of the antibody. As used herein, an "epitope" is synonymous with "antigenic determinant" and refers to the site on a target antigen, such as, e.g., a peptide, polypeptide, polysaccharide or lipid-containing molecule, capable of specific binding to an immunoglobulin or T-cell receptor or otherwise interacting with a molecule. Each antibody that specifically binds to a different epitope has a different structure. Thus, one antigen may have more than one corresponding antibody. "Specific binding" as referred to herein can be tested by various well known techniques including, e.g., competition experiments and Western blots. An epitope as used in accordance with the invention relates to the antigenic determinant in the Neurotoxin substrates, e.g. SNAP-25, VAMP/Synaptobrevin, or Syntaxin which is recognized by the antibody. As used herein, the term "specifically" means selectively and refers to having a unique effect or influence or reacting in only one way or with only one thing. As used herein, the term "specifically binds" or "selectively binds" when made in reference to an antibody or binding protein or binding domain, refers to the discriminatory binding of the antibody or binding protein/domain to the indicated target epitope such that the antibody or binding protein/domain does not substantially cross react with non-target epitopes. The minimal size of a peptide epitope, as defined herein, is about five amino acid residues, and a peptide epitope typically comprises at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 30 amino acid residues. A peptide epitope may be a linear or a discontinuous epitope. A discontinuous epitope comprises amino acid residues that are not adjacent in the primary structure of the peptide but are brought together into an epitope by way of the secondary, tertiary or quaternary structure of the peptide. Furthermore, it is also noted that an epitope may comprise a portion of a molecule other than an amino acid sequence such as, e.g., carbohydrate moiety, lipid moiety like glycolipids or lipoproteins, or a chemically modified amino acid moiety like a phosphorylated amino acid.

According to the method of the present invention, the "first capture antibody" specifically binds to an epitope comprised by the non-cleaved and Neurotoxin-cleaved substrate. Said Neurotoxin substrates can be, for example, SNAP-25, VAMP/Synaptobrevin, or Syntaxin. For instance, SNAP-25 is a known substrate of BoNT/A, BoNT/C1 and BoNT/E. VAMP/Synaptobrevin is a substrate of BoNT/B, BoNT/D, BoNT/F, BoNT/G and TeNT, whereas Syntaxin is a substrate of BoNT/C1. Said first capture antibody allows for the determination of the total amount, i.e. complete content of the respective Neurotoxin substrate in the cells. For example, in SNAP-25, having a total length of 205 amino acid residues, the cleavage site for BoNT/A is localized between amino acid residues Gln 197 and Arg 198. Accordingly, an antibody specifically binding to an epitope positioned N-terminally to the BoNT/A cleavage site, i.e. an epitope localized between amino acid residues 1 and 198 of SNAP-25 can be used as first capture antibody. For example, said antibody can specifically bind to an N-terminal epitope or an epitope positioned in the mid-part of SNAP-25. For BoNT/C1, an epitope positioned N-terminally to the BoNT/C1 cleavage site (Arg 198-Ala 199), i.e. between amino acid residues 1 and 199 of SNAP-25 can be used as first capture antibody. For BoNT/E, an epitope positioned N-terminally to the BoNT/E cleavage site (Arg 180-Ile 181), i.e. between amino acid residues 1 and 181 of SNAP-25 can be used as first capture antibody. If VAMP is used as a Neurotoxin substrate, an epitope positioned N-terminally to the BoNT/B cleavage site (Gln 76-Phe 77), i.e. between amino acid residues 1 and 77 of VAMP can be used as first capture antibody. An epitope positioned N-terminally to the BoNT/D cleavage site (Lys 59-Leu 60), i.e. between amino acid residues 1 and 60 of VAMP2 can be used as first capture antibody. An epitope positioned N-terminally to the BoNT/F cleavage site (Gln 58-Lys 59), i.e. between amino acid residues 1 and 59 of VAMP2 can be used as first capture antibody. An epitope positioned N-terminally to the BoN/G cleavage site (Ala 81-Ala 82), i.e. between amino acid residues 1 and 82 of VAMP2 can be used as first capture antibody. If Syntaxin is used as a substrate, an epitope positioned N-terminally to the BoN/C1 cleavage site (Lys 253-Ala 254), i.e. between amino acid residues 1 and 254 of Syntaxin 1a can be used as first capture antibody.

A neurotoxin cleavage site recognized and cleaved by the BoNT/A protease, in an aspect of the invention, is derived from a protein that is sensitive to cleavage by BoNT/A. In an aspect, such a protein is human SNAP-25A or SNAP-25B or a homolog, paralog or ortholog thereof from rat, mouse, bovine, *Danio, Carassius, Xenopus, Torpedo, Strongylocentrotus, Loligo, Lymnaea* or *Aplysia*. Suitable cleavage sites derived from said proteins are disclosed, e.g., in EP 1 926 744 B1.

A neurotoxin cleavage site recognized and cleaved by the BoNT/B protease, in an aspect of the invention, is derived from a protein that is sensitive to cleavage by BoNT/B. In an aspect, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

A neurotoxin cleavage site recognized and cleaved by the BoNT/C1 protease, in an aspect of the invention, is derived from a protein that is sensitive to cleavage by BoNT/C1. In an aspect, such a protein is human and mouse Syntaxin 1A, Syntaxin 1B1, Syntaxin 2-1, Syntaxin 2-2, Syntaxin 2-3, Syntaxin 3A or Syntaxin 1B2, bovine or rat Syntaxin 1A, Syntaxin 1B1 or Syntaxin 1B2, rat Syntaxin 2 or Rat syntaxin 3, mouse Syntaxin 1A, Syntaxin 1B1, Syntaxin 1B2, Syntaxin 2, Syntaxin 3A, Syntaxin 3B or Syntaxin 3C, chicken Syntaxin 1A or Syntaxin 2; *Xenopus* Syntaxin 1A or Syntaxin 1B, *Danio* Syntaxin 1A, Syntaxin 1B or Syntaxin 3, *Torpedo* Syntaxin 1A or Syntaxin 1B, *Strongylocentrotus* Syntaxin 1A or Syntaxin 1B, *Drosophila* Syntaxin 1A or Syntaxin 1B, *Hirudo* Syntaxin 1A or Syntaxin 1B, *Loligo* Syntaxin 1A or Syntaxin 1B, *Lymnaea* Syntaxin 1A or Syntaxin 1B or any ortholog, paralog or homolog thereof. Suitable cleavage sites derived from said proteins are disclosed in EP 1 926 744 B1.

A neurotoxin cleavage site recognized and cleaved by the BoNT/D protease, in an aspect of the invention, is derived from a protein that is sensitive to cleavage by BoNT/D. In an aspect, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

A neurotoxin cleavage site recognized and cleaved by the BoNT/E protease, in an aspect of the invention, is derived from a protein that is sensitive to cleavage by BoNT/E. In an aspect, such a protein is, such a protein is human SNAP-25A or B or a homolog, paralog or ortholog thereof from rat, mouse, bovine, *Danio, Carassius, Xenopus, Torpedo, Strongylocentrotus, Loligo, Lymnaea* or *Aplysia*. Suitable cleavage sites derived from said proteins are disclosed in EP 1 926 744 B1.

A neurotoxin cleavage site recognized and cleaved by the BoNT/F protease, in an aspect of the invention, is derived from a protein that is sensitive to cleavage by BoNT/F. In an aspect, such a protein is, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

A neurotoxin cleavage site recognized and cleaved by the BoNT/G protease, in an aspect of the invention, is derived from a protein that is sensitive to cleavage by BoNT/G. In an aspect, such a protein is, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

A neurotoxin cleavage site recognized and cleaved by the TeNT protease, in an aspect of the invention, is derived from a protein that is sensitive to cleavage by TeNT. In an aspect, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

Examples for appropriate antibodies which can be used as first capture antibodies in the method of the invention include, for example, the rabbit polyclonal anti-SNAP-25 antibody 59684 (Sigma) (Fernandez-Salas E, Wang J, Molina Y, Nelson J B, Jacky B P S, et al. (2012) Botulinum Neurotoxin Serotype a Specific Cell-Based Potency Assay to Replace the Mouse Bioassay. PLoS ONE 7(11): e49516. doi:10.1371/journal.pone.0049516), the rabbit polyclonal anti-SNAP25 antibody PA5-19708 (Pierce Antibodies), the rabbit polyclonal anti-SNAP25 antibody PA5-19701 (Pierce Antibodies), the VAMP/Synaptobrevin antibody sc-13992 (Santa Cruz Biotechnology) or #104 203 (Synaptic Systems), or the Syntaxin antibody ADI-VAM-SV013 (Enzo Life Sciences).

In one aspect, the first capture antibody that recognizes the non-cleaved and Neurotoxin-cleaved substrate in order to determine the total amount of Neurotoxin substrate in the cell is used for normalization, as shown in the following Examples.

The "second capture antibody" as used herein specifically binds to the cleavage site of the Neurotoxin-cleaved substrate. Accordingly, said second capture antibody recognizes selectively the Neurotoxin substrate cleaved by the Neurotoxin, for example, the BoNT/A SNAP-25-cleaved product. In contrast, said second capture antibody is not able to bind to the non-cleaved Neurotoxin substrate, such as, e.g., non-cleaved SNAP-25. Examples for appropriate antibodies which can be used as second capture antibodies in the method of the invention include, for example, the mouse monoclonal antibodies of the invention as indicated below, the mouse monoclonal antibody MC-6053 (R&D Systems) which recognizes the BoNT/A-cleaved SNAP-25 (Baldwin and Barbieri 2007, Biochemistry 46, 3200-3210), as well as the mouse monoclonal antibody DMAB4345 (Creative Diagnostics).

The present invention provides in a further aspect, novel monoclonal antibodies specifically binding to the cleavage site of the Neurotoxin-cleaved SNAP-25, i.e. to Neurotoxin-cleaved SNAP-25 only, whereas they do not bind to non-cleaved SNAP-25. Said monoclonal antibodies have been generated and characterized as described in the following Examples and have been found particularly suitable as second capture antibodies for the method of the invention, due to their high affinity and specificity for Neurotoxin-cleaved SNAP-25. Preferably, the monoclonal antibodies of the invention recognize and specifically bind to the epitope SNAP-25$_{190-197}$ "TRIDEANQ" shown in SEQ ID NO: 74 and/or to SNAP-25$_{197}$, i.e. Neurotoxin (e.g., BoNT/A)-cleaved SNAP-25. More preferably, the monoclonal antibodies of the invention recognize and specifically bind to the epitope SNAP-25$_{191-197}$ "RIDEANQ" shown in SEQ ID NO: 75 and/or to SNAP-25$_{197}$, to the epitope SNAP-25$_{192-197}$ "IDEANQ" of the sequence shown in SEQ ID NO: 76 and/or to SNAP-25$_{197}$, or to the epitope SNAP-25$_{193-197}$ "DEANQ" shown in SEQ ID NO: 77 and/or to SNAP-25$_{197}$.

In one aspect, the present invention relates to an antibody or a fragment thereof, which specifically binds to the cleavage site of the BoNT/A-cleaved SNAP-25 and which comprises a heavy chain variable region (VH) comprising an amino acid sequence shown in SEQ ID NO. 18 and/or a light chain variable region (VL) comprising an amino acid sequence shown in SEQ ID NO. 19. Further encompassed by the invention are antibodies or fragments thereof which comprise one, two or three complementarity determining regions (CDRs) of said heavy chain and/or light chain variable region(s). The corresponding CDRH1, CDRH2 and CDRH3 sequences are shown in SEQ ID NOs. 20 to 22, respectively, whereas the corresponding CDRL1, CDRL2 and CDRL3 sequences are shown in SEQ ID NOs. 23 to 25, respectively. The mentioned sequences correspond to mouse monoclonal antibody 20-2-5 as shown in the following Examples. In addition, the present invention pertains to an antibody or a fragment thereof, which specifically binds to the cleavage site of the BoNT/A-cleaved SNAP-25 and which comprises a heavy chain variable region (VH) comprising an amino acid sequence shown in SEQ ID NO. 26 and/or a light chain variable region (VL) comprising an amino acid sequence shown in SEQ ID NO. 27. Further encompassed by the invention are antibodies or fragments thereof which comprise one, two or three complementarity determining regions (CDRs) of said heavy chain and/or light chain variable region(s). The corresponding CDRH1, CDRH2 and CDRH3 sequences are shown in SEQ ID NOs. 28 to 30, respectively, whereas the corresponding CDRL1, CDRL2 and CDRL3 sequences are shown in SEQ ID NOs. 31 to 33, respectively. The mentioned sequences correspond to mouse monoclonal antibody 5-10-5 as shown in the following Examples. Further, the present invention relates to an antibody or a fragment thereof, which specifically binds to the cleavage site of the BoNT/A-cleaved SNAP-25 and which comprises a heavy chain variable region (VH) comprising an amino acid sequence shown in SEQ ID NO. 34 and/or a light chain variable region (VL) comprising an amino acid sequence shown in SEQ ID NO. 35. Further encompassed by the invention are antibodies or fragments thereof which comprise one, two or three complementarity determining regions (CDRs) of said heavy chain and/or light chain variable region(s). The corresponding CDRH1, CDRH2 and CDRH3 sequences are shown in SEQ ID NOs. 36 to 38, respectively, whereas the corresponding CDRL1, CDRL2 and CDRL3 sequences are shown in SEQ ID NOs. 39 to 41, respectively. The mentioned sequences correspond to mouse monoclonal antibody 1-10-4 as shown in the following Examples. The present invention pertains also to an antibody or a fragment thereof, which specifically binds to the cleavage site of the BoNT/A-cleaved SNAP-25 and which comprises a heavy chain variable region (VH) comprising an amino acid sequence shown in SEQ ID NO. 42 and/or a light chain variable region (VL) comprising an amino acid sequence shown in SEQ ID NO. 43. Further encompassed by the invention are antibodies or fragments thereof which comprise one, two or three complementarity determining regions (CDRs) of said heavy chain and/or light chain variable region(s). The corresponding CDRH1, CDRH2 and CDRH3 sequences are shown in SEQ ID NOs. 44 to 46, respectively, whereas the corresponding CDRL1, CDRL2 and CDRL3 sequences are shown in SEQ ID NOs.

47 to 49, respectively. The mentioned sequences correspond to mouse monoclonal antibody 16-5-4 as shown in the following Examples. In addition, the present invention relates to an antibody or a fragment thereof, which specifically binds to the cleavage site of the BoNT/A-cleaved SNAP-25 and which comprises a heavy chain variable region (VH) comprising an amino acid sequence shown in SEQ ID NO. 50 and/or a light chain variable region (VL) comprising an amino acid sequence shown in SEQ ID NO. 51. Further encompassed by the invention are antibodies or fragments thereof which comprise one, two or three complementarity determining regions (CDRs) of said heavy chain and/or light chain variable region(s). The corresponding CDRH1, CDRH2 and CDRH3 sequences are shown in SEQ ID NOs. 52 to 54, respectively, whereas the corresponding CDRL1, CDRL2 and CDRL3 sequences are shown in SEQ ID NOs. 55 to 57, respectively. The mentioned sequences correspond to mouse monoclonal antibody 6-3-8 as shown in the following Examples. The present invention pertains further to an antibody or a fragment thereof, which specifically binds to the cleavage site of the BoNT/A-cleaved SNAP-25 and which comprises a heavy chain variable region (VH) comprising an amino acid sequence shown in SEQ ID NO. 58 and/or a light chain variable region (VL) comprising an amino acid sequence shown in SEQ ID NO. 59. Further encompassed by the invention are antibodies or fragments thereof which comprise one, two or three complementarity determining regions (CDRs) of said heavy chain and/or light chain variable region(s). The corresponding CDRH1, CDRH2 and CDRH3 sequences are shown in SEQ ID NOs. 60 to 62, respectively, whereas the corresponding CDRL1, CDRL2 and CDRL3 sequences are shown in SEQ ID NOs. 63 to 65, respectively. The mentioned sequences correspond to mouse monoclonal antibody 18-3-3 as shown in the following Examples. Moreover, the present invention concerns an antibody or a fragment thereof, which specifically binds to the cleavage site of the BoNT/A-cleaved SNAP-25 and which comprises a heavy chain variable region (VH) comprising an amino acid sequence shown in SEQ ID NO. 66 and/or a light chain variable region (VL) comprising an amino acid sequence shown in SEQ ID NO. 67. Further encompassed by the invention are antibodies or fragments thereof which comprise one, two or three complementarity determining regions (CDRs) of said heavy chain and/or light chain variable region(s). The corresponding CDRH1, CDRH2 and CDRH3 sequences are shown in SEQ ID NOs. 68 to 70, respectively, whereas the corresponding CDRL1, CDRL2 and CDRL3 sequences are shown in SEQ ID NOs. 71 to 73, respectively. The mentioned sequences correspond to mouse monoclonal antibody 14-12-1 as shown in the following Examples.

The term "first detection antibody" as used herein is an antibody specifically binding to the first capture antibody. Said first detection antibody allows for the specific detection of the first capture antibody. By measuring the amount of bound first detection antibody, the amount of first detection complexes can be determined since the amount of bound first detection antibody in the first detection complex correlates with the amount of first capture antibody (and accordingly the amount of total, i.e. cleaved and non-cleaved Neurotoxin substrate) comprised by the first detection complex. For example, an appropriate species-specific antibody can be used as a first detection antibody: If a mouse antibody has been used as a first capture antibody, said first detection antibody can be an anti-mouse antibody specifically binding to the mouse antibody. The first detection antibody can be, for instance, an alkaline phosphatase (AP)-conjugated antibody, a horseradish-peroxidase (HRP)-conjugated antibody or an antibody conjugated to a fluorescence dye. Conjugation of enzymes to antibodies, for example, by using glutaraldehyde is well known in the art.

Enzyme linked immunosorbent assays (ELISA) have been used to quantitate a wide range of compounds and pathogens for almost 40 years. Initially, radioactivity was used to quantitate the assays, but radioimmunoassays (RIA) have been replaced with assays utilizing enzymes to obtain colorimetric results. Recently new substrates have been developed to produce fluorescent and luminescent products. The basic tenet of the new assays remains the same as colorimetric assays. The substrate is converted into a measurable compound by the enzymatic activity of proteins conjugated to an antibody, which confers specificity.

Commonly used enzyme conjugates in ELISA are alkaline phosphatase or horseradish peroxidase. Accordingly, in one aspect, the first detection antibody can be, for instance, conjugated to alkaline phosphatase or horseradish peroxidase. Further examples of enzyme conjugates which can be used as a first detection antibody in the method of the invention include glucose oxidase which uses glucose as substrate, tyrosinase which converts the substrate 1-(4-Methyl-coumarin-7-yl)-3-(4-hydroxyphenyl)urea) (PAP-AMC) (Stratis Avrameas, Immunochemistry, Volume 6, Issue 1, January 1969, Pages 43-48, IN9-IN11, 49-52) or β-galactosidase which converts the substrate 6,8-difluoro-4-methylumbelliferyl β-d-galactopyranoside (DiFMUG) (Gee et al., Analytical Biochemistry, Volume 273, Issue 1, August 1999, pages 41-48). Upon addition of a substrate, said substrate is converted by the enzyme to a detectable form. For example, alkaline phosphatase catalyzes the cleavage of esters of phosphoric acid. If an alkaline phosphatase (AP)-conjugated antibody is used as a first detection antibody, an appropriate substrate such as a 4-methylumbelliferyl phosphate derivative, e.g., 6,8-Difluoro-4-methylumbelliferyl phosphate (DiFMUP), or fluorescein diphosphate (FDP). 6,8-difluoro-4-methylumbelliferyl phosphate (DiFMUP) is converted by the AP to a detectable form, i.e. the fluorogenic product 6,8-difluoro-4-methylumbelliferone. Said substrate is provided, e.g., by Molecular Probes. Fluorescence intensities of this reaction product of DiFMUP can be measured using excitation/emission maxima of about 358/450 nm. Further substrates which can be used for this purpose are 9H-(1,3-dichloro-9,9-dimethylacridin-2-one-7-yl) phosphate (DDAO-phosphate; Invitrogen), fluorescein diphosphate (FDP; Sigma Aldrich) or 4-methylumbelliferyl phosphate (MUP; Invitrogen). DDAO-phosphate is converted by the AP to the fluorogenic product dimethylacridinone (DDAO), having an excitation/emission maxima of about 646/659 nm. If FDP is used as substrate for the AP, the reaction product is fluorescein, having an excitation/emission maximum of about 490/514 nm. For MUP, the corresponding reaction product is 4-methylumbelliferone (7-hydroxy-4-methylcoumarin), having an excitation/emission maxima of about 360/449 nm. Also these substrates are commercially available, e.g. from Molecular Probes. Alternatively, horseradish peroxidase can be used as enzyme conjugate in the first detection antibody of the method of the invention. Horseradish peroxidase (HRP) catalyzes the reduction of hydrogen peroxide ($H_2O_2$) to water ($H_2O$). In the presence of specific substrates, which act as hydrogen donors, the action of HRP converts colorless or non-fluorescent molecules into colored and/or fluorescent moieties respectively. For instance, Amplex® Red (Life Technologies) is a substrate for use with HRP containing assays. Amplex Red, in the presence of peroxidase enzyme, reacts with $H_2O_2$ in a 1:1 stoichiometry to produce resorufin, a red fluorescent compound which has an absorption and fluorescence emission maxima of 563 nm and 587 nm, respectively. Another example for a HRP substrate is Amplex® UltraRed (Life Technologies). It has been reported that Amplex® UltraRed reagent (excitation/emission of ~570/585 nm) improves upon the performance of the Amplex® Red reagent, offering brighter fluorescence and enhanced sensitivity on a per-mole basis in horseradish peroxidase or horseradish peroxidase-coupled enzyme assays. Fluorescence of the oxidized Amplex® UltraRed reagent (Amplex® UltroxRed reagent) is also less sensitive to pH, and the substrate and its oxidation product exhibit greater stability that the Amplex® Red reagent in the presence of hydrogen peroxide ($H_2O_2$) or thiols such as dithiothreitol (DTT). Further appropriate HRP substrates which can be used in the method of the invention include, e.g., 10-Acetyl-3,7-Dihydroxyphenoxazine (ADHP; AnaSpec) or 3-(4-Hydroxyphenyl) propionic acid (HPPA; AnaSpec) (Tuuminen et al. 1991, J. Immunoassay 12, 29-46).

Alternatively, the first detection antibody can carry an appropriate, detectable label which allows for the detection of the first capture antibody. Labeling may be done by direct or indirect methods. Direct labeling involves binding of the label directly (covalently or non-covalently) to the first detection antibody. Indirect labeling involves binding (covalently or non-covalently) of an agent which specifically binds to the first detection antibody and which carries a detectable label. Such an agent may be, e.g., a secondary (higher order) antibody which specifically binds to the first detection antibody. The secondary antibody in such a case will be coupled to a detectable label. It will be understood that further higher order antibodies can be used in addition for detection of the first detection complex. The higher order antibodies are often used to increase the signal. Suitable higher order antibodies may also include the well-known streptavidin-biotin system (Vector Laboratories, Inc.), and the well-known Dako LSAB™2 and LSAB™+ (labeled streptavidin-biotin), or Dako PAP (Peroxidase Anti-Peroxidase). In a further aspect, the said label of the first detection antibody is a fluorescent dye, i.e. the first antibody is conjugated to a fluorescent dye. In this case, the fluorescence can be directly measured by a fluorescence reader. Typical fluorescent labels include fluorescent proteins such as GFP and its derivatives, Cy dyes such as Cy3, or Cy5, Texas Red, Fluorescein, and the Alexa dyes, e.g. Alexa 568.

The "second detection antibody" as used herein is an antibody specifically binding to the second capture antibody. The second detection antibody can be, for instance, conjugated to an enzyme such as alkaline phosphatase, horseradish peroxidase, glucose oxidase or tyrosinase. Accordingly, in one aspect, the second detection antibody is an alkaline phosphatase (AP)-conjugated antibody, a horseradish-peroxidase (HRP)-conjugated antibody, an glucose oxidase-conjugated antibody or a tyrosinase-conjugated antibody. Said second detection antibody allows for the specific detection of the second capture antibody. By measuring the amount of bound second detection antibody, the amount of second detection complexes can be determined since the amount of bound second detection antibody in the second detection complex correlates with the amount of second capture antibody (and accordingly the amount of cleaved Neurotoxin substrate) comprised by the first detection complex. For example, if a rabbit antibody has been used as a second capture antibody, an anti-rabbit antibody can be used as a second detection antibody. The second detection antibody can carry an enzyme as set forth above or a label such as a fluorescent dye (i.e. the second detection antibody is conjugated to a fluorescent dye) as mentioned elsewhere herein with respect to the first detection antibody. In one aspect of the method of the invention, the enzyme conjugated to the first detection antibody differs from the enzyme conjugated to the second detection antibody in order to allow the specific detection of the respective first and second capture antibody in the method of the invention. For instance, if the first detection antibody is an AP-conjugated antibody, the second detection antibody can be a horseradish peroxidase (HRP)-conjugated antibody or vice versa. Further, the excitation/emission spectra of the fluorogenic substrates of the AP and HRP do not substantially overlap but differ from each other, i.e. they show a clear shift so as to allow the distinction of the fluorescence intensities generated by the respective product. For example, DiFMUP exhibits excitation/emission at ~358/450 nm, whereas Amplex UltraRed exhibits excitation/emission of ~570/585 nm, thereby allowing for accurate measurements of the fluorescence intensities generated by the conversion of said fluorogenic substrates by the respective enzyme. In a further aspect, the alkaline phosphatase (AP)-conjugated antibody is used as a first detection antibody for the antigen which is present in excess in the cell, i.e. for the measurement of the amount of the total (non-cleaved and cleaved) Neurotoxin substrate, such as total SNAP-25, in the cell. The horseradish peroxidase (HRP)-conjugated antibody is used as a second detection antibody for the antigen which is present in the cell in a lower amount, i.e. for the measurement of the amount of the cleaved Neurotoxin substrate, such as BoNT/A cleaved SNAP-25, in the cell. As known in the art, HRP substrates are more sensitive than AP substrates meaning that lower amounts of analytes can be detected. If an HRP antibody is used as secondary antibody for the detection of cleaved SNAP-25, lower amounts of cleaved SNAP-25 are detectable. In turn, lower amounts of BoNT/A can be determined, thereby increasing the sensitivity of the assay. Because the AP antibody measures the total amount of SNAP-25 in the cell, high sensitivity for the substrate is not required, due to the excess of analyte.

The term "at least" as used herein such as, for example, "at least a first capture antibody" means that in addition to an antibody specifically binding to the non-cleaved and Neurotoxin-cleaved substrate, one or more further antibodies with the mentioned specificity can be used in the method of the invention. Similarly, "at least a second capture antibody" means that in addition to an antibody specifically binding to the cleavage site of the Neurotoxin-cleaved substrate, one or more further antibodies with the mentioned specificity can be used in the method of the invention. Further, one or more first detection antibodies specifically binding to the first detection antibody (or first detection antibodies) can be used in the method of the invention. Similarly, one or more second detection antibodies specifically binding to the second detection antibody (or second detection antibodies) can be used in the method of the invention.

The term "first detection complex" refers to a complex comprising a first capture antibody and a first detection antibody which specifically binds to the non-cleaved and Neurotoxin-cleaved substrate, thereby allowing for the determination of the total content of Neurotoxin substrate in the cell. The amount of first detection complex can be measured by determination of the amount of specifically bound first detection antibody. This can be achieved dependent on the nature of the enzyme or the label of the first detection antibody, e.g. by measuring the intensity of fluorescence.

The term "second detection complex" refers to a complex comprising the second capture antibody and the second detection antibody which specifically binds to the cleavage site of the Neurotoxin-cleaved substrate, thereby allowing for the determination of the content of cleaved Neurotoxin substrate in the cell. The amount of second detection complex can be measured by determination of the amount of specifically bound second detection antibody. This can be achieved dependent on the nature of the enzyme or the label of the second detection antibody, e.g. by measuring the intensity of fluorescence.

It is envisioned that instead of enzyme-linked immunosorbent analysis (ELISA), any detection system can be used to practice aspects of the method of the invention, with the provision that the signal to noise ratio can distinguish to a statistically significant degree the signal from the formed antibody-antigen complexes from the background signal. Non-limiting examples of immuno-based detection systems include immunoblot analysis, like Western blotting and dot-blotting, immunoprecipitation analysis, and sandwich ELISA. The detection of the signal can be achieved using autoradiography with imaging or phosphorimaging (AU), bioluminescence (BL), fluorescence, resonance energy transfer, plane polarization, colormetric, or flow cytometry (FC). Descriptions of immuno-based detection systems are disclosed, for example, in Commonly Used Techniques in Molecular Cloning, pp. A8.1-A8-55 (Sambrook & Russell, eds., Molecular Cloning A Laboratory Manual, Vol. 3, 3.sup.rd ed. 2001); Detection Systems, pp. A9.1-A9-49 (Sambrook & Russell, eds., Molecular Cloning A Laboratory Manual, Vol. 3, 3.sup.rd ed. 2001).

In a further aspect, the cells, antibodies, Neurotoxin polypeptides and Neurotoxin substrates or any other product as referred to herein are isolated cells, antibodies, Neurotoxin polypeptides, Neurotoxin substrates or products, respectively. As used herein, the term "isolated" such as an isolated antibody refers to a molecule separated from its natural environment by the use of human intervention.

In one aspect of the method of the invention, the method is a fluorescence method.

In another aspect of the method of the invention, the Neurotoxin polypeptide is a BoNT/A, BoNT/B, BoNT/C1, BoNT/D, BoNT/E, BoNT/F or BoNT/G polypeptide or a Tetanus (TeNT) Neurotoxin polypeptide, as defined in detail elsewhere herein.

In a further aspect of the method of the invention, the Neurotoxin substrate is VAMP/Synaptobrevin, SNAP-25 or Syntaxin.

In the following, the corresponding accession number of the respective Neurotoxin substrate which can be used in the method of the invention is indicated: human SNAP-25 P60880, human Syntaxin-1A Q16623, Syntaxin-1B P61266, Syntaxin-2 P32856, Syntaxin-3 Q13277, Syntaxin-4 Q12846, Syntaxin-5 Q13190, Syntaxin-6 O43752, Syntaxin-7 O15400, Syntaxin-8 Q9UNK0, Syntaxin-10 O60499, Syntaxin-11 O75558, Syntaxin-12 Q86Y82, Syntaxin-16 O14662, Syntaxin-17 P56962, Syntaxin-18 Q9P2W9, Syntaxin-19 Q8N4C7; human Synaptobrevin-1 P23763, Synaptobrevin-2 P63027, Synaptobrevin-3 Q15836; human synaptogmin: Synaptotagmin-1 P21579, Synaptotagmin-2 Q8N9I0, Synaptotagmin-3 Q9BQG1, Synaptotagmin-4 Q9H2B2, Synaptotagmin-5 O00445, Synaptotagmin-6 Q5T7P8, Synaptotagmin-8 Q8NBV8, Synaptotagmin-9 Q86SS6, Synaptotagmin-10 Q6XYQ8, Synaptotagmin-11 Q9BT88, Synaptotagmin-12 Q8IV01, Synaptotagmin-13 Q7L8C5, Synaptotagmin-14 Q8NB59, Synaptotagmin-15 Q9BQS2, Synaptotagmin-16 Q17RD7, Synaptotagmin-17 Q9BSW7, human vesicle associated membrane proteins (VAMPs): Vesicle-associated membrane protein 1 P23763, Vesicle-associated membrane protein 2 P63027, Vesicle-associated membrane protein 3 Q15836, Vesicle-associated membrane protein 4 O75379, Vesicle-associated membrane protein 5 O95183, Vesicle-associated membrane protein 7 P51809, Vesicle-associated membrane protein 8 Q9BV40; of synaptic vesicle glycoproteins (SV2): Synaptic vesicle glycoprotein 2A Q7L0J3, Synaptic vesicle glycoprotein 2B Q7L1I2, Synaptic vesicle glycoprotein 2C.

In another aspect of the invention, the cells are neuronal cells or neuronal differentiated cells selected from the group consisting of: primary neuronal cells, tumor cells which are capable of differentiating to neuronal cells such as neuroblastoma cells or cell lines as defined elsewhere herein, P19 cells or induced pluripotent stem cell (iPS)-derived neurons, preferably human induced pluripotent stem cell (iPS)-derived neurons.

In a further aspect of the method of the invention, fixing the cells is carried out by the addition of a fixation agent selected from the group consisting of: methanol, ethanol, acetone, formaldehyde or mixtures thereof. Preferably, fixing the cells is carried out by addition of ice-cold methanol (−20° C.) and incubation for about 20 minutes at −20° C.

In one aspect of the method of the invention, the first capture antibody specifically binding to the non-cleaved and Neurotoxin-cleaved substrate allows for the determination of the total amount of the Neurotoxin substrate in the cells. Suitable binding regions and epitopes of the first capture antibody within the respective Neurotoxin substrate(s) have been defined elsewhere herein.

In specific aspects of the method of the invention, the first capture antibody specifically binding to the non-cleaved and Neurotoxin-cleaved substrate is the rabbit polyclonal anti-SNAP-25 antibody S9684, the rabbit polyclonal anti-SNAP25 antibody PA5-19708 (Pierce Antibodies), or the rabbit polyclonal anti-SNAP25 antibody PA5-19701 (Pierce Antibodies).

In further aspects of the method of the invention, the second capture antibody is the mouse monoclonal antibody 20-2-5, 5-10-5, 1-10-4, 16-5-4, 6-3-8, 18-3-3, or 14-12-1 of the invention, or the mouse monoclonal antibody clone MC-6053 (R&D Systems). Preferably, the second capture antibody is the mouse monoclonal antibody 20-2-5. The corresponding sequences of the variable regions and the CDRs of the mouse monoclonal antibodies of the invention have been described elsewhere herein.

In specific aspects of the method of the invention, the first and/or second capture antibody is/are immobilized. For example, said first and/or second capture antibody is/are linked to a solid phase support. As used herein, the term "solid-phase support" is synonymous with "solid phase" and refers to any matrix that can be used for immobilizing a first and/or second capture antibody disclosed in the present specification. Non-limiting examples of solid phase supports include, e.g., a tube; a plate; a column; pins or "dipsticks"; a magnetic particle, a bead or other spherical or fibrous chromatographic media, such as, e.g., agarose, sepharose, silica and plastic; and sheets or membranes, such as, e.g., nitrocellulose and polyvinylidene fluoride (PVDF). The solid phase support can be constructed using a wide variety of materials such as, e.g., glass, carbon, polystyrene, polyvinylchloride, polypropylene, polyethylene, dextran, nylon, diazocellulose, or starch. The solid phase support selected can have a physical property that renders it readily separable from soluble or unbound material and generally allows unbound materials, such as, e.g., excess reagents, reaction by-products, or solvents, to be separated or otherwise removed (by, e.g., washing, filtration, centrifugation, etc.) from solid phase support-bound assay component. Non-limiting examples of how to make and use a solid phase supports are described in, e.g., Molecular Cloning, A Laboratory Manual, supra, (2001); and Current Protocols in Molecular Biology, supra, (2004), each of which is hereby incorporated by reference in its entirety. In one aspect, the first and/or second capture antibody is conjugated to beads. It is envisaged that the antibody-bead conjugates are small enough to be able to enter the cells through the pores caused by the permeabilization of said cells.

In specific aspects of the method of the invention, the first detection antibody is an alkaline phosphatase (AP)-conjugated antibody, a horseradish-peroxidase (HRP)-conjugated antibody or an antibody conjugated to a fluorescence dye.

In further specific aspects of the method of the invention, the second detection antibody is an alkaline phosphatase (AP)-conjugated antibody, a horseradish-peroxidase (HRP)-conjugated antibody, a glucose oxidase-conjugated antibody, a tyrosinase-conjugated antibody or a β-Galactosidase-conjugated antibody.

Preferably, the alkaline phosphatase (AP)-conjugated antibody is used as a first detection antibody for the measurement of the amount of the total (non-cleaved and cleaved) Neurotoxin substrate, such as total SNAP-25, in the cell; and the horseradish peroxidase (HRP)-conjugated antibody is used as a second detection antibody for the measurement of the amount of the cleaved Neurotoxin substrate, such as BoNT/A cleaved SNAP-25, in the cell.

In certain aspects of the method of the invention, the AP substrate is a 4-methylumbelliferryl phosphate derivative such as 6,8-Difluoro-4-methylumbelliferyl phosphate (DiFMUP), or fluorescein diphosphate (FDP).

In specific aspects of the method of the invention, the HRP substrate is Amplex UltraRed, 10-Acetyl-3,7-Dihydroxyphenoxazine (ADHP) or 3-(4-Hydroxyphenyl) propionic acid (HPPA).

In a more specific aspect of the method of the invention, the method is carried out as illustrated in FIG. 1.

The invention in a further aspect relates to a kit for carrying out the method of the invention comprising:
a) an arrangement of a first capture antibody, a second capture antibody, a first detection antibody and a second detection antibody, wherein said arrangement allows for carrying out the method of the invention;
b) means for calculating the amount of substrate cleaved by said Neurotoxin based on the amounts of the first and second detection complexes determined by the arrangement according to a); and
c) instructions for carrying out said method.

The term "kit" as used herein refers to a collection of the aforementioned means or reagents of the present invention which may or may not be packaged together. The components of the kit may be comprised by separate vials (i.e. as a kit of separate parts) or provided in a single vial. Moreover, it is to be understood that the kit of the present invention is to be used for practicing the methods referred to herein above. In one aspect, it is envisaged that all components are provided in a ready-to-use manner for practicing the method referred to herein. In a further aspect, the kit contains instructions for carrying out the said method. The instructions can be provided by a user manual in paper- or electronic form. For example, the manual may comprise instructions for interpreting the results obtained when carrying out the aforementioned methods using the kit of the present invention.

Finally, the invention relates in another aspect to a method for manufacture of a formulated Neurotoxin product for use in pharmaceutical or cosmetic applications, comprising (i) determining the biological activity of a Neurotoxin product by the method of the invention and (ii) formulating the Neurotoxin product for use in pharmaceutical or cosmetic applications. The Neurotoxin product can be formulated by various techniques dependent on the desired application purposes which are known in the art. For example, the (biologically active) Neurotoxin product can be used in combination with one or more pharmaceutically acceptable carriers as a pharmaceutical composition. The pharmaceutically acceptable carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatine, agar, pectin, acacia, magnesium stearate, stearic acid and the like. Exemplary of liquid carriers are glycerol, phosphate buffered saline solution, water, emulsions, various types of wetting agents, and the like. Suitable carriers comprise those mentioned above and others well known in the art, see, e.g., Remington's Pharmaceutical Sciences, Mack Publishing Company, Easton, Pennsylvania. In an aspect, the pharmaceutical composition can be dissolved in a diluent, prior to administration. The diluent is also selected so as not to affect the biological activity of the Neurotoxin product. Examples of such diluents are distilled water or physiological saline. In addition, the pharmaceutical composition or formulation may also include other carriers or non-toxic, non-therapeutic, non-immunogenic stabilizers and the like. Thus, the formulated Neurotoxin product can be present, in an aspect, in liquid or lyophilized form. In an aspect, it can be present together with glycerol, protein stabilizers (HSA) or non-protein stabilizers such as polyvinyl pyrrolidone (PVP), hyaluronic acid or free amino acids. In an aspect, suitable non-proteinaceous stabilizers are disclosed in WO 2005/007185 or WO 2006/020208. In one aspect, the biological activity determined according to step (i) by the method of the invention corresponds to an Botulinum toxin activity of 25, 50, 75, 100, 125, 150 or 200 U (Mouse LD50 units). The formulated Neurotoxin product may be used for human or animal therapy of various diseases or disorders in a therapeutically effective dose or for cosmetic purposes.

The disease or disorder as referred to herein is selected from the group consisting of voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, Blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesias/ dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitrant mutational dysphonia, upper oesophageal sphincter dysfunction, vocal fold granuloma, stuttering Gilles de la Tourette syndrome, middle ear myoclonus, protective larynx closure, postlaryngectomy, speech failure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinsosn's, in amyotrophic lateral sclerosis, spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, myelon tumor and vaginism. A cosmetic use is selected from treatment or reduction of wrinkles like crow's feet or GFL, frowning, facial asymmetries.

All references cited in this specification are herewith incorporated by reference with respect to their entire disclosure content and the disclosure content specifically mentioned in this specification.

The figures show:

FIG. 1: Diagram representing the mode of action of the cell-based assay of the invention. Cells susceptible to Neurotoxin intoxication are seeded in multiwell plates, Thereafter, the cells are intoxicated with Neurotoxin polypeptide and after a given intoxication period the cells are fixated. The specific antibody for Neurotoxin-cleaved SNAP-25 and the specific antibody for un-cleaved SNAP-25 bind to the specific binding sites on SNAP-25. Using enzyme-coupled anti-host specific secondary antibodies, these binding events can be used to generate measurable signals which correlate with the concentration of neurotoxin cleaved SNAP-25 and the total amount of SNAP-25 within the well. With increasing BoNT/A concentration the amount of measured cleaved SNAP-25 increases resulting in a gain of signal.

Figure 2:
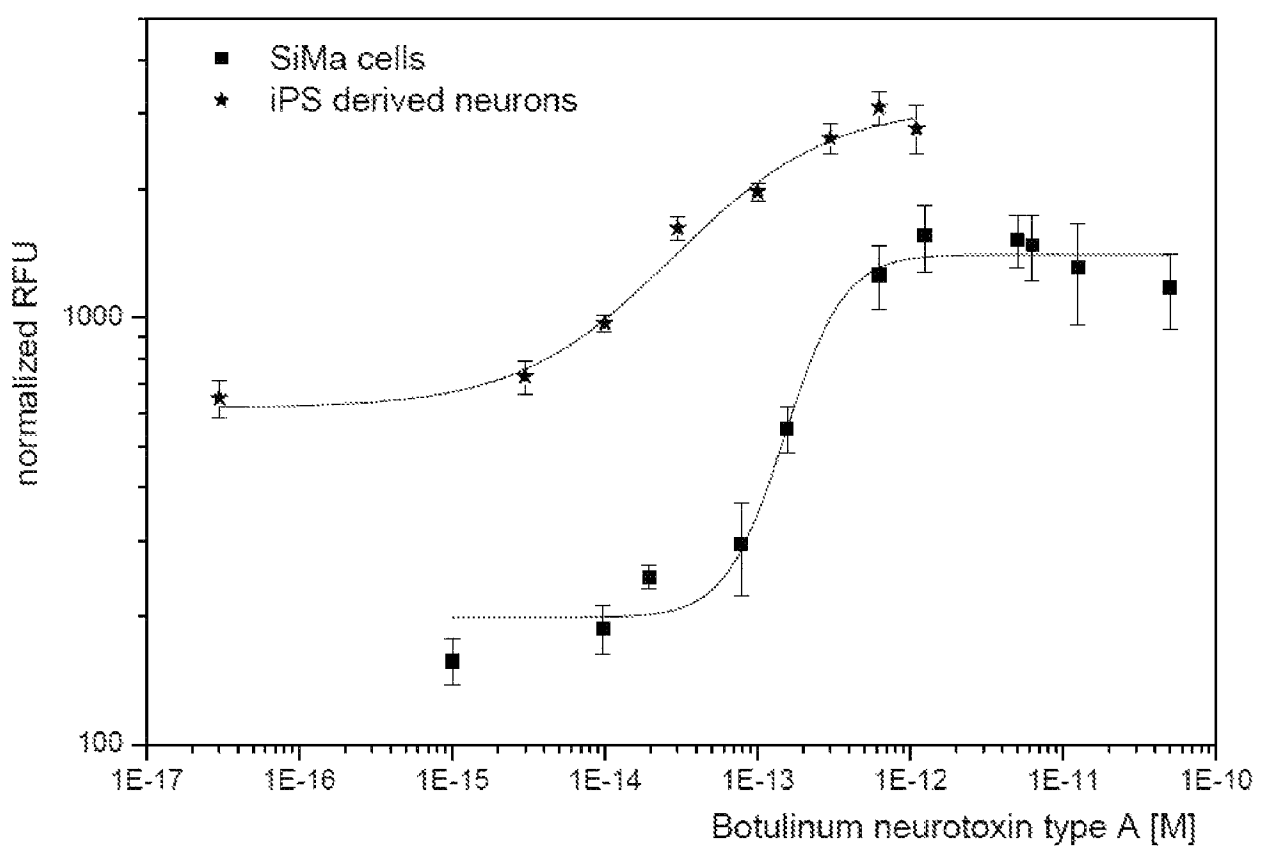

FIG. 2: The two graphs represent the resulting BoNT/A calibration curves for iPS-derived neurons and SiMa cells according to Example 2. They show the dependency between respectively the concentration and activity of BoNT/A and the determined fluorescence signal (RFU) for the HRP substrate and the content of BoNT/A-cleaved SNAP-25 normalized to the total amount of SNAP-25 within the well. Upon increasing concentration and activity, respectively, of BoNT/A, more SNAP-25 is converted by the Neurotoxin, resulting in an increase in the content of cleaved SNAP-25.

Figure 3:
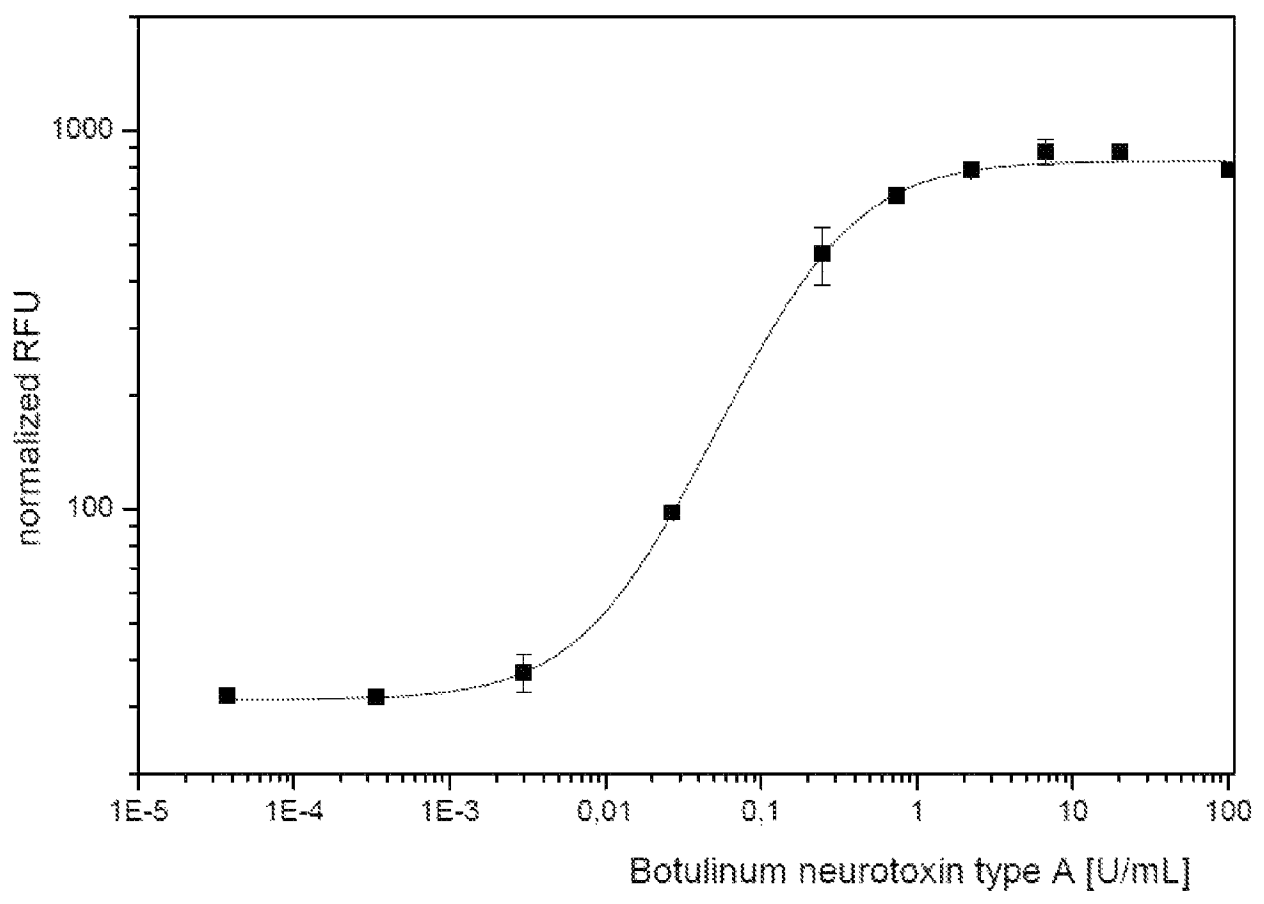

FIG. 3: The graph represents the resulting BoNT/A calibration curve for iPS derived neurons according to Example 4. It shows the dependency between respectively the concentration and activity of BoNT/A and the determined fluorescence signal (RFU) for the HRP substrate and the content of BoNT/A-cleaved SNAP-25 and the content of BoNT/A-cleaved SNAP-25 normalized to the total amount of SNAP-25 within the well. Upon increasing concentration and activity, respectively, of BoNT/A, more SNAP-25 is converted by the Neurotoxin, resulting in an increase in the content of cleaved SNAP-25.

The invention will now be illustrated by the following examples which shall, however, not be construed as limiting the scope of the present invention.

EXAMPLE 1

Generation of Monoclonal Antibodies Specifically Binding to the Cleavage Site of the Neurotoxin-Cleaved Substrate SNAP-25

Mouse monoclonal antibodies specifically binding to the cleavage site of the Neurotoxin-cleaved substrate SNAP-25 have been generated using the hybridoma standard technique. To this end, Balb/c mice (female, 8 weeks) have been immunized with SNAP-25$_{190-197}$ with a Cysteine residue at the N-terminus, "C-TRIDEANQ" (SEQ ID NO: 17). Said N-terminal Cysteine residue is not derived from the SNAP-25 amino acid sequence but has been introduced for linking the SNAP-25$_{190-197}$ peptide (SEQ ID NO: 74) to the keyhole limpet hemocyanin (KLH). Hybridoma cells have been obtained by the fusion of mouse spleen cells with the myeloma cell line SP2/0-Ag14 (SP2/0) purchased from the German Collection of Microorganisms and Cell Culture (DSMZ GmbH, Braunschweig, ACC 146); see also Hemmerlein et al., Molecular Cancer 2006, 5, 41. Antibodies specifically binding to the cleavage site of the Neurotoxin-cleaved substrate SNAP-25 were screened in ELISA. The obtained clones have been selected with respect to their specificity and affinity to BoNT/A-cleaved SNAP-25. As a negative control, the clones have been tested for their non-binding to non-cleaved SNAP-25$_{206}$. As a result, the mouse monoclonal antibodies 20-2-5, 5-10-5, 1-10-4, 16-5-4, 6-3-8, 18-3-3, and 14-12-1 were found to be highly specific for BoNT/A-cleaved SNAP-25$_{197}$, with no detectable cross-reactivity to SNAP25$_{206}$ in ELISA and Western blots. Isotyping of said monoclonal antibodies has been carried out using the mouse monoclonal antibody isotyping test kit (Serotec). As a result it has been found that mAb 20-2-5, 14-12-1, 6-3-8, and 5-10-5 are IgG1 antibodies, whereas mAb 18-3-3, 16-5-4, and 1-10-4 are IgG2a antibodies.

The corresponding amino acid sequences of the VH and VL chains and the corresponding CDR (complementarity determining region) sequences of the mentioned mouse monoclonal antibodies are indicated in the sequence listing.

EXAMPLE 2

Double-Fluorescence-CB-BoNT/A Activity ELISA

Fixation of Cells

1. Remove the media/toxin solution. Add 100 μl/well ice-cold methanol (−20° C.) and incubate for 20 min at −20° C.

Note: Perform all subsequent steps at room temperature.

After Cell Fixation:

1. Remove the methanol solution and add 100 μl/well PBS buffer. For longer storage (>1 day) one should add 300 μl/well PBS buffer and seal the plates with parafilm. The plates should be stored in the refrigerator.

2. Remove the PBS buffer and wash the cells 3 times with 200 μl/well of wash buffer. Each step should be performed for 1 minute with gentle shaking.

3. Remove the wash buffer and add 100 μl/well of quenching buffer and incubate for 20 minutes with gentle shaking.

4. Remove the quenching buffer and wash the cells once with 300 μl/well of wash buffer for 5 minutes under gentle shaking.

5. Remove the wash buffer, and add 200 μl/well of blocking buffer and incubate for 1 hour with gentle shaking.

6. Remove the blocking buffer, and add 100 μl/well permeabilization buffer and incubate for 15 minutes with gentle shaking.

7. Remove the permeabilization buffer and wash the cells once with 300 μl/well of PBS buffer. This step should be performed for 1 minute with gentle shaking.

8. Remove the PBS buffer and add 100 μl of the primary antibody mixture (antibody dilution in blocking buffer) to each well. Incubate overnight (16-18 h) with gentle shaking. The cells are simultaneously incubated with two primary antibodies: a mouse antibody specific for the BoNT/A-cleaved SNAP-25 and a polyclonal rabbit antibody that recognizes SNAP-25 (antibody for determining the total amount of SNAP-25 for normalization).

9. Remove the primary antibody mixture and wash the cells 4 times with 200 μl of wash buffer. Each step should be performed for 5 minutes with gentle shaking.

10. Remove the wash buffer, and add 100 μl of the secondary antibody mixture: HRP-conjugated anti-mouse and AP-conjugated anti-rabbit secondary antibodies (antibody dilution in blocking buffer) to each well and incubate for 2.5-3 hours with gentle shaking.

11. Remove the secondary antibody mixture and wash the cells 5 times with 200 μl/well of wash buffer, followed by 1 washing step with 300 μl/well of HEPES buffer. Each wash step should be performed for 5 minutes with gentle shaking.

12. Remove the PBS buffer from the plate and add 75 μl of a fluorogenic substrate for horseradish-peroxidase (HRP substrate) to each well. Incubate for 50 minutes with gentle shaking. Protect the plates from direct light.

13. Add 75 μl of a fluorogenic substrate for alkaline phosphatase (AP substrate) to each well and incubate for an additional 50 minutes at with gentle shaking. Protect the plates from direct light.

14. Read the plates using a fluorescence plate reader:

excitation at 540 nm; emission at 600 nm.

excitation at 360 nm; emission at 450 nm.

15. Calculation

For normalization, the RFU value for cleaved SNAP-25 (fluorescence at 600 nm) is normalized to RFU of total SNAP-25 (450 nm) in each well. For better illustration of RFUs in a diagram all values are multiplied with a factor 1000 using the following equation:

$$\frac{RFU\ (600\ \text{nm})}{RFU\ (450\ \text{nm})} \times 1000$$

Subsequently the resulting RFU values are averaged for each standard or sample.

Reagent Preparation

Wash Buffer:

0.1% Triton X-100 in 10 mM PBS buffer (pH 7.4)

PBS Buffer (10 mM):

Phosphate buffered saline (Sigma, #P5368) (pH 7.4)

Quenching Buffer:

0.6% $H_2O_2$ in 10 mM PBS buffer (pH 7.4)

Blocking Buffer:

2% BSA in 10 mM PBS buffer (pH 7.4)+0.05% Triton X-100

Permeabilization Buffer:

0.5% Triton X-100 in 10 mM PBS buffer

HEPES Buffer:

50 mM HEPES (pH 7.4)

HRP Substrate:

50 mM HEPES (pH 7.4)

0.007% $H_2O_2$ 150 pM Amplex UltraRed

AP Substrate:

25 mM Diethanolamine (pH 9.8)

2 mM $MgCl_2$

100 μl M DiFMUP

EXAMPLE 3

Illustration of BoNT/A Calibration Curves in the CBA-ELISA According to Example 2 of the Present Invention Cell culture and intoxication with BoNT/A of parental SiMa cells has been carried out according to the provider's manual. Similarly, cell culture and intoxication with BoNT/A of human induced pluripotent stem (iPS) cell-derived neurons (Cellular Dynamics) has been carried out according to the protocol by the manufacturer.

The ELISA has been carried out according to Example 2. As first capture antibody specifically binding to the non-cleaved and BoNT/A-cleaved SNAP-25, the rabbit polyclonal anti-SNAP-25 antibody S9684 (Sigma) has been used. This antibody allows for the detection of the total amount of SNAP-25 within the cells. As a second capture antibody specifically binding to the cleavage site of the BoNT/A-cleaved SNAP-25, the monoclonal antibody clone 20-2-5 of the invention (see Example 1) has been utilized.

The two graphs in FIG. 2 show the obtained BoNT/A calibration curves. They demonstrate the dependency between respectively the concentration and activity of BoNT/A and the determined fluorescence signal (RFU) for the HRP substrate and the content of BoNT/A-cleaved SNAP-25 (RFU values are not blank-corrected in order to illustrate the errors of the single BoNT/A standards). Upon increasing concentration and activity, respectively, of BoNT/A, more SNAP-25 is converted by the Neurotoxin resulting in an increase in the content of cleaved SNAP-25. The dependency of the signal of the BoNT/A concentration/activity of BoNT/A is illustrated by using a 4-parameter equation.

EXAMPLE 4

Double-Fluorescence-CB-BoNT/A Activity ELISA

Fixation of Cells
1. Remove the media/toxin solution. Add 100 µl/well ice-cold methanol (−20° C.) and incubate for 20 min at −20° C.

Note: Perform all subsequent steps at room temperature.
After Cell Fixation:
1. Remove the methanol solution and add 100 µl/well PBS buffer. For longer storage (>1 day) one should add 300 µl/well PBS buffer and seal the plates with parafilm. The plates should be stored in the refrigerator.
2. Remove the PBS buffer and wash the cells 3 times with 200 µl/well of PBS buffer. Each step should be performed for 1 minute with gentle shaking.
3. Remove the PBS buffer and add 100 µl/well of quenching buffer and incubate for 20 minutes with gentle shaking.
4. Remove the quenching buffer and wash the cells once with 300 µl/well of PBS buffer for 3 minutes under gentle shaking.
5. Remove the PBS buffer, and add 200 µl/well of blocking buffer and incubate for 1 hour with gentle shaking.
6. Remove the blocking buffer and add 100 µl of the primary antibody mixture (antibody dilution in blocking buffer) to each well. Incubate overnight (16-18 h) with gentle shaking. The cells are simultaneously incubated with two primary antibodies: a mouse antibody specific for the BoNT/A-cleaved SNAP-25 and a polyclonal rabbit antibody that recognizes SNAP-25 (antibody for determining the total amount of SNAP-25 for normalization).
7. Remove the primary antibody mixture and wash the cells 4 times with 200 µl of PBS buffer. Each step should be performed for 3 minutes with gentle shaking.
8. Remove the PBS buffer, and add 100 µl of the secondary antibody mixture: HRP-conjugated anti-mouse and AP-conjugated anti-rabbit secondary antibodies (antibody dilution in blocking buffer) to each well and incubate for 2.5-3 hours with gentle shaking.
9. Remove the secondary antibody mixture and wash the cells 5 times with 200 µl/well of PBS buffer, followed by 1 washing step with 300 µl/well of HEPES buffer. Each wash step should be performed for 3 minutes with gentle shaking.
10. Remove the HEPES buffer from the plate and add 75 µl of a fluorogenic substrate for horseradish-peroxidase (HRP substrate) to each well. Incubate for 50 minutes with gentle shaking. Protect the plates from direct light.
11. Add 75 µl of a fluorogenic substrate for alkaline phosphatase (AP substrate) to each well and incubate for an additional 50 minutes at with gentle shaking. Protect the plates from direct light.
12. Read the plates using a fluorescence plate reader:
excitation at 540 nm; emission at 600 nm.
excitation at 360 nm; emission at 450 nm.
13. Calculation For normalization, the RFU value for cleaved SNAP-25 (fluorescence at 600 nm) is normalized to RFU of total SNAP-25 (450 nm) in each well. For better illustration of RFUs in a diagram all values are multiplied with a factor 1000 using the following equation:

$$\frac{RFU\ (600\ nm)}{RFU\ (450\ nm)} \times 1000$$

Subsequently the resulting RFU values are averaged for each standard or sample.

Reagent Preparation

PBS Buffer (10 mM):

Phosphate buffered saline (Sigma, #P5368) (pH 7.4)

Quenching Buffer:

0.6% $H_2O_2$ in 10 mM PBS buffer (pH 7.4)

Blocking Buffer:

2% BSA in 10 mM PBS buffer (pH 7.4)+0.05% Triton X-100

HEPES Buffer:

50 mM HEPES (pH 7.4)

HRP Substrate:

50 mM HEPES (pH 7.4)

0.007% $H_2O_2$ 150 pM Amplex UltraRed

AP Substrate:

25 mM Diethanolamine (pH 9.8)

2 mM $MgCl_2$

100 µl M DiFMUP

EXAMPLE 5

Illustration of BoNT/A Calibration Curves in the CBA-ELISA According to Example 4 of the Present Invention Cell culture and intoxication with BoNT/A of human induced pluripotent stem (iPS) cell-derived neurons (Cellular Dynamics) has been carried out according to the protocol by the manufacturer.

The ELISA has been carried out according to Example 4. As first capture antibody specifically binding to the non-cleaved and BoNT/A-cleaved SNAP-25, the rabbit polyclonal anti-SNAP-25 antibody S9684 (Sigma) has been used. This antibody allows for the detection of the total amount of SNAP-25 within the cells. As a second capture antibody specifically binding to the cleavage site of the BoNT/A-cleaved SNAP-25, the monoclonal antibody clone 20-2-5 of the invention (see Example 1) has been utilized.

The graph shown in FIG. 3 represents the obtained BoNT/A calibration curve. It shows the dependency between respectively the concentration and activity of BoNT/A and the determined fluorescence signal (RFU) for the HRP substrate and the content of BoNT/A-cleaved SNAP-25. Upon increasing concentration and activity, respectively, of BoNT/A, more SNAP-25 is converted by the Neurotoxin resulting in an increase in the content of cleaved SNAP-25. The dependency of the signal of the BoNT/A concentration/activity of BoNT/A is illustrated by using a 4-parameter equation.

The invention claimed is:

1. A method for directly determining the biological activity of a *Clostridium botulinum* toxin serotype A (BoNT/A) polypeptide in cells, such method comprising the steps of:
   a) culturing cells susceptible to BoNT/A in wells of a culture dish, incubating the cells susceptible to BoNT/A intoxication with a BoNT/A polypeptide for a period of time and under conditions which allow for the BoNT/A polypeptide to exert its biological activity;
   b) fixing the cells and, optionally, permeabilizing the cells with a detergent;
   c) contacting the cells with at least a first capture antibody which specifically binds to a non-cleaved Neurotoxin substrate SNAP-25 and a Neurotoxin-cleaved substrate SNAP-25 and contacting the cells with at least a second capture antibody which specifically binds to the cleavage site of the Neurotoxin-cleaved substrate SNAP-25 and does not bind non-cleaved Neurotoxin substrate SNAP-25, under conditions which allow for binding of the first and second capture antibodies to the substrates;
   d) contacting the cells in step c) with at least a first detection antibody which specifically binds to the first capture antibody under conditions which allow for binding of the first detection antibody to the first capture antibody, thus forming first detection complexes, and at least a second detection antibody which specifically binds to the second capture antibody under conditions which allow for binding of the second detection antibody to the second capture antibody, thus forming second detection complexes;
   e) determining the total amount of SNAP-25 by measuring the amount of signal of the first detection complexes in the cells and determining the content of cleaved SNAP-25 in the cells by measuring the amount of signal of the second detection complexes of step d), and normalizing the signal of the second detection complexes to the signal of the first detection complexes, and
   f) determining a dependency between a concentration of BoNT/A and activity of BoNT/A based on an increase of the normalized signal in step e), and further generating a calibration curve based on concentration and activity of BoNT/A polypeptide in the cells;
   wherein the second capture antibody is a mouse monoclonal antibody clone 20-2-5 comprising a complementarity determining region (CDR) heavy chain variable region 1 having the sequence of SEQ ID NO:20; a CDR heavy chain variable region 2 having the sequence of SEQ ID NO:21; a CDR heavy chain variable region 3 having the sequence of SEQ ID NO:22; a CDR light chain variable region 1 having the sequence of SEQ ID NO:23; a CDR light chain variable region 2 having the sequence of SEQ ID NO:24; and a CDR light chain variable region 3 having the sequence of SEQ ID NO:25, or a mouse monoclonal antibody MC-6053.

2. The method of claim 1, wherein the first and/or second capture antibody is immobilized.

3. The method of claim 1, wherein the first detection antibody is an alkaline phosphatase (AP)-conjugated antibody, a horseradish-peroxidase (HRP)-conjugated antibody or an antibody conjugated to a fluorescent dye.

4. The method of claim 3, wherein a substrate for the HRP-conjugated antibody is selected from the group consisting of a fluorogenic substrate for horseradish peroxidase, 10-Acetyl-3,7-Dihydroxyphenoxazine (ADHP) and 3-(4-Hydroxyphenyl) propionic acid (HPPA).

5. The method of claim 3, wherein a substrate for the AP-conjugated antibody is selected from the group consisting of 4-methylumbelliferryl phosphate derivative selected from 6,8-Difluoro-4-methylumbelliferyl phosphate (DiFMUP) and fluorescein diphosphate (FDP).

6. The method of claim 1, wherein the second detection antibody is an alkaline phosphatase (AP)-conjugated antibody, a horseradish-peroxidase (HRP)-conjugated antibody, a glucose oxidase-conjugated antibody, a tyrosinase-conjugated antibody or a β-Galactosidase-conjugated antibody.

7. The method of claim 6, wherein a substrate for the HRP-conjugated antibody is selected from the group consisting of a fluorogenic substrate for horseradish peroxidase, 10-Acetyl-3,7-Dihydroxyphenoxazine (ADHD) and 3-(4-Hydroxyphenyl) propionic acid (HPPA).

8. The method of claim 6, wherein a substrate for the AP-conjugated antibody is selected from the group consisting of 4-methylumbelliferryl phosphate derivative selected from 6,8-Difluoro-4-methylumbelliferyl phosphate (DiFMUP) and fluorescein diphosphate (FDP).

9. The method of claim 1, wherein the method is a fluorescence method.

10. The method of claim 1, wherein the cells susceptible to BoNT/A intoxication are neuronal cells or neuronal differentiated cells selected from the group consisting of primary neuronal cells, tumor cells which are capable of differentiating to neuronal cells, neuroblastoma cells, P19 cells and induced pluripotent stem (iPS) cell-derived neurons.

11. The method of claim 1, wherein fixing the cells is carried out by the addition of a fixation agent selected from the group consisting of methanol, ethanol, acetone, formaldehyde and mixtures thereof.

12. The method of claim 1, wherein the first capture antibody which specifically binds to the non-cleaved Neurotoxin substrate SNAP-25 and the Neurotoxin-cleaved substrate SNAP-25 is a rabbit polyclonal anti-SNAP-25 antibody S9684, a rabbit polyclonal anit-SNAP25 antibody PA5-19708, or a rabbit polyclonal anti-SNAP25 antibody PAS-19701.

* * * * *

SEQUENCE LISTING

<160> NUMBER OF SEQ ID NOS: 77

<210> SEQ ID NO 1
<211> LENGTH: 3891
<212> TYPE: DNA
<213> ORGANISM: Clostridium botulinum

<400> SEQUENCE: 1

| | | | | | | |
|---|---|---|---|---|---|---|
| atgccatttg | ttaataaaca | atttaattat | aaagatcctg | taaatggtgt | tgatattgct | 60 |
| tatataaaaa | ttccaaatgc | aggacaaatg | caaccagtaa | aagcttttaa | aattcataat | 120 |
| aaaatatggg | ttattccaga | aagagataca | tttacaaatc | ctgaagaagg | agatttaaat | 180 |
| ccaccaccag | aagcaaaaca | agttccagtt | tcatattatg | attcaacata | tttaagtaca | 240 |
| gataatgaaa | aagataatta | tttaaaggga | gttacaaat | tatttgagag | aatttattca | 300 |
| actgatcttg | aagaatgtt | gttaacatca | atagtaaggg | gaataccatt | ttggggtgga | 360 |
| agtacaatag | atacagaatt | aaaagttatt | gatactaatt | gtattaatgt | gatacaacca | 420 |
| gatggtagtt | atagatcaga | agaacttaat | ctagtaataa | taggaccctc | agctgatatt | 480 |
| atacagtttg | aatgtaaaag | ctttggacat | gaagttttga | atcttacgcg | aaatggttat | 540 |
| ggctctactc | aatacattag | atttagccca | gattttacat | tggttttga | ggagtcactt | 600 |
| gaagttgata | caaatcctct | tttaggtgca | ggcaaatttg | ctacagatcc | agcagtaaca | 660 |
| ttagcacatg | aacttataca | tgctggacat | agattatatg | gaatagcaat | taatccaaat | 720 |
| agggttttta | agtaaatac | taatgcctat | tatgaaatga | gtgggttaga | agtaagcttt | 780 |
| gaggaactta | gaacatttgg | gggacatgat | gcaaagttta | tagatagttt | acaggaaaac | 840 |
| gaatttcgtc | tatattatta | taataagttt | aaagatatag | caagtacact | taataaagct | 900 |
| aaatcaatag | taggtactac | tgcttcatta | cagtatatga | aaaatgtttt | taaagagaaa | 960 |
| tatctcctat | ctgaagatac | atctggaaaa | ttttcggtag | ataaattaaa | atttgataag | 1020 |
| ttatacaaaa | tgttaacaga | gatttacaca | gaggataatt | ttgttaagtt | ttttaaagta | 1080 |
| cttaacagaa | aaacatattt | gaattttgat | aaagccgtat | ttaagataaa | tatagtacct | 1140 |
| aaggtaaatt | acacaatata | tgatggattt | aatttaagaa | atacaaattt | agcagcaaac | 1200 |
| tttaatggtc | aaaatacaga | aattaataat | atgaatttta | ctaaactaaa | aaatttact | 1260 |
| ggattgtttg | aattttataa | gttgctatgt | gtaagaggga | taataacttc | taaaactaaa | 1320 |
| tcattagata | aaggatacaa | taaggcatta | aatgatttat | gtatcaaagt | taataattgg | 1380 |
| gacttgtttt | ttagtccttc | agaagataat | tttactaatg | atctaaataa | aggagaagaa | 1440 |
| attacatctg | atactaatat | agaagcagca | gaagaaaata | ttagtttaga | tttaatacaa | 1500 |
| caatattatt | taacctttaa | ttttgataat | gaacctgaaa | atatttcaat | agaaaatctt | 1560 |
| tcaagtgaca | ttataggcca | attagaactt | atgcctaata | tagaaagatt | tcctaatgga | 1620 |
| aaaaagtatg | agttagataa | atatactatg | ttccattatc | ttcgtgctca | agaatttgaa | 1680 |
| catggtaaat | ctaggattgc | tttaacaaat | tctgttaacg | aagcattatt | aaatcctagt | 1740 |
| cgtgtttata | cattttttc | ttcagactat | gtaaagaaag | ttaataaagc | tacggaggca | 1800 |
| gctatgtttt | taggctgggt | agaacaatta | gtatatgatt | ttaccgatga | aactagcgaa | 1860 |
| gtaagtacta | cggataaaat | tgcggatata | actataatta | ttccatatat | aggacctgct | 1920 |
| ttaaatatag | gtaatatgtt | atataaagat | gattttgtag | gtgctttaat | attttcagga | 1980 |
| gctgttatte | tgttagaatt | tataccagag | attgcaaatac | ctgtattagg | tacttttgca | 2040 |
| cttgtatcat | atattgcgaa | taaggttcta | accgttcaaa | caatagataa | tgctttaagt | 2100 |

-continued

```
aaaagaaatg aaaaatggga tgaggtctat aaatatatag taacaaattg gttagcaaag    2160
gttaatacac agattgatct aataagaaaa aaatgaaag aagctttaga aaatcaagca      2220
gaagcaacaa aggctataat aaactatcag tataatcaat atactgagga agagaaaaat    2280
aatattaatt ttaatattga tgatttaagt tcgaaactta atgagtctat aaataaagct    2340
atgattaata taaataaatt tttgaatcaa tgctctgttt catatttaat gaattctatg    2400
atcccttatg gtgttaaacg gttagaagat tttgatgcta gtcttaaaga tgcattatta    2460
aagtatatat atgataatag aggaaacttta attggtcaag tagatagatt aaaagataaa   2520
gttaataata cacttagtac agatatacct tttcagcttt ccaaatacgt agataatcaa    2580
agattattat ctacatttac tgaatatatt aagaatatta ttaatacttc tatattgaat    2640
ttaagatatg aaagtaatca tttaatagac ttatctaggt atgcatcaaa ataaatatt     2700 ggtagtaaag taaattttga tccaatagat aaaaatcaaa ttcaattatt taatttagaa    2760
agtagtaaaa ttgaggtaat tttaaaaaat gctattgtat ataatagtat gtatgaaaat    2820
tttagtacta gcttttggat aagaattcct aagtatttta acagtataag tctaaataat    2880
gaatatacaa taataaattg tatggaaaat aattcaggat ggaaagtatc acttaattat    2940
ggtgaaataa tctggacttt acaggatact caggaaataa aacaaagagt agttttttaaa   3000 tacagtcaaa tgattaatat atcagattat ataaacagat ggattttttgt aactatcact   3060 aataatagat taaataactc taaaatttat ataaatggaa gattaataga tcaaaaacca    3120
atttcaaatt taggtaatat tcatgctagt aataatataa tgtttaaatt agatggttgt    3180
agagatacac atagatatat ttggataaaa tatttttaatc tttttgataa ggaattaaat   3240 gaaaagaaa tcaaagattt atatgataat caatcaaatt caggtatttt aaaagacttt    3300
tggggtgatt atttacaata tgataaacca tactatatgt taaatttata tgatccaaat   3360
aaatatgtcg atgtaaataa tgtaggtatt agaggttata tgtatcttaa agggcctaga   3420
ggtagcgtaa tgactacaaa catttatta aattcaagtt tgtataggg gacaaaattt     3480 attataaaaa aatatgcttc tggaaataaa gataatatttg ttagaaataa tgatcgtgta   3540
tatattaatg tagtagttaa aaataaagaa tataggttag ctactaatgc atcacaggca   3600
ggcgtagaaa aaatactaag tgcattagaa atacctgatg taggaaatct aagtcaagta    3660
gtagtaatga agtcaaaaaa tgatcaagga ataacaaata aatgcaaaat gaatttacaa    3720
gataataatg ggaatgatat aggctttata ggatttcatc agtttaataa tatagctaaa   3780
ctagtagcaa gtaattggta taatagacaa atagaaagat ctagtaggac tttgggttgc    3840
tcatgggaat ttattcctgt agatgatgga tggggagaaa ggccactgta a            3891
```

<210> SEQ ID NO 2
<211> LENGTH: 1296
<212> TYPE: PRT
<213> ORGANISM: Clostridium botulinum

<400> SEQUENCE: 2

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
```

```
            50                  55                  60
Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
            130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
            450                 455                 460

Ser Pro Ser Glu Asp Asn Phe Thr Asn Asp Leu Asn Lys Gly Glu Glu
465                 470                 475                 480
```

```
Ile Thr Ser Asp Thr Asn Ile Glu Ala Ala Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
                595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
                675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
            725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895
```

-continued

```
Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg
    1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Val Met Lys Ser Lys Asn Asp Gln Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
```

1295

<210> SEQ ID NO 3
<211> LENGTH: 3876
<212> TYPE: DNA
<213> ORGANISM: Clostridium botulinum

<400> SEQUENCE: 3

| | | | | | |
|---|---|---|---|---|---|
| atgccagtta | caataaataa | ttttaattat | aatgatccta | ttgataataa | taatattatt | 60 |
| atgatggagc | ctccatttgc | gagaggtacg | gggagatatt | ataaagcttt | taaaatcaca | 120 |
| gatcgtattt | ggataatacc | ggaaagatat | acttttggat | ataaacctga | ggattttaat | 180 |
| aaaagttccg | gtattttta | tagagatgtt | tgtgaatatt | atgatccaga | ttacttaaat | 240 |
| actaatgata | aaagaatat | attttacaa | acaatgatca | agttatttaa | tagaatcaaa | 300 |
| tcaaaaccat | ggggtgaaaa | gttattagag | atgattataa | atggtatacc | ttatcttgga | 360 |
| gatagacgtg | ttccactcga | agagtttaac | acaaacattg | ctagtgtaac | tgttaataaa | 420 |
| ttaatcagta | atccaggaga | agtggagcga | aaaaaaggta | ttttcgcaaa | tttaataata | 480 |
| tttggacctg | ggccagtttt | aaatgaaaat | gagactatag | ataggtat | acaaaatcat | 540 |
| tttgcatcaa | gggaaggctt | cggggtata | atgcaaatga | agttttgccc | agaatatgta | 600 |
| agcgtattta | ataatgttca | agaaaacaaa | ggcgcaagta | tatttaatag | acgtggatat | 660 |
| ttttcagatc | cagccttgat | attaatgcat | gaacttatac | atgttttaca | tggattatat | 720 |
| ggcattaaag | tagatgattt | accaattgta | ccaaatgaaa | aaaattttt | tatgcaatct | 780 |
| acagatgcta | tacaggcaga | agaactatat | acatttggag | acaagatcc | cagcatcata | 840 |
| actccttcta | cggataaaag | tatctatgat | aaagttttgc | aaaattttag | agggatagtt | 900 |
| gatagactta | acaaggtttt | agtttgcata | tcagatccta | acattaatat | taatatatat | 960 |
| aaaaataaat | ttaaagataa | atataaattc | gttgaagatt | ctgagggaaa | atatagtata | 1020 |
| gatgtagaaa | gttttgataa | attatataaa | agcttaatgt | ttggttttac | agaaactaat | 1080 |
| atagcagaaa | attataaaat | aaaaactaga | gcttcttatt | ttagtgattc | cttaccacca | 1140 |
| gtaaaaataa | aaattttatt | agataatgaa | atctatacta | tagaggaagg | gtttaatata | 1200 |
| tctgataaag | atatggaaaa | agaatataga | ggtcagaata | aagctataaa | taaacaagct | 1260 |
| tatgaagaaa | ttagcaagga | gcatttggct | gtatataaga | tacaaatgtg | taaaagtgtt | 1320 |
| aaagctccag | gaatatgtat | tgatgttgat | aatgaagatt | tgttctttat | agctgataaa | 1380 |
| aatagttttt | cagatgattt | atctaaaaac | gaaagaatag | aatataatac | acagagtaat | 1440 |
| tatatagaaa | atgacttccc | tataaatgaa | ttaattttag | atactgattt | aataagtaaa | 1500 |
| atagaattac | caagtgaaaa | tacagaatca | cttactgatt | ttaatgtaga | tgttccagta | 1560 |
| tatgaaaaac | aacccgctat | aaaaaaaatt | tttacagatg | aaaataccat | ctttcaatat | 1620 |
| ttatactctc | agacatttcc | tctagatata | agagatataa | gtttaacatc | ttcatttgat | 1680 |
| gatgcattat | tattttctaa | caagtttat | tcattttttt | ctatggatta | tattaaaaact | 1740 |
| gctaataaag | tggtagaagc | aggattattt | gcaggttggg | tgaaacagat | agtaaatgat | 1800 |
| tttgtaatcg | aagctaataa | aagcaatact | atggataaaa | ttgcagatat | atctctaatt | 1860 |
| gttccttata | taggattagc | tttaaatgta | ggaaatgaaa | cagctaaagg | aaattttgaa | 1920 |
| aatgcttttg | agattgcagg | agccagtatt | ctactagaat | ttataccaga | acttttaata | 1980 |
| cctgtagttg | gagccttttt | attagaatca | tatattgaca | ataaaaataa | aattattaaa | 2040 |
| acaatagata | atgctttaac | taaaagaaat | gaaaaatgga | gtgatatgta | cggattaata | 2100 |

-continued

```
gtagcgcaat ggctctcaac agttaatact caattttata caataaaaga gggaatgtat    2160
aaggctttaa attatcaagc acaagcattg gaagaaaata taaaatacag atataatata    2220
tattctgaaa aagaaaagtc aaatattaac atcgatttta atgatataaa ttctaaactt    2280
aatgagggta ttaaccaagc tatagataat ataaataatt ttataaatgg atgttctgta    2340
tcatatttaa tgaaaaaaat gattccatta gctgtagaaa aattactaga ctttgataat    2400
actctcaaaa aaaattgtt aaattatata gatgaaaata aattatattt gattggaagt    2460
gcagaatatg aaaaatcaaa agtaaataaa tacttgaaaa ccattatgcc gtttgatctt    2520
tcaatatata ccaatgatac aatactaata gaaatgttta taaatataa tagcgaaatt    2580 ttaaataata ttatcttaaa tttaagatat aaggataata atttaataga tttatcagga    2640 tatgggcaa aggtagaggt tatgatgga gtcgagctta atgataaaaa tcaatttaaa    2700
ttaactagtt cagcaaatag taagattaga gtgactcaaa atcagaatat catatttaat    2760
agtgtgttcc ttgattttag cgttagcttt tggataagaa tacctaaata taagaatgat    2820
ggtatacaaa attatattca taatgaatat acaataatta attgtatgaa aaataattcg    2880
ggctggaaaa tatctattag gggtaatagg ataaatatgga ctttaattga tataaatgga    2940
aaaaccaaat cggtattttt tgaatataac ataagagaag atatatcaga gtatataaat    3000
agatggtttt ttgtaactat tactaataat ttgaataacg ctaaaattta tattaatggt    3060
aagctagaat caaatacaga tattaaagat ataagagaag ttattgctaa tggtgaaata    3120
atatttaaat tagatggtga tatagataga acacaattta tttggatgaa atatttcagt    3180 attttttaata cggaattaag tcaatcaaat attgaagaaa gatataaaat tcaatcatat    3240
agcgaatatt taaagatttt tggggaaat cctttaatgt acaataaaga atattatatg    3300
tttaatgcgg ggaataaaaa ttcatatatt aaactaaaga aagattcacc tgtaggtgaa    3360 atttaacac gtagcaaata taatcaaaat tctaaatata taattatag agatttatat    3420 attggagaaa aatttattat aagaagaaag tcaaattctc aatctataaa tgatgatata    3480
gttagaaaag aagattatat atatctagat ttttttaatt taaatcaaga gtggagagta    3540
tatacctata aatattttaa gaaagaggaa gaaaaattgt ttttagctcc tataagtgat    3600
tctgatgagt tttacaatac tatacaaata aaagaatatg atgaacagcc aacatatagt    3660
tgtcagttgc ttttaaaaa agatgaagaa agtactgatg agataggat gattggtatt    3720 catcgtttct acgaatctgg aattgtattt gaagagtata agattatttt tgtataagt    3780 aaatggtact taaagagagt aaaaaggaaa ccatataatt taaaattgg atgtaattgg    3840 cagtttattc ctaaagatga agggtggact gaataa                             3876
```

<210> SEQ ID NO 4
<211> LENGTH: 1291
<212> TYPE: PRT
<213> ORGANISM: Clostridium botulinum

<400> SEQUENCE: 4

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly

-continued

```
                50                  55                  60
Ile Phe Asn Arg Asp Val Cys Glu Tyr Tyr Asp Pro Asp Tyr Leu Asn
 65                  70                  75                  80

Thr Asn Asp Lys Lys Asn Ile Phe Leu Gln Thr Met Ile Lys Leu Phe
                 85                  90                  95

Asn Arg Ile Lys Ser Lys Pro Leu Gly Glu Lys Leu Leu Glu Met Ile
                100                 105                 110

Ile Asn Gly Ile Pro Tyr Leu Gly Asp Arg Arg Val Pro Leu Glu Glu
                115                 120                 125

Phe Asn Thr Asn Ile Ala Ser Val Thr Val Asn Lys Leu Ile Ser Asn
130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
                180                 185                 190

Met Lys Phe Cys Pro Glu Tyr Val Ser Val Phe Asn Asn Val Gln Glu
                195                 200                 205

Asn Lys Gly Ala Ser Ile Phe Asn Arg Arg Gly Tyr Phe Ser Asp Pro
210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
                260                 265                 270

Gly Gly Gln Asp Pro Ser Ile Ile Thr Pro Ser Thr Asp Lys Ser Ile
                275                 280                 285

Tyr Asp Lys Val Leu Gln Asn Phe Arg Gly Ile Val Asp Arg Leu Asn
                290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
                340                 345                 350

Met Phe Gly Phe Thr Glu Thr Asn Ile Ala Glu Asn Tyr Lys Ile Lys
                355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
                420                 425                 430

Lys Ile Gln Met Cys Lys Ser Val Lys Ala Pro Gly Ile Cys Ile Asp
                435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480
```

```
Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
            610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
                660                 665                 670

Asp Asn Lys Asn Lys Ile Ile Lys Thr Ile Asp Asn Ala Leu Thr Lys
            675                 680                 685

Arg Asn Glu Lys Trp Ser Asp Met Tyr Gly Leu Ile Val Ala Gln Trp
            690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
                740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Gly Cys Ser Val Ser Tyr Leu Met
            770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
                820                 825                 830

Lys Thr Ile Met Pro Phe Asp Leu Ser Ile Tyr Thr Asn Asp Thr Ile
            835                 840                 845

Leu Ile Glu Met Phe Asn Lys Tyr Asn Ser Glu Ile Leu Asn Asn Ile
            850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895
```

```
Asn Gln Phe Lys Leu Thr Ser Ser Ala Asn Ser Lys Ile Arg Val Thr
                900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
        930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
        980                 985                 990

Glu Asp Ile Ser Glu Tyr Ile Asn Arg Trp Phe Phe Val Thr Ile Thr
        995                 1000                1005

Asn Asn Leu Asn Asn Ala Lys Ile Tyr Ile Asn Gly Lys Leu Glu
        1010                1015                1020

Ser Asn Thr Asp Ile Lys Asp Ile Arg Glu Val Ile Ala Asn Gly
        1025                1030                1035

Glu Ile Ile Phe Lys Leu Asp Gly Asp Ile Asp Arg Thr Gln Phe
        1040                1045                1050

Ile Trp Met Lys Tyr Phe Ser Ile Phe Asn Thr Glu Leu Ser Gln
        1055                1060                1065

Ser Asn Ile Glu Glu Arg Tyr Lys Ile Gln Ser Tyr Ser Glu Tyr
        1070                1075                1080

Leu Lys Asp Phe Trp Gly Asn Pro Leu Met Tyr Asn Lys Glu Tyr
        1085                1090                1095

Tyr Met Phe Asn Ala Gly Asn Lys Asn Ser Tyr Ile Lys Leu Lys
        1100                1105                1110

Lys Asp Ser Pro Val Gly Glu Ile Leu Thr Arg Ser Lys Tyr Asn
        1115                1120                1125

Gln Asn Ser Lys Tyr Ile Asn Tyr Arg Asp Leu Tyr Ile Gly Glu
        1130                1135                1140

Lys Phe Ile Ile Arg Arg Lys Ser Asn Ser Gln Ser Ile Asn Asp
        1145                1150                1155

Asp Ile Val Arg Lys Glu Asp Tyr Ile Tyr Leu Asp Phe Phe Asn
        1160                1165                1170

Leu Asn Gln Glu Trp Arg Val Tyr Thr Tyr Lys Tyr Phe Lys Lys
        1175                1180                1185

Glu Glu Glu Lys Leu Phe Leu Ala Pro Ile Ser Asp Ser Asp Glu
        1190                1195                1200

Phe Tyr Asn Thr Ile Gln Ile Lys Glu Tyr Asp Glu Gln Pro Thr
        1205                1210                1215

Tyr Ser Cys Gln Leu Leu Phe Lys Lys Asp Glu Glu Ser Thr Asp
        1220                1225                1230

Glu Ile Gly Leu Ile Gly Ile His Arg Phe Tyr Glu Ser Gly Ile
        1235                1240                1245

Val Phe Glu Glu Tyr Lys Asp Tyr Phe Cys Ile Ser Lys Trp Tyr
        1250                1255                1260

Leu Lys Glu Val Lys Arg Lys Pro Tyr Asn Leu Lys Leu Gly Cys
        1265                1270                1275

Asn Trp Gln Phe Ile Pro Lys Asp Glu Gly Trp Thr Glu
        1280                1285                1290
```

<210> SEQ ID NO 5
<211> LENGTH: 3843
<212> TYPE: DNA
<213> ORGANISM: Clostridium botulinum

<400> SEQUENCE: 5

| | | | | | |
|---|---|---|---|---|---|
| atgccaataa | caattaacaa | ctttaattat | tcagatcctg | ttgataataa | aaatatttta | 60 |
| tatttagata | ctcatttaaa | tacattagct | aatgagcctg | aaaaagcctt | tcgcattata | 120 |
| gggaatatat | gggtaatacc | cgatagattt | tcaagagatt | ctaatccaaa | tttaaataaa | 180 |
| cctcctcgag | ttacaagccc | taaaagtggt | tattatgatc | ctaattattt | gagtactgat | 240 |
| tctgaaaaag | atacattttt | aaaagaaatt | ataaagttat | ttaaaagaat | taactctaga | 300 |
| gaaataggag | aagaattaat | atatagactt | gcaacagaca | tacccttttcc | tgggaataac | 360 |
| aatactccaa | ttaatacttt | tgattttgat | gtagatttta | acagtgttga | tgttaaaact | 420 |
| agacaaggta | caactgggt | taaaactggt | agtataaatc | ctagtgttat | aataactgga | 480 |
| cctagagaaa | acattataga | cccagaaact | tctacgttta | aattaactaa | caatactttt | 540 |
| gcggcacaag | aaggatttgg | tgctttatca | ataatttcaa | tatcacctag | atttatgcta | 600 |
| acatatagta | atgcaactaa | taatgtagga | gagggtagat | tttctaagtc | tgaattttgc | 660 |
| atggatccaa | tactaatttt | aatgcatgaa | cttaatcatg | caatgcataa | tttatatgga | 720 |
| atagctatac | caaatgatca | agaatttca | tctgtaacta | gtaatatttt | ttattctcaa | 780 |
| tataaggtga | aattagagta | tgcagaaata | tatgcatttg | gaggtccaac | tatagacctt | 840 |
| attcctaaaa | gtgcaaggaa | atattttgag | gaaaaggcat | tggattatta | tagatccata | 900 |
| gctaaaagac | ttaatagtat | aactactgca | aatccttcaa | gctttaataa | atatataggaa | 960 |
| gaatataaac | agaaacttat | tagaaagtat | agattcgtag | tagaatcttc | aggtgaagtt | 1020 |
| gcagtagatc | gtaataagtt | tgctgagtta | tataaagaac | ttacacaaat | atttacagaa | 1080 |
| tttaactacg | ctaaaatata | taatgtacaa | aataggaaaa | tatatctttc | aaatgtatat | 1140 |
| actccggtta | cggcaaatat | attagacgat | aatgtttatg | atatacaaaa | tggatttaac | 1200 |
| atacctaaaa | gtaatttaaa | tgtactattt | atgggtcaaa | atttatctcg | aaatccagca | 1260 |
| ttaagaaaag | tcaatcctga | aaatatgctt | tattattta | caaaatttg | ccataaagca | 1320 |
| atagatggta | gatcattata | taataaaaca | ttagattgta | gagagctttt | agttaaaaat | 1380 |
| actgacttac | cctttatagg | tgatattagt | gatatcaaaa | ctgatatatt | tttaagcaaa | 1440 |
| gatattaatg | aagaaactga | agttatagac | tatccggaca | atgtttcagt | ggatcaagtt | 1500 |
| attctcagta | agaatccctc | agaacatgga | caactagatt | tattataccc | tattattgaa | 1560 |
| ggtgagagtc | aagtattacc | gggagagaat | caagtctttt | atgataatag | aactcaaaat | 1620 |
| gttgattatt | tgaattctta | ttattaccta | gaatctcaaa | aactaagtga | taatgttgaa | 1680 |
| gattttactt | ttacgacatc | aattgaggaa | gctttggata | tagtggaaa | agtatatact | 1740 |
| tactttccta | aactagctga | taaagtaaat | acggtgttc | aaggtggtt | atttttaatg | 1800 |
| tgggcaaatg | atgtagttga | agattttact | acaaatattc | taagaaaaga | tacattagat | 1860 |
| aaaatatcag | atgtatcagc | tattattccc | tatataggac | ctgcattaaa | tataagtaat | 1920 |
| tctgtaagaa | ggggaaattt | tactgaagca | tttgcagtta | ccggtgtaac | tattttatta | 1980 |
| gaagcgtttc | aagaatttac | aatacctgca | cttggtgcat | ttgtgattta | tagtaaggtt | 2040 |
| caagaaagaa | acgagattat | taaaactata | gataattgtt | tagaacaaag | gattaaaaga | 2100 |
| tggaaagatt | catatgaatg | gatgatagga | acgtggttat | ccaggattac | tactcaattt | 2160 |

-continued

```
aataatataa gttatcaaat gtatgattct ttaaattatc aggcagatgc aatcaaagat     2220
aaaatagatt tagaatataa aaaatactca ggaagtgata aagaaaatat aaaaagtcaa     2280
gttgaaaatt taaaaaatag tttagatata aaaatctcgg aagcaatgaa taatataaat     2340
aaatttatac gagaatgttc tgtaacatac ttatttaaaa atatgctccc taaagtaatt     2400
gatgaattaa ataagtttga tttaaaaact aaaacagaat taattaatct tatagatagt     2460
cataatatta ttctagttgg tgaagtagat agattaaaag caaaagtaaa tgagagtttt     2520
gaaaatacaa tacccttttaa tattttttca tatactaata attctttatt aaaagatata    2580
attaatgaat atttcaatag tattaatgat tcaaaaattt tgagcttaca aaacaaaaaa     2640
aatgctttag tggatacatc aggatataat gcagaagtga ggctagaagg tgatgttcaa     2700
gttaatacga tatatacaaa tgattttaaa ttaagtagtt caggagataa aattatagta     2760
aatttaaata ataatatttt atatagcgct atttatgaga actctagtgt tagttttttgg    2820 attaagatat ctaaagattt aactaattct cataatgaat atacaataat taatagtata    2880
aaacaaaatt ctgggtggaa attatgtatt aggaatggca atatagaatg gattttacaa    2940
gatattaata gaaagtataa aagtttaatt tttgattata gtgaatcatt aagtcataca    3000
ggatatacaa ataaatggtt ttttgttact ataactaata atataatggg gtatatgaaa    3060
ctttatataa atggagaatt aaagcagagt gaaagaattg aagatttaaa tgaggttaag    3120
ttagataaaa ccatagtatt tggaatagat gagaataag atgagaatca gatgctttgg    3180
attagagatt ttaatatttt ttctaaagaa ttaagcaatg aagatattaa tattgtatat    3240
gagggacaaa tattaagaaa tgttattaaa gattattggg gaaatccttt gaagtttgat    3300
acagaatatt atattattaa tgataattat atagataggt atatagcacc taaaagtaat    3360
atacttgtac ttgttcagta tccagataga tctaaattat atactggaaa tcctattact    3420
attaaatcag tatctgataa gaatccttat agtagaattt taaatggaga taatataatg    3480
tttcatatgt tatataatag tgggaaatat atgataataa gagatactga tacaatatat    3540
gcaatagaag gaagagagtg ttcaaaaaat tgtgtatatg cattaaaatt acagagtaat    3600
ttaggtaatt atggtatagg tatatttagt ataaaaaata ttgtatctca aaataaatat    3660
tgtagtcaaa ttttctctag ttttatgaaa aatacaatgc ttctagcaga tatatataaa    3720
ccttggagat tttcttttga aaatgcatac acgccagttg cagtaactaa ttatgagaca    3780
aaactattat caacttcatc tttttggaaa tttatttcta gggatccagg atgggtagag    3840
taa                                                                  3843
```

<210> SEQ ID NO 6
<211> LENGTH: 1280
<212> TYPE: PRT
<213> ORGANISM: Clostridium botulinum

<400> SEQUENCE: 6

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Ile Gly Asn Ile Trp Val Ile Pro Asp
        35                  40                  45

Arg Phe Ser Arg Asp Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp

-continued

```
                65                  70                  75                  80
Ser Glu Lys Asp Thr Phe Leu Lys Glu Ile Ile Lys Leu Phe Lys Arg
                        85                  90                  95
Ile Asn Ser Arg Glu Ile Gly Glu Glu Leu Ile Tyr Arg Leu Ala Thr
                    100                 105                 110
Asp Ile Pro Phe Pro Gly Asn Asn Thr Pro Ile Asn Thr Phe Asp
                115                 120                 125
Phe Asp Val Asp Phe Asn Ser Val Asp Val Lys Thr Arg Gln Gly Asn
        130                 135                 140
Asn Trp Val Lys Thr Gly Ser Ile Asn Pro Ser Val Ile Ile Thr Gly
145                 150                 155                 160
Pro Arg Glu Asn Ile Ile Asp Pro Glu Thr Ser Thr Phe Lys Leu Thr
                        165                 170                 175
Asn Asn Thr Phe Ala Ala Gln Glu Gly Phe Gly Ala Leu Ser Ile Ile
                    180                 185                 190
Ser Ile Ser Pro Arg Phe Met Leu Thr Tyr Ser Asn Ala Thr Asn Asn
                195                 200                 205
Val Gly Glu Gly Arg Phe Ser Lys Ser Glu Phe Cys Met Asp Pro Ile
        210                 215                 220
Leu Ile Leu Met His Glu Leu Asn His Ala Met His Asn Leu Tyr Gly
225                 230                 235                 240
Ile Ala Ile Pro Asn Asp Gln Arg Ile Ser Ser Val Thr Ser Asn Ile
                        245                 250                 255
Phe Tyr Ser Gln Tyr Lys Val Lys Leu Glu Tyr Ala Glu Ile Tyr Ala
                    260                 265                 270
Phe Gly Gly Pro Thr Ile Asp Leu Ile Pro Lys Ser Ala Arg Lys Tyr
                275                 280                 285
Phe Glu Glu Lys Ala Leu Asp Tyr Tyr Arg Ser Ile Ala Lys Arg Leu
        290                 295                 300
Asn Ser Ile Thr Thr Ala Asn Pro Ser Ser Phe Asn Lys Tyr Ile Gly
305                 310                 315                 320
Glu Tyr Lys Gln Lys Leu Ile Arg Lys Tyr Arg Phe Val Val Glu Ser
                        325                 330                 335
Ser Gly Glu Val Ala Val Asp Arg Asn Lys Phe Ala Glu Leu Tyr Lys
                    340                 345                 350
Glu Leu Thr Gln Ile Phe Thr Glu Phe Asn Tyr Ala Lys Ile Tyr Asn
                355                 360                 365
Val Gln Asn Arg Lys Ile Tyr Leu Ser Asn Val Tyr Thr Pro Val Thr
        370                 375                 380
Ala Asn Ile Leu Asp Asp Asn Val Tyr Asp Ile Gln Asn Gly Phe Asn
385                 390                 395                 400
Ile Pro Lys Ser Asn Leu Asn Val Leu Phe Met Gly Gln Asn Leu Ser
                        405                 410                 415
Arg Asn Pro Ala Leu Arg Lys Val Asn Pro Glu Asn Met Leu Tyr Leu
                    420                 425                 430
Phe Thr Lys Phe Cys His Lys Ala Ile Asp Gly Arg Ser Leu Tyr Asn
                435                 440                 445
Lys Thr Leu Asp Cys Arg Glu Leu Leu Val Lys Asn Thr Asp Leu Pro
        450                 455                 460
Phe Ile Gly Asp Ile Ser Asp Ile Lys Thr Asp Ile Phe Leu Ser Lys
465                 470                 475                 480
Asp Ile Asn Glu Glu Thr Glu Val Ile Asp Tyr Pro Asp Asn Val Ser
                        485                 490                 495
```

```
Val Asp Gln Val Ile Leu Ser Lys Asn Thr Ser Glu His Gly Gln Leu
            500                 505                 510

Asp Leu Leu Tyr Pro Ile Ile Glu Gly Glu Ser Gln Val Leu Pro Gly
            515                 520                 525

Glu Asn Gln Val Phe Tyr Asp Asn Arg Thr Gln Asn Val Asp Tyr Leu
            530                 535                 540

Asn Ser Tyr Tyr Tyr Leu Glu Ser Gln Lys Leu Ser Asp Asn Val Glu
545                 550                 555                 560

Asp Phe Thr Phe Thr Thr Ser Ile Glu Glu Ala Leu Asp Asn Ser Gly
                565                 570                 575

Lys Val Tyr Thr Tyr Phe Pro Lys Leu Ala Asp Lys Val Asn Thr Gly
            580                 585                 590

Val Gln Gly Gly Leu Phe Leu Met Trp Ala Asn Asp Val Val Glu Asp
            595                 600                 605

Phe Thr Thr Asn Ile Leu Arg Lys Asp Thr Leu Asp Lys Ile Ser Asp
            610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Gln Glu Phe Thr Ile Pro Ala Leu Gly
            660                 665                 670

Ala Phe Val Ile Tyr Ser Lys Val Gln Glu Arg Asn Glu Ile Ile Lys
            675                 680                 685

Thr Ile Asp Asn Cys Leu Glu Gln Arg Ile Lys Arg Trp Lys Asp Ser
            690                 695                 700

Tyr Glu Trp Met Ile Gly Thr Trp Leu Ser Arg Ile Thr Thr Gln Phe
705                 710                 715                 720

Asn Asn Ile Ser Tyr Gln Met Tyr Asp Ser Leu Asn Tyr Gln Ala Asp
                725                 730                 735

Ala Ile Lys Asp Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
            755                 760                 765

Asp Ile Lys Ile Ser Glu Ala Met Asn Asn Ile Asn Lys Phe Ile Arg
            770                 775                 780

Glu Cys Ser Val Thr Tyr Leu Phe Lys Asn Met Leu Pro Lys Val Ile
785                 790                 795                 800

Asp Glu Leu Asn Lys Phe Asp Leu Lys Thr Lys Thr Glu Leu Ile Asn
                805                 810                 815

Leu Ile Asp Ser His Asn Ile Ile Leu Val Gly Glu Val Asp Arg Leu
            820                 825                 830

Lys Ala Lys Val Asn Glu Ser Phe Glu Asn Thr Ile Pro Phe Asn Ile
            835                 840                 845

Phe Ser Tyr Thr Asn Asn Ser Leu Leu Lys Asp Ile Ile Asn Glu Tyr
            850                 855                 860

Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Leu Glu
                885                 890                 895

Gly Asp Val Gln Val Asn Thr Ile Tyr Thr Asn Asp Phe Lys Leu Ser
            900                 905                 910
```

Ser Ser Gly Asp Lys Ile Ile Val Asn Leu Asn Asn Asn Ile Leu Tyr
            915                 920                 925

Ser Ala Ile Tyr Glu Asn Ser Ser Val Ser Phe Trp Ile Lys Ile Ser
        930                 935                 940

Lys Asp Leu Thr Asn Ser His Asn Glu Tyr Thr Ile Ile Asn Ser Ile
945                 950                 955                 960

Lys Gln Asn Ser Gly Trp Lys Leu Cys Ile Arg Asn Gly Asn Ile Glu
                965                 970                 975

Trp Ile Leu Gln Asp Ile Asn Arg Lys Tyr Lys Ser Leu Ile Phe Asp
            980                 985                 990

Tyr Ser Glu Ser Leu Ser His Thr Gly Tyr Thr Asn Lys Trp Phe Phe
        995                 1000                1005

Val Thr Ile Thr Asn Asn Ile Met Gly Tyr Met Lys Leu Tyr Ile
    1010                1015                1020

Asn Gly Glu Leu Lys Gln Ser Glu Arg Ile Glu Asp Leu Asn Glu
    1025                1030                1035

Val Lys Leu Asp Lys Thr Ile Val Phe Gly Ile Asp Glu Asn Ile
    1040                1045                1050

Asp Glu Asn Gln Met Leu Trp Ile Arg Asp Phe Asn Ile Phe Ser
    1055                1060                1065

Lys Glu Leu Ser Asn Glu Asp Ile Asn Ile Val Tyr Glu Gly Gln
    1070                1075                1080

Ile Leu Arg Asn Val Ile Lys Asp Tyr Trp Gly Asn Pro Leu Lys
    1085                1090                1095

Phe Asp Thr Glu Tyr Tyr Ile Ile Asn Asp Asn Tyr Ile Asp Arg
    1100                1105                1110

Tyr Ile Ala Pro Lys Ser Asn Ile Leu Val Leu Val Gln Tyr Pro
    1115                1120                1125

Asp Arg Ser Lys Leu Tyr Thr Gly Asn Pro Ile Thr Ile Lys Ser
    1130                1135                1140

Val Ser Asp Lys Asn Pro Tyr Ser Arg Ile Leu Asn Gly Asp Asn
    1145                1150                1155

Ile Met Phe His Met Leu Tyr Asn Ser Gly Lys Tyr Met Ile Ile
    1160                1165                1170

Arg Asp Thr Asp Thr Ile Tyr Ala Ile Glu Gly Arg Glu Cys Ser
    1175                1180                1185

Lys Asn Cys Val Tyr Ala Leu Lys Leu Gln Ser Asn Leu Gly Asn
    1190                1195                1200

Tyr Gly Ile Gly Ile Phe Ser Ile Lys Asn Ile Val Ser Gln Asn
    1205                1210                1215

Lys Tyr Cys Ser Gln Ile Phe Ser Ser Phe Met Lys Asn Thr Met
    1220                1225                1230

Leu Leu Ala Asp Ile Tyr Lys Pro Trp Arg Phe Ser Phe Glu Asn
    1235                1240                1245

Ala Tyr Thr Pro Val Ala Val Thr Asn Tyr Glu Thr Lys Leu Leu
    1250                1255                1260

Ser Thr Ser Ser Phe Trp Lys Phe Ile Ser Arg Asp Pro Gly Trp
    1265                1270                1275

Val Glu
    1280

<210> SEQ ID NO 7
<211> LENGTH: 3858
<212> TYPE: DNA

<213> ORGANISM: Clostridium botulinum

<400> SEQUENCE: 7

```
atgacatggc cagtaaaaga ttttaattat agtgatcctg ttaatgacaa tgatatatta      60
tatttaagaa taccacaaaa taagttaatt actacacctg taaaagcttt tatgattact     120
caaaatattt gggtaatacc agaaagattt tcatcagata ctaatccaag tttaagtaaa     180
ccgcctagac ctacttcaaa gtatcaaagt tattatgatc ctagttattt atctactgat     240
gagcaaaaag atacatttt aaaagggatt ataaaattat ttaaagaat aatgaaaga       300
gatataggaa aaaattaat aaattattta gtagttggtt cacctttat gggagattca      360
agtacgcctg aagatacatt tgattttaca cgtcatacta ctaatattgc agttgaaaag    420
tttgaaaatg gtagttggaa agtaacaaat attataacac aagtgtatt gatatttgga    480
ccacttccta atatattaga ctatacagca tcccttacat tgcaaggaca acaatcaaat   540
ccatcatttg aagggtttgg aacattatct atactaaaag tagcacctga atttttgtta  600
acatttagtg atgtaacatc taatcaaagt tcagctgtat taggcaaatc tatatttgt   660
atggatccag taatagcttt aatgcatgag ttaacacatt ctttgcatca attgtatgga  720
ataaatatac catctgataa aaggattcgt ccacaagtta gcgagggatt tttttctcaa  780
gatggaccca acgtacaatt tgaggaatta tacacatttg gaggatcaga tgttgaaata  840
atacctcaaa ttgaaagatt acaattaaga gaaaaagcat taggtcacta taagatata   900
gcgaaaagac ttaataatat taataaaact attccttcta gttggagtag taatatagat  960
aaatataaaa aaatatttc tgaaaagtat aattttgata agataatac aggaaatttt    1020
gttgtaaata ttgataaatt caatagctta tattcagact tgactaatgt tatgtcagaa  1080
gttgtttatt cttcgcaata taatgttaaa acaggactc attattttc aaagcattat   1140
ctacctgtat ttgcaaatat attagatgat aatatttata ctataataaa cggttttaat 1200
ttaacaacta aaggttttaa tatagaaaat tcgggtcaga atatagaaag gaatcctgca 1260
ctacaaaaac ttagttcaga aagtgtagta gatttgttta caaaagtatg tttaagatta  1320
acaagaaata gtagagatga ttcaacatgt attcaagtta aaaataatac attaccttat 1380
gtagctgata agatagcat tcacaagaa atatttgaaa gtcaaattat tacagatgag 1440
actaatgtag aaaattattc agataatttt tcattagatg aatctatttt agatgcaaaa 1500
gtccctacta atcctgaagc agtagatcca ctgttaccca atgttaatat ggaaccttta 1560
aatgttccag gtgaagaaga agtatttat gatgatatta ctaaagatgt tgattattta 1620
aactcttatt attatttgga agcccaaaaa ttaagtaata atgttgaaaa tattactctt 1680
acaacttcag ttgaagaagc attaggttat agcaataaga tatacacatt tttacctagc 1740
ttagctgaaa aagtgaataa aggtgttcaa gcaggtttat tcttaaattg ggcgaatgaa 1800
gtagttgagg attttactac aaatattatg aaaaagata cattggataa aatatcagat 1860
gtatcagcca taattccata tataggacct gccttaaata taggaaattc agcattaagg 1920
ggaaacttta agcaagcatt tgcaacagct ggtgtagctt ttttgttaga aggatttcca 1980
gagtttacaa tacctgcact cggtgtattt acctttata gttctattca agaaagagag 2040
aaaattatta aaactataga aaattgttta gaacaaagag ttaagagatg gaaagattca 2100
tatcaatgga tggtatcaaa ttggttgtca agaattacta ctcgatttaa tcatataagt 2160
tatcaaatgt atgattcttt gagttatcag gcagatgcaa tcaaagctaa aatagattta 2220
gaatataaaa aatactcagg aagtgataaa gaaaatataa aaagtcaagt tgaaaattta 2280
```

-continued

```
aaaaatagtt tagatgtaaa aatctcggaa gcaatgaata atataaataa atttatacga    2340
gaatgttctg taacatactt atttaaaaat atgctcccta aagtaattga tgaattaaat    2400
aagtttgatt taaaaactaa aacagaatta attaatctta tagatagtca taatattatt    2460
ctagttggtg aagtagatag attaaaagca aaagtaaatg agagttttga aaatacaata    2520
ccctttaata ttttttcata tactaataat tctttattaa agatatgat taatgaatat     2580 ttcaatagta ttaatgattc aaaaattttg agcttacaaa ataaaaaaaa tacttttgatg   2640 gatacatcag gatataacgc agaagtgaga gtagaaggca atgttcagct taatccaata   2700
tttccatttg actttaaatt aggtagttca ggggatgata gaggtaaagt tatagtaacc    2760
cagaatgaaa atattgtata taatgctatg tatgaaagtt ttagtattag tttttggatt   2820
aggataaata aatgggtaag taatttacct ggatatacta taattgatag tgttaaaaat   2880
aactcaggtt ggagtatagg tattattagt aattttttag tgtttacttt aaaacaaaat   2940
gaaaatagtg aacaagatat aaactttagt tatgatatat caagaatgc tgcgggatat    3000 aataaatggt ttttgtaac tattactacc aatatgatgg gaaatatgat gatttatata   3060 aatgaaaat taatagatac tataaaagtt aaagagttaa ctggaattaa ttttagcaaa    3120
actataacat ttcaaatgaa taaaattcca atactggct taattacctc agattctgat    3180
aacatcaata tgtggataag ggattttat atctttgcta aagaattaga tgataaagat    3240
attaatatat tattaatag cttgcaatat actaatgttg taaaagatta ttggggaaat   3300
gatttaagat atgataaaga atattacatg attaacgtaa attatatgaa tagatatatg   3360
tctaaaaaag gcaatggaat tgttttaat acacgtaaaa ataataatga cttcaatgaa    3420
ggatataaaa ttataataaa aagaattaga ggaaatacaa atgatactag agtacgagga   3480
gaaaatgtat tatattttaa tactacaatt gataacaaac aatatagttt aggtatgtat   3540
aaaccttcta gaaatctagg gactgattta gttccactag gtgcattgga tcaaccaatg   3600
gatgagatac gtaaatatgg ttcgtttata atacaaccat gcaatacttt tgattactat    3660
gcatcacaat tattttttgtc aagtaatgca acaacaaata ggcttggaat actatcaatt   3720
ggtagttata gtttcaaact tggagatgac tattggttta tcacgaata tttaattcct   3780 gttataaaaa tagagcatta tgcttcatta ttagaatcaa catcaactca ttgggttttt   3840
gtacctgcaa gtgaataa                                                  3858
```

<210> SEQ ID NO 8
<211> LENGTH: 1285
<212> TYPE: PRT
<213> ORGANISM: Clostridium botulinum

<400> SEQUENCE: 8

```
Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
```

```
                    85                  90                  95
Ile Asn Glu Arg Asp Ile Gly Lys Lys Leu Ile Asn Tyr Leu Val Val
                100                 105                 110

Gly Ser Pro Phe Met Gly Asp Ser Ser Thr Pro Glu Asp Thr Phe Asp
                115                 120                 125

Phe Thr Arg His Thr Thr Asn Ile Ala Val Glu Lys Phe Glu Asn Gly
            130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Ser Asp Val Glu Ile Ile Pro Gln Ile Glu Arg Leu Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ser Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Lys His Tyr Leu Pro Val Phe
    370                 375                 380

Ala Asn Ile Leu Asp Asp Asn Ile Tyr Thr Ile Ile Asn Gly Phe Asn
385                 390                 395                 400

Leu Thr Thr Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Arg Asn Ser Arg Asp Asp Ser
        435                 440                 445

Thr Cys Ile Gln Val Lys Asn Asn Thr Leu Pro Tyr Val Ala Asp Lys
    450                 455                 460

Asp Ser Ile Ser Gln Glu Ile Phe Glu Ser Gln Ile Ile Thr Asp Glu
465                 470                 475                 480

Thr Asn Val Glu Asn Tyr Ser Asp Asn Phe Ser Leu Asp Glu Ser Ile
                485                 490                 495

Leu Asp Ala Lys Val Pro Thr Asn Pro Glu Ala Val Asp Pro Leu Leu
            500                 505                 510
```

```
Pro Asn Val Asn Met Glu Pro Leu Asn Val Pro Gly Glu Glu Val
        515                 520                 525

Phe Tyr Asp Asp Ile Thr Lys Asp Val Asp Tyr Leu Asn Ser Tyr Tyr
    530                 535                 540

Tyr Leu Glu Ala Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
        595                 600                 605

Ile Met Lys Lys Asp Thr Leu Asp Lys Ile Ser Asp Val Ser Ala Ile
        610                 615                 620

Ile Pro Tyr Ile Gly Pro Ala Leu Asn Ile Gly Asn Ser Ala Leu Arg
625                 630                 635                 640

Gly Asn Phe Lys Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
        675                 680                 685

Cys Leu Glu Gln Arg Val Lys Arg Trp Lys Asp Ser Tyr Gln Trp Met
        690                 695                 700

Val Ser Asn Trp Leu Ser Arg Ile Thr Thr Arg Phe Asn His Ile Ser
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
            740                 745                 750

Ile Lys Ser Gln Val Glu Asn Leu Lys Asn Ser Leu Asp Val Lys Ile
        755                 760                 765

Ser Glu Ala Met Asn Asn Ile Asn Lys Phe Ile Arg Glu Cys Ser Val
770                 775                 780

Thr Tyr Leu Phe Lys Asn Met Leu Pro Lys Val Ile Asp Glu Leu Asn
785                 790                 795                 800

Lys Phe Asp Leu Lys Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Ile Pro Phe Asn Ile Phe Ser Tyr Thr
        835                 840                 845

Asn Asn Ser Leu Leu Lys Asp Met Ile Asn Glu Tyr Phe Asn Ser Ile
850                 855                 860

Asn Asp Ser Lys Ile Leu Ser Leu Gln Asn Lys Lys Asn Thr Leu Met
865                 870                 875                 880

Asp Thr Ser Gly Tyr Asn Ala Glu Val Arg Val Glu Gly Asn Val Gln
                885                 890                 895

Leu Asn Pro Ile Phe Pro Phe Asp Phe Lys Leu Gly Ser Ser Gly Asp
            900                 905                 910

Asp Arg Gly Lys Val Ile Val Thr Gln Asn Glu Asn Ile Val Tyr Asn
        915                 920                 925
```

```
Ala Met Tyr Glu Ser Phe Ser Ile Ser Phe Trp Ile Arg Ile Asn Lys
            930                 935                 940

Trp Val Ser Asn Leu Pro Gly Tyr Thr Ile Ile Asp Ser Val Lys Asn
945                 950                 955                 960

Asn Ser Gly Trp Ser Ile Gly Ile Ile Ser Asn Phe Leu Val Phe Thr
                965                 970                 975

Leu Lys Gln Asn Glu Asn Ser Glu Gln Asp Ile Asn Phe Ser Tyr Asp
            980                 985                 990

Ile Ser Lys Asn Ala Ala Gly Tyr Asn Lys Trp Phe Phe Val Thr Ile
            995                 1000                1005

Thr Thr Asn Met Met Gly Asn Met Met Ile Tyr Ile Asn Gly Lys
        1010                1015                1020

Leu Ile Asp Thr Ile Lys Val Lys Glu Leu Thr Gly Ile Asn Phe
        1025                1030                1035

Ser Lys Thr Ile Thr Phe Gln Met Asn Lys Ile Pro Asn Thr Gly
        1040                1045                1050

Leu Ile Thr Ser Asp Ser Asp Asn Ile Asn Met Trp Ile Arg Asp
        1055                1060                1065

Phe Tyr Ile Phe Ala Lys Glu Leu Asp Asp Lys Asp Ile Asn Ile
        1070                1075                1080

Leu Phe Asn Ser Leu Gln Tyr Thr Asn Val Val Lys Asp Tyr Trp
        1085                1090                1095

Gly Asn Asp Leu Arg Tyr Asp Lys Glu Tyr Tyr Met Ile Asn Val
        1100                1105                1110

Asn Tyr Met Asn Arg Tyr Met Ser Lys Lys Gly Asn Gly Ile Val
        1115                1120                1125

Phe Asn Thr Arg Lys Asn Asn Asp Phe Asn Glu Gly Tyr Lys
        1130                1135                1140

Ile Ile Ile Lys Arg Ile Arg Gly Asn Thr Asn Asp Thr Arg Val
        1145                1150                1155

Arg Gly Glu Asn Val Leu Tyr Phe Asn Thr Thr Ile Asp Asn Lys
        1160                1165                1170

Gln Tyr Ser Leu Gly Met Tyr Lys Pro Ser Arg Asn Leu Gly Thr
        1175                1180                1185

Asp Leu Val Pro Leu Gly Ala Leu Asp Gln Pro Met Asp Glu Ile
        1190                1195                1200

Arg Lys Tyr Gly Ser Phe Ile Ile Gln Pro Cys Asn Thr Phe Asp
        1205                1210                1215

Tyr Tyr Ala Ser Gln Leu Phe Leu Ser Ser Asn Ala Thr Thr Asn
        1220                1225                1230

Arg Leu Gly Ile Leu Ser Ile Gly Ser Tyr Ser Phe Lys Leu Gly
        1235                1240                1245

Asp Asp Tyr Trp Phe Asn His Glu Tyr Leu Ile Pro Val Ile Lys
        1250                1255                1260

Ile Glu His Tyr Ala Ser Leu Leu Glu Ser Thr Ser Thr His Trp
        1265                1270                1275

Val Phe Val Pro Ala Ser Glu
        1280                1285

<210> SEQ ID NO 9
<211> LENGTH: 3756
<212> TYPE: DNA
<213> ORGANISM: Clostridium botulinum

<400> SEQUENCE: 9
```

```
atgccaaaaa ttaatagttt taattataat gatcctgtta atgatagaac aattttatat      60
attaaaccag gcggttgtca agaattttat aaatcattta atattatgaa aaatatttgg     120
ataattccag agagaaatgt aattggtaca accccccaag attttcatcc gcctacttca     180
ttaaaaaatg gagatagtag ttattatgac cctaattatt tacaaagtga tgaagaaaag     240
gatagatttt taaaaatagt cacaaaaata tttaatagaa taaataataa tctttcagga     300
gggattttat tagaagaact gtcaaaagct aatccatatt tagggaatga taatactcca     360
gataatcaat tccatattgg tgatgcatca gcagttgaga ttaaattctc aaatggtagc     420
caagacatac tattacctaa tgttattata atgggagcag agcctgattt atttgaaact     480
aacagttcca atatttctct aagaaataat tatatgccaa gcaatcaccg ttttggatca     540
atagctatag taacattctc acctgaatat tcttttagat ttaatgataa ttgtatgaat     600
gaatttattc aagatcctgc tcttacatta atgcatgaat taatacattc attacatgga     660
ctatatgggg ctaaagggat tactacaaag tatactataa cacaaaaaca aaatccccta     720
ataacaaata taagaggtac aaatattgaa gaattcttaa cttttggagg tactgattta     780
aacattatta ctagtgctca gtccaatgat atctatacta atcttctagc tgattataaa     840
aaaatagcgt ctaaacttag caaagtacaa gtatctaatc cactacttaa tccttataaa     900
gatgttttg aagcaaagta tggattagat aaagatgcta gcggaattta ttcggtaaat     960
ataaacaaat ttaatgatat ttttaaaaaa ttatacagct ttacggaatt tgatttacga    1020
actaaatttc aagttaaatg taggcaaact tatattggac agtataaata cttcaaactt    1080
tcaaacttgt taaatgattc tatttataat atatcagaag gctataatat aaataattta    1140
aaggtaaatt ttagaggaca gaatgcaaat ttaaatccta gaattattac accaattaca    1200
ggtagaggac tagtaaaaaa aatcattaga ttttgtaaaa atattgtttc tgtaaaaggc    1260
ataaggaaat caatatgtat cgaaataaat aatggtgagt tattttttgt ggcttccgag    1320
aatagttata atgatgataa tataaatact cctaaagaaa ttgacgatac agtaacttca    1380
aataataatt atgaaaatga tttagatcag gttattttaa attttaatag tgaatcagca    1440
cctggacttt cagatgaaaa attaaattta actatccaaa atgatgctta taccaaaa    1500
tatgattcta atggaacaag tgatatagaa caacatgatg ttaatgaact taatgtattt    1560
ttctatttag atgcacagaa agtgcccgaa ggtgaaaata atgtcaatct cacctcttca    1620
attgatacag cattattaga acaacctaaa atatatacat tttttcatc agaatttatt    1680
aataatgtca ataaacctgt gcaagcagca ttatttgtaa gctggataca acaagtgtta    1740
gtagatttta ctactgaagc taaccaaaaa agtactgttg ataaaattgc agatatttct    1800
atagttgttc catatatagg tcttgcttta aatataggaa atgaagcaca aaaaggaaat    1860
tttaaagatg cacttgaatt attaggagca ggtatttat tagaatttga acccgagctt    1920
ttaattccta caatttagt attcacgata aaatcttttt taggttcatc tgataataaa    1980
aataaagtta ttaaagcaat aaataatgca ttgaaagaaa gagatgaaaa atggaaagaa    2040
gtatatagtt ttatagtatc gaattggatg actaaaatta atacacaatt taataaaaga    2100
aaagaacaaa tgtatcaagc tttacaaaat caagtaaatg caattaaaac aataatagaa    2160
tctaagtata atagttatac tttagaggaa aaaaatgagc ttacaaataa atatgatatt    2220
aagcaaatag aaaatgaact taatcaaaag gtttctatag caatgaataa tatagacagg    2280
ttcttaactg aaagttctat atcctatttta atgaaaataa taaatgaagt aaaaattaat    2340
```

-continued

```
aaattaagag aatatgatga gaatgtcaaa acgtatttat tgaattatat tatacaacat    2400
ggatcaatct tgggagagag tcagcaagaa ctaaattcta tggtaactga taccctaaat    2460
aatagtattc cttttaagct ttcttcttat acagatgata aaattttaat ttcatatttt    2520
aataaattct ttaagagaat taaaagtagt tcagttttaa atgagagata taaaaatgat    2580
aaatacgtag atacttcagg atatgattca aatataaata ttaatggaga tgtatataaa    2640
tatccaacta ataaaaatca atttggaata tataatgata aacttagtga agttaatata    2700
tctcaaaatg attacattat atatgataat aaatataaaa attttagtat tagtttttgg    2760
gtaagaattc ctaactatga taataagata gtaaatgtta ataatgaata cactataata    2820
aattgtatga gagataataa ttcaggatgg aaagtatctc ttaatcataa tgaaataatt    2880
tggacattcg aagataatcg aggaattaat caaaaattag catttaacta tggtaacgca    2940
aatggtattt ctgattatat aaataagtgg attttgtaa ctataactaa tgatagatta    3000
ggagattcta aactttatat taatggaaat ttaatagatc aaaaatcaat tttaaattta    3060
ggtaatattc atgttagtga caatatatta tttaaaatag ttaattgtag ttatacaaga    3120
tatattggta ttagatattt taatatttt gataaagaat tagatgaaac agaaaattcaa    3180 actttatata gcaatgaacc taatacaaat attttgaagg attttggggg aaattatttg    3240
ctttatgaca agaatactaa tttattaaat gtgttaaaac caaataactt tattgatagg    3300
agaaaagatt ctactttaag cattaataat ataagaagca ctattctttt agctaataga    3360
ttatatagtg gaataaaagt taaaatacaa agagttaata atagtagtac taacgataat    3420
cttgttagaa agaatgatca ggtatatatt aatttttgtag ccagcaaaac tcacttattt    3480
ccattatatg ctgatacagc taccacaaat aaagagaaaa caataaaaat atcatcatct    3540
ggcaatgatt ttaatcaagt agtagttatg aattcagtag gaaattgtac aatgaatttt    3600
aaaaataata atggaaataa tattgggttg ttaggtttca aggcagatac tgtcgttgct    3660
agtacttggt attatacaca tatgagagat catacaaaca gcaatggatg ttttttggaac    3720 tttatttctg aagaacatgg atggcaagaa aaataa                              3756
```

<210> SEQ ID NO 10
<211> LENGTH: 1251
<212> TYPE: PRT
<213> ORGANISM: Clostridium botulinum

<400> SEQUENCE: 10

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125
```

```
Ala Ser Ala Val Glu Ile Lys Phe Ser Asn Gly Ser Gln Asp Ile Leu
130                 135                 140
Leu Pro Asn Val Ile Ile Met Gly Ala Glu Pro Asp Leu Phe Glu Thr
145                 150                 155                 160
Asn Ser Ser Asn Ile Ser Leu Arg Asn Asn Tyr Met Pro Ser Asn His
                165                 170                 175
Arg Phe Gly Ser Ile Ala Ile Val Thr Phe Ser Pro Glu Tyr Ser Phe
                180                 185                 190
Arg Phe Asn Asp Asn Cys Met Asn Glu Phe Ile Gln Asp Pro Ala Leu
            195                 200                 205
Thr Leu Met His Glu Leu Ile His Ser Leu His Gly Leu Tyr Gly Ala
210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
                245                 250                 255
Gly Thr Asp Leu Asn Ile Ile Thr Ser Ala Gln Ser Asn Asp Ile Tyr
                260                 265                 270
Thr Asn Leu Leu Ala Asp Tyr Lys Lys Ile Ala Ser Lys Leu Ser Lys
            275                 280                 285
Val Gln Val Ser Asn Pro Leu Leu Asn Pro Tyr Lys Asp Val Phe Glu
290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                325                 330                 335
Phe Asp Leu Arg Thr Lys Phe Gln Val Lys Cys Arg Gln Thr Tyr Ile
            340                 345                 350
Gly Gln Tyr Lys Tyr Phe Lys Leu Ser Asn Leu Leu Asn Asp Ser Ile
                355                 360                 365
Tyr Asn Ile Ser Glu Gly Tyr Asn Ile Asn Asn Leu Lys Val Asn Phe
            370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
                405                 410                 415
Ser Val Lys Gly Ile Arg Lys Ser Ile Cys Ile Glu Ile Asn Asn Gly
                420                 425                 430
Glu Leu Phe Phe Val Ala Ser Glu Asn Ser Tyr Asn Asp Asp Asn Ile
            435                 440                 445
Asn Thr Pro Lys Glu Ile Asp Asp Thr Val Thr Ser Asn Asn Asn Tyr
450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                485                 490                 495
Tyr Ile Pro Lys Tyr Asp Ser Asn Gly Thr Ser Asp Ile Glu Gln His
                500                 505                 510
Asp Val Asn Glu Leu Asn Val Phe Phe Tyr Leu Asp Ala Gln Lys Val
            515                 520                 525
Pro Glu Gly Glu Asn Asn Val Asn Leu Thr Ser Ser Ile Asp Thr Ala
530                 535                 540
```

```
Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
            565                 570                 575

Gln Gln Val Leu Val Asp Phe Thr Thr Glu Ala Asn Gln Lys Ser Thr
        580                 585                 590

Val Asp Lys Ile Ala Asp Ile Ser Ile Val Val Pro Tyr Ile Gly Leu
    595                 600                 605

Ala Leu Asn Ile Gly Asn Glu Ala Gln Lys Gly Asn Phe Lys Asp Ala
610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
            645                 650                 655

Ser Asp Asn Lys Asn Lys Val Ile Lys Ala Ile Asn Asn Ala Leu Lys
        660                 665                 670

Glu Arg Asp Glu Lys Trp Lys Glu Val Tyr Ser Phe Ile Val Ser Asn
    675                 680                 685

Trp Met Thr Lys Ile Asn Thr Gln Phe Asn Lys Arg Lys Glu Gln Met
690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
            725                 730                 735

Lys Tyr Asp Ile Lys Gln Ile Glu Asn Glu Leu Asn Gln Lys Val Ser
        740                 745                 750

Ile Ala Met Asn Asn Ile Asp Arg Phe Leu Thr Glu Ser Ser Ile Ser
    755                 760                 765

Tyr Leu Met Lys Ile Ile Asn Glu Val Lys Ile Asn Lys Leu Arg Glu
770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
            805                 810                 815

Asp Thr Leu Asn Asn Ser Ile Pro Phe Lys Leu Ser Ser Tyr Thr Asp
        820                 825                 830

Asp Lys Ile Leu Ile Ser Tyr Phe Asn Lys Phe Phe Lys Arg Ile Lys
    835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
            885                 890                 895

Glu Val Asn Ile Ser Gln Asn Asp Tyr Ile Ile Tyr Asp Asn Lys Tyr
        900                 905                 910

Lys Asn Phe Ser Ile Ser Phe Trp Val Arg Ile Pro Asn Tyr Asp Asn
    915                 920                 925

Lys Ile Val Asn Val Asn Asn Glu Tyr Thr Ile Ile Asn Cys Met Arg
930                 935                 940

Asp Asn Asn Ser Gly Trp Lys Val Ser Leu Asn His Asn Glu Ile Ile
945                 950                 955                 960

Trp Thr Phe Glu Asp Asn Arg Gly Ile Asn Gln Lys Leu Ala Phe Asn
```

```
                   965                 970                 975
Tyr Gly Asn Ala Asn Gly Ile Ser Asp Tyr Ile Asn Lys Trp Ile Phe
                   980                 985                 990
Val Thr Ile Thr Asn Asp Arg Leu  Gly Asp Ser Lys Leu  Tyr Ile Asn
                   995                1000                1005
Gly Asn  Leu Ile Asp Gln Lys  Ser Ile Leu Asn Leu  Gly Asn Ile
        1010                1015                1020
His Val  Ser Asp Asn Ile Leu  Phe Lys Ile Val Asn  Cys Ser Tyr
        1025                1030                1035
Thr Arg  Tyr Ile Gly Ile Arg  Tyr Phe Asn Ile Phe  Asp Lys Glu
        1040                1045                1050
Leu Asp  Glu Thr Glu Ile Gln  Thr Leu Tyr Ser Asn  Glu Pro Asn
        1055                1060                1065
Thr Asn  Ile Leu Lys Asp Phe  Trp Gly Asn Tyr Leu  Leu Tyr Asp
        1070                1075                1080
Lys Glu  Tyr Tyr Leu Leu Asn  Val Leu Lys Pro Asn  Asn Phe Ile
        1085                1090                1095
Asp Arg  Arg Lys Asp Ser Thr  Leu Ser Ile Asn Asn  Ile Arg Ser
        1100                1105                1110
Thr Ile  Leu Leu Ala Asn Arg  Leu Tyr Ser Gly Ile  Lys Val Lys
        1115                1120                1125
Ile Gln  Arg Val Asn Asn Ser  Ser Thr Asn Asp Asn  Leu Val Arg
        1130                1135                1140
Lys Asn  Asp Gln Val Tyr Ile  Asn Phe Val Ala Ser  Lys Thr His
        1145                1150                1155
Leu Phe  Pro Leu Tyr Ala Asp  Thr Ala Thr Thr Asn  Lys Glu Lys
        1160                1165                1170
Thr Ile  Lys Ile Ser Ser Ser  Gly Asn Arg Phe Asn  Gln Val Val
        1175                1180                1185
Val Met  Asn Ser Val Gly Asn  Cys Thr Met Asn Phe  Lys Asn Asn
        1190                1195                1200
Asn Gly  Asn Asn Ile Gly Leu  Leu Gly Phe Lys Ala  Asp Thr Val
        1205                1210                1215
Val Ala  Ser Thr Trp Tyr Tyr  Thr His Met Arg Asp  His Thr Asn
        1220                1225                1230
Ser Asn  Gly Cys Phe Trp Asn  Phe Ile Ser Glu Glu  His Gly Trp
        1235                1240                1245
Gln Glu  Lys
        1250

<210> SEQ ID NO 11
<211> LENGTH: 3843
<212> TYPE: DNA
<213> ORGANISM: Clostridium botulinum

<400> SEQUENCE: 11
atgccagttg taataaatag ttttaattat aatgaccctg ttaatgatga dacaatttta    60
tacatgcaga aaccatatga agaaagaagt agaaaatatt ataaagcttt tgagattatg   120
cctaatgttt ggataatgcc tgagagagat acaataggaa ctaagcctga tgagtttcag   180
gtgccggatt cattaaagaa cggaagtagt gcttattatg atcctaatta tttaaccact   240
gatgctgaaa aagatagata tttaaaaaca atgataaaat tatttaatag aattaatagt   300
aatcctacag ggaaagtttt gttagaagaa gtatcaaatg ctagaccata tttaggagat   360
```

```
gatgacacgc taattaatga attccttcca gttaatgtaa ctacaagtgt taatataaaa    420
ttttcaactg atgttgaaag ttcaataata tcgaatcttc ttgtattggg agcaggacct    480
gatatattta aagcttactg tacccccctt gtaaggttta ataagtcaga taaattaatt    540
gaaccaagta atcatggttt tggatcaatt aatatcttga cattttcacc tgagtatgaa    600
catattttta atgatattag tggagggaat cataatagta cagaatcatt tattgcagat    660
cctgcaattt cactagctca tgaattgata catgcactac atggattata cggggctaag    720
gcagttactc ataaagagtc tctagtagca gagcgaggac ctcttatgat agccgaaaag    780
cccataaggc tagaagaatt tttaactttt ggaggtgagg atttaaatat cattcctagt    840
gctatgaagg aaaaaatata taacgatctt ttagctaact atgaaaaaat agctactaga    900
cttagagaag ttaatacggc tcctcctgga tatgatatta atgaatataa agattatttt    960
caatggaagt atggactaga tagaaatgca gatggaagtt atactgtgaa tagaaataaa   1020
tttaatgaaa tttataaaaa attatatagc tttacagaga ttgacttagc aaataaattt   1080
aaagtaaaat gtagaaatac ttattttatt aaatatggat ttgtaaaagt tccaaatttg   1140
ttagatgatg atatttatac tgtatcagag gggtttaata taggtaattt agcagtaaac   1200
aatcgcggac aaaatataaa tttaaatcct aaaattattg attccattcc agataaaggt   1260
ttagtggaaa agattattaa attttgtaag agcattattc ctagaaaagg tacgaagcag   1320
tcaccgtcac tatgcattag agtaaataat agggagttat ttttgtagc ttcagaaagt   1380 agctataatg aaagtgatat taatacacct aaagaaattg acgatacaac aaatctaaat   1440
aataattata gaaataattt agatgaagtt attttagatt ataatagtga gacaataacct   1500 caaatatcaa atcgaacatt aaatacactt gtacaagaca atagttatgt gccaagatat   1560
gattctaatg aacaagtgaa aatagaggaa tatgatgttg ttgactttaa tgtatttttc   1620
tatttacatg cacaaaaagt accagaaggt gaaaccaata taagtttaac ttcttcaatt   1680
gatacagcat tattgaaga atccaaagta tatacatttt tttcttcaga gtttatcgat   1740
actatcaata aacctgtaaa tgcagcacta tttatagatt ggataagcaa agtaataaga   1800
gattttacca ctgaagctac acaaaaaagt actgttgata agattgcaga catatcttta   1860
attgtaccct atgtaggtct tgctttgaat atagttattg aggcagaaaa aggaaatttt   1920
gaggaggcat ttgaattatt aggagcgggt attttattag aatttgtgcc agagcttaca   1980
attcctgtaa ttttagtgtt tacgataaaa tcctatatag attcatatga gaataaaaat   2040
aaagcaatta aagcaataaa taattcatta atcgaaagag aagcaaagtg gaaagaaata   2100
tatagttgga tagtatcaaa ttggcttact agaattaata cgcaatttaa taaaagaaaa   2160
gagcaaatgt atcaggcttt acaaaatcaa gtagatgcaa taaaaacagc aatagaaatat  2220 aaatataata attatacttc agatgagaaa aatagacttg aatctaaata taatatcaat   2280
aatatagaag aagaattgaa taaaaaagtt tctttagcaa tgaaaaatat agaaagattt   2340
atgacagaaa gttctatatc ttatttaatg aaattaataa atgaagccga agttggtaaa   2400
ttaaaagaat atgataaaca tgttaagagc gatttattag actatattct ctaccataaa   2460
ttaatcttag gagagcagac aaaggaatta attgatttgg tgactagtac tttgaatagt   2520
agtattccat ttgaactttc ttcatatact aatgataaaa ttctaattat atattttaat   2580
agattatata aaaaaattaa agatagttct attttagata tgcgatatga aaataataaa   2640
tttatagata tctctggata tggttcaaat ataagcatta atggaaacgt atatatttat   2700
tcaacaaata gaaatcaatt tggaatatat agtggtaggc ttagtgaagt taatatagct   2760
```

-continued

```
caaaataatg atattatata caatagtaga tatcaaaatt ttagtattag tttctgggta    2820
accattccta aacactacag acctatgaat cgtaatcggg aatacactat aataaattgt    2880
atggggaata taattcggg atggaaaata tcacttagaa ctattagaga ttgtgaaata     2940
atttggactt tacaagatac ttccggaaat aaggaaaaat taattttag gtatgaagaa     3000 cttgctagta tatctgatta tataaataaa tggattttg taactattac taataataga    3060
ttaggcaatt ctagaattta catcaatgga aatttaatag ttgaaaaatc aatttcgaat    3120
ttaggtgata ttcatgttag tgataatata ttatttaaaa ttgttggttg tgatgatgaa    3180
acgtatgttg gtataagata ttttaaagtt tttaatacgg aattagataa aacagaaatt    3240
gagactttat atagtaatga gccagatcca agtatcttaa aagactattg gggaaattat    3300
ttgctatata ataaaaaata ttatttattc aatttactaa gaaagataa gtatattact    3360 cggaattcag gcattttaaa tattaatcaa caaagaggtg ttactggagg catatctgtt    3420
tttttgaact ataattata tgaaggagta gaagttatta taagaaaaaa tgctcctata    3480
gatatatcta atacagataa ttttgttaga aaaaacgatc tagcatacat taatgtagta    3540
gatcatggtg tagaatatcg gttatatgct gatatatcaa ttacaaaatc agagaaaata    3600
ataaaattaa taagaacatc taatccaaac gatagcttag gtcaaattat agttatggat    3660
tcaataggaa ataattgcac aatgaattt caaaacaatg atgggagcaa taggatta     3720 ctaggttttc attcagatga tttggttgct agtagttggt attataacca tatacgaaga    3780
aacactagca gtaatggatg cttttggagt tttatttcta aagagcatgg ttggaaagaa    3840
taa                                                                  3843
```

<210> SEQ ID NO 12
<211> LENGTH: 1280
<212> TYPE: PRT
<213> ORGANISM: Clostridium botulinum

<400> SEQUENCE: 12

```
Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Arg Ser Arg Lys
            20                  25                  30

Tyr Tyr Lys Ala Phe Glu Ile Met Pro Asn Val Trp Ile Met Pro Glu
        35                  40                  45

Arg Asp Thr Ile Gly Thr Lys Pro Asp Glu Phe Gln Val Pro Asp Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Met Ile Lys Leu Phe Asn
                85                  90                  95

Arg Ile Asn Ser Asn Pro Thr Gly Lys Val Leu Leu Glu Glu Val Ser
            100                 105                 110

Asn Ala Arg Pro Tyr Leu Gly Asp Asp Asp Thr Leu Ile Asn Glu Phe
        115                 120                 125

Leu Pro Val Asn Val Thr Thr Ser Val Asn Ile Lys Phe Ser Thr Asp
    130                 135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165                 170                 175
```

```
Asp Lys Leu Ile Glu Pro Ser Asn His Gly Phe Gly Ser Ile Asn Ile
                180                 185                 190

Leu Thr Phe Ser Pro Glu Tyr Glu His Ile Phe Asn Asp Ile Ser Gly
            195                 200                 205

Gly Asn His Asn Ser Thr Glu Ser Phe Ile Ala Asp Pro Ala Ile Ser
        210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245                 250                 255

Ile Ala Glu Lys Pro Ile Arg Leu Glu Glu Phe Leu Thr Phe Gly Gly
            260                 265                 270

Glu Asp Leu Asn Ile Ile Pro Ser Ala Met Lys Glu Lys Ile Tyr Asn
        275                 280                 285

Asp Leu Leu Ala Asn Tyr Glu Lys Ile Ala Thr Arg Leu Arg Glu Val
    290                 295                 300

Asn Thr Ala Pro Pro Gly Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
                325                 330                 335

Asn Arg Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
                405                 410                 415

Pro Asp Lys Gly Leu Val Glu Lys Ile Ile Lys Phe Cys Lys Ser Ile
            420                 425                 430

Ile Pro Arg Lys Gly Thr Lys Gln Ser Pro Ser Leu Cys Ile Arg Val
        435                 440                 445

Asn Asn Arg Glu Leu Phe Phe Val Ala Ser Glu Ser Ser Tyr Asn Glu
    450                 455                 460

Ser Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
        515                 520                 525

Glu Glu Tyr Asp Val Val Asp Phe Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Val Tyr Thr Phe Phe Ser Ser
                565                 570                 575

Glu Phe Ile Asp Thr Ile Asn Lys Pro Val Asn Ala Ala Leu Phe Ile
            580                 585                 590
```

-continued

Asp Trp Ile Ser Lys Val Ile Arg Asp Phe Thr Thr Glu Ala Thr Gln
            595                 600                 605

Lys Ser Thr Val Asp Lys Ile Ala Asp Ile Ser Leu Ile Val Pro Tyr
    610                 615                 620

Val Gly Leu Ala Leu Asn Ile Val Ile Glu Ala Glu Lys Gly Asn Phe
625                 630                 635                 640

Glu Glu Ala Phe Glu Leu Leu Gly Ala Gly Ile Leu Leu Glu Phe Val
                645                 650                 655

Pro Glu Leu Thr Ile Pro Val Ile Leu Val Phe Thr Ile Lys Ser Tyr
                660                 665                 670

Ile Asp Ser Tyr Glu Asn Lys Asn Lys Ala Ile Lys Ala Ile Asn Asn
    675                 680                 685

Ser Leu Ile Glu Arg Glu Ala Lys Trp Lys Glu Ile Tyr Ser Trp Ile
    690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Ala Ile Glu Tyr Lys Tyr Asn Asn Tyr Thr Ser Asp Glu Lys Asn Arg
                740                 745                 750

Leu Glu Ser Lys Tyr Asn Ile Asn Asn Ile Glu Glu Glu Leu Asn Lys
                755                 760                 765

Lys Val Ser Leu Ala Met Lys Asn Ile Glu Arg Phe Met Thr Glu Ser
770                 775                 780

Ser Ile Ser Tyr Leu Met Lys Leu Ile Asn Glu Ala Glu Val Gly Lys
785                 790                 795                 800

Leu Lys Glu Tyr Asp Lys His Val Lys Ser Asp Leu Leu Asp Tyr Ile
                805                 810                 815

Leu Tyr His Lys Leu Ile Leu Gly Glu Gln Thr Lys Glu Leu Ile Asp
                820                 825                 830

Leu Val Thr Ser Thr Leu Asn Ser Ser Ile Pro Phe Glu Leu Ser Ser
                835                 840                 845

Tyr Thr Asn Asp Lys Ile Leu Ile Ile Tyr Phe Asn Arg Leu Tyr Lys
850                 855                 860

Lys Ile Lys Asp Ser Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asn
                885                 890                 895

Val Tyr Ile Tyr Ser Thr Asn Arg Asn Gln Phe Gly Ile Tyr Ser Gly
                900                 905                 910

Arg Leu Ser Glu Val Asn Ile Ala Gln Asn Asn Asp Ile Ile Tyr Asn
                915                 920                 925

Ser Arg Tyr Gln Asn Phe Ser Ile Ser Phe Trp Val Thr Ile Pro Lys
                930                 935                 940

His Tyr Arg Pro Met Asn Arg Asn Arg Glu Tyr Thr Ile Ile Asn Cys
945                 950                 955                 960

Met Gly Asn Asn Asn Ser Gly Trp Lys Ile Ser Leu Arg Thr Ile Arg
                965                 970                 975

Asp Cys Glu Ile Ile Trp Thr Leu Gln Asp Thr Ser Gly Asn Lys Glu
                980                 985                 990

Lys Leu Ile Phe Arg Tyr Glu Glu Leu Ala Ser Ile Ser Asp Tyr Ile
                995                 1000                1005

Asn Lys Trp Ile Phe Val Thr Ile Thr Asn Asn Arg Leu Gly Asn

| | | | | | | | | | | | |
|---|---|---|---|---|---|---|---|---|---|---|---|
| Ser | Arg | Ile | Tyr | Ile | Asn | Gly | Asn | Leu | Ile | Val | Glu | Lys | Ser | Ile |
| 1025 | | | | | 1030 | | | | | 1035 | | | | |
| Ser | Asn | Leu | Gly | Asp | Ile | His | Val | Ser | Asp | Asn | Ile | Leu | Phe | Lys |
| 1040 | | | | | 1045 | | | | | 1050 | | | | |
| Ile | Val | Gly | Cys | Asp | Asp | Glu | Thr | Tyr | Val | Gly | Ile | Arg | Tyr | Phe |
| 1055 | | | | | 1060 | | | | | 1065 | | | | |
| Lys | Val | Phe | Asn | Thr | Glu | Leu | Asp | Lys | Thr | Glu | Ile | Glu | Thr | Leu |
| 1070 | | | | | 1075 | | | | | 1080 | | | | |
| Tyr | Ser | Asn | Glu | Pro | Asp | Pro | Ser | Ile | Leu | Lys | Asp | Tyr | Trp | Gly |
| 1085 | | | | | 1090 | | | | | 1095 | | | | |
| Asn | Tyr | Leu | Leu | Tyr | Asn | Lys | Lys | Tyr | Tyr | Leu | Phe | Asn | Leu | Leu |
| 1100 | | | | | 1105 | | | | | 1110 | | | | |
| Arg | Lys | Asp | Lys | Tyr | Ile | Thr | Arg | Asn | Ser | Gly | Ile | Leu | Asn | Ile |
| 1115 | | | | | 1120 | | | | | 1125 | | | | |
| Asn | Gln | Gln | Arg | Gly | Val | Thr | Gly | Gly | Ile | Ser | Val | Phe | Leu | Asn |
| 1130 | | | | | 1135 | | | | | 1140 | | | | |
| Tyr | Lys | Leu | Tyr | Glu | Gly | Val | Glu | Val | Ile | Ile | Arg | Lys | Asn | Ala |
| 1145 | | | | | 1150 | | | | | 1155 | | | | |
| Pro | Ile | Asp | Ile | Ser | Asn | Thr | Asp | Asn | Phe | Val | Arg | Lys | Asn | Asp |
| 1160 | | | | | 1165 | | | | | 1170 | | | | |
| Leu | Ala | Tyr | Ile | Asn | Val | Val | Asp | His | Gly | Val | Glu | Tyr | Arg | Leu |
| 1175 | | | | | 1180 | | | | | 1185 | | | | |
| Tyr | Ala | Asp | Ile | Ser | Ile | Thr | Lys | Ser | Glu | Lys | Ile | Ile | Lys | Leu |
| 1190 | | | | | 1195 | | | | | 1200 | | | | |
| Ile | Arg | Thr | Ser | Asn | Pro | Asn | Asp | Ser | Leu | Gly | Gln | Ile | Ile | Val |
| 1205 | | | | | 1210 | | | | | 1215 | | | | |
| Met | Asp | Ser | Ile | Gly | Asn | Asn | Cys | Thr | Met | Asn | Phe | Gln | Asn | Asn |
| 1220 | | | | | 1225 | | | | | 1230 | | | | |
| Asp | Gly | Ser | Asn | Ile | Gly | Leu | Leu | Gly | Phe | His | Ser | Asp | Asp | Leu |
| 1235 | | | | | 1240 | | | | | 1245 | | | | |
| Val | Ala | Ser | Ser | Trp | Tyr | Tyr | Asn | His | Ile | Arg | Arg | Asn | Thr | Ser |
| 1250 | | | | | 1255 | | | | | 1260 | | | | |
| Ser | Asn | Gly | Cys | Phe | Trp | Ser | Phe | Ile | Ser | Lys | Glu | His | Gly | Trp |
| 1265 | | | | | 1270 | | | | | 1275 | | | | |
| Lys | Glu | | | | | | | | | | | | | |
| 1280 | | | | | | | | | | | | | | |

```
<210> SEQ ID NO 13
<211> LENGTH: 3894
<212> TYPE: DNA
<213> ORGANISM: Clostridium botulinum
<220> FEATURE:
<221> NAME/KEY: misc_feature
<222> LOCATION: (20)..(20)
<223> OTHER INFORMATION: n is a, c, g, or t

<400> SEQUENCE: 13
```

| | |
|---|---|
| atgccagtta atataaaaan ctttaattat aatgacccta ttaataatga tgacattatt | 60 |
| atgatggaac cattcaatga cccagggcca ggaacatatt ataaagcttt taggattata | 120 |
| gatcgtattt ggatagtacc agaaaggttt acttatggat ttcaacctga ccaatttaat | 180 |
| gccagtacag agttttttag taaagatgtc tacgaatatt acgatccaac ttatttaaaa | 240 |
| accgatgctg aaaagataa attttttaaaa acaatgatta aattatttaa tagaattaat | 300 |
| tcaaaaccat caggacagag attactggat atgatagtag atgctatacc ttatcttgga | 360 |

```
aatgcatcta caccgcccga caaatttgca gcaaatgttg caaatgtatc tattaataaa    420
aaaattatcc aacctggagc tgaagatcaa ataaaaggtt taatgacaaa tttaataata    480
tttggaccag gaccagttct aagtgataat tttactgata gtatgattat gaatggccat    540
tccccaatat cagaaggatt tggtgcaaga atgatgataa gattttgtcc tagttgttta    600
aatgtattta ataatgttca ggaaaataaa gatacatcta tatttagtag acgcgcgtat    660
tttgcagatc cagctctaac gttaatgcat gaacttatac atgtgttaca tggattatat    720
ggaattaaga taagtaattt accaattact ccaaatacaa agaattttt catgcaacat    780 agcgatcctg tacaagcaga agaactatat acattcggag gacatgatcc tagtgttata    840
agtccttcta cggatatgaa tatttataat aaagcgttac aaaattttca agatatagct    900
aataggctta atattgtttc aagtgcccaa gggagtggaa ttgatatttc cttatataaa    960
caaatatata aaaataaata tgattttgtt gaagatccta atggaaaata tagtgtagat   1020
aaggataagt ttgataaatt atataaggcc ttaatgtttg gcttactga aactaatcta   1080 gctggtgaat atggaataaa aactaggtat tcttatttta gtgaatattt gccaccgata   1140
aaaactgaaa aattgttaga caatacaatt tatactcaaa atgaaggctt taacatagct   1200
agtaaaaatc tcaaaacgga atttaatggt cagaataagg cggtaaataa agaggcttat   1260
gaagaaatca gcctagaaca tctcgttata tatagaatag caatgtgcaa gcctgtaatg   1320
tacaaaaata ccggtaaatc tgaacagtgt attattgtta ataatgagga tttatttttc   1380
atagctaata aagatagttt ttcaaaagat ttagctaaag cagaaactat agcatataat   1440
acacaaaata atactataga aaataatttt tctatagatc agttgatttt agataatgat   1500
ttaagcagtg gcatagactt accaaatgaa aacacagaac catttacaaa ttttgacgac   1560
atagatatcc ctgtgtatat taaacaatct gctttaaaaa aaattttgt ggatggagat   1620 agccttttg aatatttaca tgctcaaaca tttccttcta atatagaaaa tctacaacta   1680
acgaattcat taaatgatgc tttaagaaat aataataaag tctatacttt tttttctaca   1740
aaccttgttg aaaaagctaa tacagttgta ggtgcttcac tttttgtaaa ctgggtaaaa   1800
ggagtaatag atgattttac atctgaatcc acacaaaaaa gtactataga taagtttca   1860 gatgtatcca taattattcc ctatatagga cctgctttga atgtaggaaa tgaaacagct   1920
aaagaaaatt ttaaaaatgc ttttgaaata ggtggagccg ctatcttaat ggagtttatt   1980
ccagaactta ttgtacctat agttggattt tttacattag aatcatatgt aggaaataaa   2040
gggcatatta ttatgacgat atccaatgct ttaaagaaaa gggatcaaaa atggacagat   2100
atgtatggtt tgatagtatc gcagtggctc tcaacggtta atactcaatt ttatacaata   2160
aaagaaagaa tgtacaatgc tttaaataat caatcacaag caatagaaaa aataatagaa   2220
gatcaatata atagatatag tgaagaagat aaaatgaata ttaacattga ttttaatgat   2280
atagatttta aacttaatca aagtataaat ttagcaataa acaatataga tgatttttata  2340 aaccaatgtt ctatatcata tctaatgaat agaatgattc cattagctgt aaaaaagtta   2400
aaagactttg atgataatct taagagagat ttattggagt atatagatac aaatgaacta   2460
tatttacttg atgaagtaaa tattctaaaa tcaaaagtaa atagacacct aaaagacagt   2520
ataccatttg atctttcact atataccaag gacacaattt taatacaagt ttttaataat   2580
tatattagta atattagtag taatgctatt ttaagtttaa gttatagagg tgggcgttta   2640
atagattcat ctggatatgg tgcaactatg aatgtaggtt cagatgttat ctttaatgat   2700
```

-continued

```
ataggaaatg gtcaatttaa attaaataat tctgaaaata gtaatattac ggcacatcaa    2760
agtaaattcg ttgtatatga tagtatgttt gataatttta gcattaactt ttgggtaagg    2820
actcctaaat ataataataa tgatatacaa acttatcttc aaaatgagta tacaataatt    2880
agttgtataa aaaatgactc aggatggaaa gtatctatta agggaaatag aataatatgg    2940
acattaatag atgttaatgc aaaatctaaa tcaatatttt tcgaatatag tataaaagat    3000
aatatatcag attatataaa taatggtttt tccataacta ttactaatga tagattaggt    3060
aacgcaaata tttatataaa tggaagtttg aaaaaaagtg aaaaaatttt aaacttagat    3120
agaattaatt ctagtaatga tatagacttc aaattaatta attgtacaga tactactaaa    3180
tttgtttgga ttaaggattt taatattttt ggtagagaat aaatgctac agaagtatct     3240 tcactatatt ggattcaatc atctacaaat actttaaaag attttgggg gaatcccttta    3300 agatacgata cacaatacta tctgtttaat caaggtatgc aaaatatcta tataaagtat    3360
tttagtaaag cttctatggg ggaaactgca ccacgtacaa actttaataa tgcagcaata    3420
aattatcaaa atttatatct tggtttacga tttattataa aaaaagcatc aaattctcgg    3480
aatataaata atgataatat agtcagagaa ggagattata tatatcttaa tattgataat    3540
atttctgatg aatcttacag agtatatgtt ttggtgaatt ctaaagaaat tcaaactcaa    3600 ttattttttag cacccataaa tgatgatcct acgttctatg atgtactaca aataaaaaaa    3660
tattatgaaa aaacaacata taattgtcag atactttgcg aaaaagatac taaaacatttt   3720 gggctgtttg gaattggtaa atttgttaaa gattatggat atgtttggga tacctatgat    3780 aattatttttt gcataagtca gtggtatctc agaagaatat ctgaaaatat aaataaatta   3840
aggttgggat gtaattggca attcattccc gtggatgaag gatggacaga ataa          3894
```

<210> SEQ ID NO 14
<211> LENGTH: 1297
<212> TYPE: PRT
<213> ORGANISM: Clostridium botulinum
<220> FEATURE:
<221> NAME/KEY: MISC_FEATURE
<222> LOCATION: (7)..(7)
<223> OTHER INFORMATION: Xaa can be any naturally occurring amino acid

<400> SEQUENCE: 14

```
Met Pro Val Asn Ile Lys Xaa Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140
```

```
Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
        435                 440                 445

Gln Cys Ile Ile Val Asn Asn Glu Asp Leu Phe Phe Ile Ala Asn Lys
    450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
        515                 520                 525

Gln Ser Ala Leu Lys Lys Ile Phe Val Asp Gly Asp Ser Leu Phe Glu
    530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
```

```
            565                 570                 575
Phe Phe Ser Thr Asn Leu Val Glu Lys Ala Asn Thr Val Val Gly Ala
            580                 585                 590

Ser Leu Phe Val Asn Trp Val Lys Gly Val Ile Asp Phe Thr Ser
            595                 600             605

Glu Ser Thr Gln Lys Ser Thr Ile Asp Lys Val Ser Asp Val Ser Ile
            610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
            660                 665                 670

Leu Glu Ser Tyr Val Gly Asn Lys Gly His Ile Ile Met Thr Ile Ser
            675                 680                 685

Asn Ala Leu Lys Lys Arg Asp Gln Lys Trp Thr Asp Met Tyr Gly Leu
            690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
            740                 745                 750

Asn Ile Asn Ile Asp Phe Asn Asp Ile Asp Phe Lys Leu Asn Gln Ser
            755                 760                 765

Ile Asn Leu Ala Ile Asn Asn Ile Asp Asp Phe Ile Asn Gln Cys Ser
770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
            805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
            835                 840                 845

Thr Lys Asp Thr Ile Leu Ile Gln Val Phe Asn Asn Tyr Ile Ser Asn
            850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
            915                 920                 925

Met Phe Asp Asn Phe Ser Ile Asn Phe Trp Val Arg Thr Pro Lys Tyr
            930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
            980                 985                 990
```

```
Phe Phe Glu Tyr Ser Ile Lys Asp Asn Ile Ser Asp Tyr Ile Asn Lys
        995                 1000                1005

Trp Phe Ser Ile Thr Ile Thr Asn Asp Arg Leu Gly Asn Ala Asn
    1010                1015                1020

Ile Tyr Ile Asn Gly Ser Leu Lys Lys Ser Glu Lys Ile Leu Asn
    1025                1030                1035

Leu Asp Arg Ile Asn Ser Ser Asn Asp Ile Asp Phe Lys Leu Ile
    1040                1045                1050

Asn Cys Thr Asp Thr Thr Lys Phe Val Trp Ile Lys Asp Phe Asn
    1055                1060                1065

Ile Phe Gly Arg Glu Leu Asn Ala Thr Glu Val Ser Ser Leu Tyr
    1070                1075                1080

Trp Ile Gln Ser Ser Thr Asn Thr Leu Lys Asp Phe Trp Gly Asn
    1085                1090                1095

Pro Leu Arg Tyr Asp Thr Gln Tyr Tyr Leu Phe Asn Gln Gly Met
    1100                1105                1110

Gln Asn Ile Tyr Ile Lys Tyr Phe Ser Lys Ala Ser Met Gly Glu
    1115                1120                1125

Thr Ala Pro Arg Thr Asn Phe Asn Asn Ala Ala Ile Asn Tyr Gln
    1130                1135                1140

Asn Leu Tyr Leu Gly Leu Arg Phe Ile Ile Lys Lys Ala Ser Asn
    1145                1150                1155

Ser Arg Asn Ile Asn Asn Asp Asn Ile Val Arg Glu Gly Asp Tyr
    1160                1165                1170

Ile Tyr Leu Asn Ile Asp Asn Ile Ser Asp Glu Ser Tyr Arg Val
    1175                1180                1185

Tyr Val Leu Val Asn Ser Lys Glu Ile Gln Thr Gln Leu Phe Leu
    1190                1195                1200

Ala Pro Ile Asn Asp Asp Pro Thr Phe Tyr Asp Val Leu Gln Ile
    1205                1210                1215

Lys Lys Tyr Tyr Glu Lys Thr Thr Tyr Asn Cys Gln Ile Leu Cys
    1220                1225                1230

Glu Lys Asp Thr Lys Thr Phe Gly Leu Phe Gly Ile Gly Lys Phe
    1235                1240                1245

Val Lys Asp Tyr Gly Tyr Val Trp Asp Thr Tyr Asp Asn Tyr Phe
    1250                1255                1260

Cys Ile Ser Gln Trp Tyr Leu Arg Arg Ile Ser Glu Asn Ile Asn
    1265                1270                1275

Lys Leu Arg Leu Gly Cys Asn Trp Gln Phe Ile Pro Val Asp Glu
    1280                1285                1290

Gly Trp Thr Glu
    1295

<210> SEQ ID NO 15
<211> LENGTH: 4400
<212> TYPE: DNA
<213> ORGANISM: Clostridium tetani

<400> SEQUENCE: 15
tagcattaaa aaaattagaa cctatagtaa ataaattaat taatatatag ttttttataat    60 ttaattatga ataatattct taagataaaa agtaaatttt taaaaattta aattttcagt   120
ttacaaaaaa taacctgatt atgttatatg taattgtaaa aaacatataa aaaatcagaa   180
aaatttagga ggtatattat taatggatta ataataatt ttttaattta cttttgatta   240
```

```
ataaatatta aatgtttatt ttaattagga gatgatacgt atgccaataa ccataaataa    300
ttttagatat agtgatcctg ttaataatga tacaattatt atgatggagc caccatactg    360
taagggtcta gatatctatt ataaggcttt caaaataaca gatcgtattt ggatagtgcc    420
ggaaaggtat gaatttggga caaaacctga agattttaac ccaccatctt cattaataga    480
aggtgcatct gagtattacg atccaaatta tttaaggact gattctgata agatagatt     540 tttacaaacc atggtaaaac tgtttaacag aattaaaaac aatgtagcag gtgaagcctt    600
attagataag ataataaatg ccatacctta ccttggaaat tcatattcct tactagacaa    660
gtttgataca aactctaatt cagtatcttt taatttatta gaacaagacc ccagtggagc    720
aactacaaaa tcagcaatgc tgacaaattt aataatattt ggacctgggc ctgttttaaa    780
taaaaatgag gttagaggta ttgtattgag ggtagataat aaaaattact tcccatgtag    840
agatggtttt ggctcaataa tgcaaatggc attttgccca gaatatgtac ctacctttga    900
taatgtaata gaaaatatta cgtcactcac tattggcaaa agcaaatatt ttcaagatcc    960
agcattacta ttaatgcacg aacttataca tgtactacat ggtttatacg gaatgcaggt   1020
atcaagccat gaaattattc catccaaaca agaaatttat atgcagcata catatccaat   1080
aagtgctgaa gaactattca cttttggcgg acaggatgct aatcttataa gtattgatat   1140
aaaaaacgat ttatatgaaa aaactttaaa tgattataaa gctatagcta acaaacttag   1200
tcaagtcact agctgcaatg atcccaacat tgatattgat agctacaaac aaatatatca   1260
acaaaaatat caattcgata agatagcaa tggacaatat attgtaaatg aggataaatt    1320
tcagatacta tataatagca taatgtatgg ttttacagag attgaattgg gaaaaaaatt   1380
taatataaaa actagacttt cttattttag tatgaatcat gaccctgtaa aaattccaaa   1440
tttattagat gatacaattt acaatgatac agaaggattt aatatagaaa gcaaagatct   1500
gaaatctgaa tataaaggac aaaatatgag ggtaaataca aatgctttta gaatgttga    1560 tggatcaggc ctagttttcaa aacttattgg cttatgtaaa aaaattatac caccaacaaa   1620
tataagagaa aatttatata atagaactgc atcattaaca gatttaggag gagaattatg   1680
tataaaaatt aaaaatgaag atttaacttt tatagctgaa aaaaatagct ttcagaaga    1740 accatttcaa gatgaaatag ttagttataa tacaaaaaat aaaccattaa attttaatta   1800
ttcgctagat aaaattattg tagattataa tctacaaagt aaaattacat tacctaatga   1860
taggacaacc ccagttacaa aaggaattcc atatgctcca gaatataaaa gtaatgctgc   1920
aagtacaata gaaatacata atattgatga caatacaata tatcaatatt tgtatgctca   1980
aaaatctcct acaactctac aaagaataac tatgactaat tctgttgatg acgcattaat   2040
aaattccacc aaaatatatt catattttcc atctgtaatc agtaaagtta ccaaggtgc    2100 acaaggaatt ttattcttac agtgggtgag agatataatt gatgattta ccaatgaatc    2160 ttcacaaaaa actactattg ataaaatttc agatgtatcc actattgttc cttatatagg   2220
acccgcatta acattgtaa acaaggcta tgagggaaac tttataggcg ctttagaaac     2280
taccggagtg gttttattat tagaatatat tccagaaatt actttaccag taattgcagc   2340
tttatctata gcagaaagta gcacacaaaa agaaagata ataaaacaa tagataactt     2400 tttagaaaaa agatatgaaa aatggattga agtatataaa ctagtaaaag caaaatggtt   2460
aggcacagtt aatacgcaat tccaaaaaag aagttatcaa atgtatagat ctttagaata   2520
tcaagtagat gcaataaaaa aaataataga ctatgaatat aaaatatatt caggacctga   2580
```

```
taaggaacaa attgccgacg aaattaataa tctgaaaaac aaacttgaag aaaaggctaa    2640
taaagcaatg ataaacataa atatatttat gagggaaagt tctagatcat ttttagttaa    2700
tcaaatgatt aacgaagcta aaaagcagtt attagagttt gatactcaaa gcaaaaatat    2760
tttaatgcag tatataaaag caaattctaa atttataggt ataactgaac taaaaaaatt    2820
agaatcaaaa ataaacaaag ttttttcaac accaattcca ttttcttatt ctaaaaatct    2880
ggattgttgg gttgataatg aagaagatat agatgttata ttaaaaaaga gtacaatttt    2940
aaatttagat attaataatg atattatatc agatatatct gggtttaatt catctgtaat    3000
aacatatcca gatgctcaat tggtgcccgg aataaatggc aaagcaatac atttagtaaa    3060
caatgaatct tctgaagtta tagtgcataa agctatggat attgaatata atgatatgtt    3120
taataatttt accgttagct tttggttgag ggttcctaaa gtatctgcta gtcatttaga    3180
acaatatggc acaaatgagt attcaataat tagctctatg aaaaaacata gtctatcaat    3240
aggatctggt tggagtgtat cacttaaagg taataactta atatggactt taaaagattc    3300
cgcgggagaa gttagacaaa taacttttag ggatttacct gataaattta atgcttattt    3360
agcaaataaa tgggttttta taactattac taatgataga ttatcttctg ctaatttgta    3420
tataaatgga gtacttatgg gaagtgcaga aattactggt ttaggagcta ttagagagga    3480
taataatata acattaaaac tagatagatg taataataat aatcaatacg tttctattga    3540
taaatttagg atattttgca aagcattaaa tccaaaagag attgaaaaat tatacacaag    3600
ttatttatct ataaccttt taagagactt ctggggaaac cctttacgat atgatacaga    3660
atattattta ataccagtag cttctagttc taaagatgtt caattgaaaa atataacaga    3720
ttatatgtat ttgacaaatg cgccatcgta tactaacgga aaattgaata tatattatag    3780
aaggttatat aatggactaa aatttattat aaaaagatat acacctaata atgaaataga    3840
ttcttttgtt aaatcaggtg attttattaa attatatgta tcatataaca ataatgagca    3900
cattgtaggt tatccgaaag atggaaatgc ctttaataat cttgatagaa ttctaagagt    3960
aggttataat gccccaggta tccctctttta taaaaaaatg gaagcagtaa aattgcgtga    4020
tttaaaaacc tattctgtac aacttaaatt atatgatgat aaaaatgcat ctttaggact    4080
agtaggtacc cataatggtc aaataggcaa cgatccaaat agggatatat aattgcaag    4140 caactggtac tttaatcatt taaaagataa aattttagga tgtgattggt actttgtacc    4200
tacagatgaa ggatggacaa atgattaaac agattgatat gttcatgatt actctatata    4260
aaaaattaaa taatataaca atctagctat attattttg attatttct taatatatac    4320 taataaaata atcaaaatag agcctatctt aaattactga agggctgtgt caaaataaga    4380
ttttgacaca gcctctactt                                                4400
```

<210> SEQ ID NO 16
<211> LENGTH: 1315
<212> TYPE: PRT
<213> ORGANISM: Clostridium tetani

<400> SEQUENCE: 16

```
Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45
```

-continued

```
Arg Tyr Glu Phe Gly Thr Lys Pro Glu Asp Phe Asn Pro Pro Ser Ser
 50                  55                  60
Leu Ile Glu Gly Ala Ser Glu Tyr Tyr Asp Pro Asn Tyr Leu Arg Thr
 65                  70                  75                  80
Asp Ser Asp Lys Asp Arg Phe Leu Gln Thr Met Val Lys Leu Phe Asn
                 85                  90                  95
Arg Ile Lys Asn Asn Val Ala Gly Glu Ala Leu Leu Asp Lys Ile Ile
                100                 105                 110
Asn Ala Ile Pro Tyr Leu Gly Asn Ser Tyr Ser Leu Leu Asp Lys Phe
                115                 120                 125
Asp Thr Asn Ser Asn Ser Val Ser Phe Asn Leu Leu Glu Gln Asp Pro
130                 135                 140
Ser Gly Ala Thr Thr Lys Ser Ala Met Leu Thr Asn Leu Ile Ile Phe
145                 150                 155                 160
Gly Pro Gly Pro Val Leu Asn Lys Asn Glu Val Arg Gly Ile Val Leu
                165                 170                 175
Arg Val Asp Asn Lys Asn Tyr Phe Pro Cys Arg Asp Gly Phe Gly Ser
                180                 185                 190
Ile Met Gln Met Ala Phe Cys Pro Glu Tyr Val Pro Thr Phe Asp Asn
                195                 200                 205
Val Ile Glu Asn Ile Thr Ser Leu Thr Ile Gly Lys Ser Lys Tyr Phe
210                 215                 220
Gln Asp Pro Ala Leu Leu Leu Met His Glu Leu Ile His Val Leu His
225                 230                 235                 240
Gly Leu Tyr Gly Met Gln Val Ser Ser His Glu Ile Ile Pro Ser Lys
                245                 250                 255
Gln Glu Ile Tyr Met Gln His Thr Tyr Pro Ile Ser Ala Glu Glu Leu
                260                 265                 270
Phe Thr Phe Gly Gly Gln Asp Ala Asn Leu Ile Ser Ile Asp Ile Lys
                275                 280                 285
Asn Asp Leu Tyr Glu Lys Thr Leu Asn Asp Tyr Lys Ala Ile Ala Asn
                290                 295                 300
Lys Leu Ser Gln Val Thr Ser Cys Asn Asp Pro Asn Ile Asp Ile Asp
305                 310                 315                 320
Ser Tyr Lys Gln Ile Tyr Gln Gln Lys Tyr Gln Phe Asp Lys Asp Ser
                325                 330                 335
Asn Gly Gln Tyr Ile Val Asn Glu Asp Lys Phe Gln Ile Leu Tyr Asn
                340                 345                 350
Ser Ile Met Tyr Gly Phe Thr Glu Ile Glu Leu Gly Lys Lys Phe Asn
                355                 360                 365
Ile Lys Thr Arg Leu Ser Tyr Phe Ser Met Asn His Asp Pro Val Lys
                370                 375                 380
Ile Pro Asn Leu Leu Asp Asp Thr Ile Tyr Asn Asp Thr Glu Gly Phe
385                 390                 395                 400
Asn Ile Glu Ser Lys Asp Leu Lys Ser Glu Tyr Lys Gly Gln Asn Met
                405                 410                 415
Arg Val Asn Thr Asn Ala Phe Arg Asn Val Asp Gly Ser Gly Leu Val
                420                 425                 430
Ser Lys Leu Ile Gly Leu Cys Lys Lys Ile Ile Pro Pro Thr Asn Ile
                435                 440                 445
Arg Glu Asn Leu Tyr Asn Arg Thr Ala Ser Leu Thr Asp Leu Gly Gly
450                 455                 460
Glu Leu Cys Ile Lys Ile Lys Asn Glu Asp Leu Thr Phe Ile Ala Glu
```

-continued

```
                465                 470                 475                 480
Lys Asn Ser Phe Ser Glu Glu Pro Phe Gln Asp Glu Ile Val Ser Tyr
                    485                 490                 495

Asn Thr Lys Asn Lys Pro Leu Asn Phe Asn Tyr Ser Leu Asp Lys Ile
                500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
        530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
                580                 585                 590

Tyr Ser Tyr Phe Pro Ser Val Ile Ser Lys Val Asn Gln Gly Ala Gln
            595                 600                 605

Gly Ile Leu Phe Leu Gln Trp Val Arg Asp Ile Ile Asp Asp Phe Thr
        610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
                660                 665                 670

Leu Leu Glu Tyr Ile Pro Glu Ile Thr Leu Pro Val Ile Ala Ala Leu
            675                 680                 685

Ser Ile Ala Glu Ser Ser Thr Gln Lys Glu Lys Ile Ile Lys Thr Ile
        690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
                740                 745                 750

Lys Lys Ile Ile Asp Tyr Glu Tyr Lys Ile Tyr Ser Gly Pro Asp Lys
            755                 760                 765

Glu Gln Ile Ala Asp Glu Ile Asn Asn Leu Lys Asn Lys Leu Glu Glu
        770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
                820                 825                 830

Lys Ala Asn Ser Lys Phe Ile Gly Ile Thr Glu Leu Lys Lys Leu Glu
            835                 840                 845

Ser Lys Ile Asn Lys Val Phe Ser Thr Pro Ile Pro Phe Ser Tyr Ser
        850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895
```

-continued

Ser Asp Ile Ser Gly Phe Asn Ser Ser Val Ile Thr Tyr Pro Asp Ala
            900             905             910

Gln Leu Val Pro Gly Ile Asn Gly Lys Ala Ile His Leu Val Asn Asn
            915             920             925

Glu Ser Ser Glu Val Ile Val His Lys Ala Met Asp Ile Glu Tyr Asn
    930             935             940

Asp Met Phe Asn Asn Phe Thr Val Ser Phe Trp Leu Arg Val Pro Lys
945             950             955             960

Val Ser Ala Ser His Leu Glu Gln Tyr Gly Thr Asn Glu Tyr Ser Ile
            965             970             975

Ile Ser Ser Met Lys Lys His Ser Leu Ser Ile Gly Ser Gly Trp Ser
            980             985             990

Val Ser Leu Lys Gly Asn Asn Leu Ile Trp Thr Leu Lys Asp Ser Ala
            995             1000            1005

Gly Glu Val Arg Gln Ile Thr Phe Arg Asp Leu Pro Asp Lys Phe
    1010            1015            1020

Asn Ala Tyr Leu Ala Asn Lys Trp Val Phe Ile Thr Ile Thr Asn
    1025            1030            1035

Asp Arg Leu Ser Ser Ala Asn Leu Tyr Ile Asn Gly Val Leu Met
    1040            1045            1050

Gly Ser Ala Glu Ile Thr Gly Leu Gly Ala Ile Arg Glu Asp Asn
    1055            1060            1065

Asn Ile Thr Leu Lys Leu Asp Arg Cys Asn Asn Asn Gln Tyr
    1070            1075            1080

Val Ser Ile Asp Lys Phe Arg Ile Phe Cys Lys Ala Leu Asn Pro
    1085            1090            1095

Lys Glu Ile Glu Lys Leu Tyr Thr Ser Tyr Leu Ser Ile Thr Phe
    1100            1105            1110

Leu Arg Asp Phe Trp Gly Asn Pro Leu Arg Tyr Asp Thr Glu Tyr
    1115            1120            1125

Tyr Leu Ile Pro Val Ala Ser Ser Ser Lys Asp Val Gln Leu Lys
    1130            1135            1140

Asn Ile Thr Asp Tyr Met Tyr Leu Thr Asn Ala Pro Ser Tyr Thr
    1145            1150            1155

Asn Gly Lys Leu Asn Ile Tyr Tyr Arg Arg Leu Tyr Asn Gly Leu
    1160            1165            1170

Lys Phe Ile Ile Lys Arg Tyr Thr Pro Asn Asn Glu Ile Asp Ser
    1175            1180            1185

Phe Val Lys Ser Gly Asp Phe Ile Lys Leu Tyr Val Ser Tyr Asn
    1190            1195            1200

Asn Asn Glu His Ile Val Gly Tyr Pro Lys Asp Gly Asn Ala Phe
    1205            1210            1215

Asn Asn Leu Asp Arg Ile Leu Arg Val Gly Tyr Asn Ala Pro Gly
    1220            1225            1230

Ile Pro Leu Tyr Lys Lys Met Glu Ala Val Lys Leu Arg Asp Leu
    1235            1240            1245

Lys Thr Tyr Ser Val Gln Leu Lys Leu Tyr Asp Asp Lys Asn Ala
    1250            1255            1260

Ser Leu Gly Leu Val Gly Thr His Asn Gly Gln Ile Gly Asn Asp
    1265            1270            1275

Pro Asn Arg Asp Ile Leu Ile Ala Ser Asn Trp Tyr Phe Asn His
    1280            1285            1290

```
Leu Lys Asp Lys Ile Leu Gly Cys Asp Trp Tyr Phe Val Pro Thr
    1295                1300                1305

Asp Glu Gly Trp Thr Asn Asp
    1310            1315

<210> SEQ ID NO 17
<211> LENGTH: 9
<212> TYPE: PRT
<213> ORGANISM: Artificial Sequence
<220> FEATURE:
<223> OTHER INFORMATION: peptide used for immunization

<400> SEQUENCE: 17

Cys Thr Arg Ile Asp Glu Ala Asn Gln
1               5

<210> SEQ ID NO 18
<211> LENGTH: 114
<212> TYPE: PRT
<213> ORGANISM: Mus musculus

<400> SEQUENCE: 18

Glu Val Asn Leu Val Glu Ser Gly Gly Asp Leu Val Lys Pro Gly Gly
1               5                   10                  15

Ser Leu Lys Leu Ser Cys Ala Val Ser Gly Phe Thr Phe Ser Gly Tyr
                20                  25                  30

Ala Met Ser Trp Val Arg Gln Thr Pro Glu Lys Arg Leu Glu Trp Val
            35                  40                  45

Ala Ser Ile Ala Thr Asn Gly Ser Thr Tyr Tyr Pro Asp Thr Val Lys
        50                  55                  60

Gly Arg Phe Thr Ile Phe Arg Asp Asn Ala Arg Asn Ile Leu Tyr Leu
65                  70                  75                  80

Gln Met Ser Ser Leu Arg Ser Glu Asp Thr Ala Ile Tyr Tyr Cys Thr
                85                  90                  95

Arg Leu Arg Gly Phe Asp Asn Trp Gly Gln Gly Thr Thr Leu Thr Val
            100                 105                 110

Ser Ser

<210> SEQ ID NO 19
<211> LENGTH: 112
<212> TYPE: PRT
<213> ORGANISM: Mus musculus

<400> SEQUENCE: 19

Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Asn Ile Val His Ser
                20                  25                  30

Asn Gly Asn Thr Tyr Leu Glu Trp Tyr Leu Gln Lys Ser Gly Gln Ser
            35                  40                  45

Pro Lys Leu Leu Ile Tyr Lys Val Phe Lys Arg Leu Ser Gly Val Pro
        50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```

<210> SEQ ID NO 20
<211> LENGTH: 10
<212> TYPE: PRT
<213> ORGANISM: Mus musculus

<400> SEQUENCE: 20

Gly Phe Thr Phe Ser Gly Tyr Ala Met Ser
1               5                   10

<210> SEQ ID NO 21
<211> LENGTH: 16
<212> TYPE: PRT
<213> ORGANISM: Mus musculus

<400> SEQUENCE: 21

Ser Ile Ala Thr Asn Gly Ser Thr Tyr Tyr Pro Asp Thr Val Lys Gly
1               5                   10                  15

<210> SEQ ID NO 22
<211> LENGTH: 4
<212> TYPE: PRT
<213> ORGANISM: Mus musculus

<400> SEQUENCE: 22

Gly Phe Asp Asn
1

<210> SEQ ID NO 23
<211> LENGTH: 16
<212> TYPE: PRT
<213> ORGANISM: Mus musculus

<400> SEQUENCE: 23

Arg Ser Ser Gln Asn Ile Val His Ser Asn Gly Asn Thr Tyr Leu Glu
1               5                   10                  15

<210> SEQ ID NO 24
<211> LENGTH: 7
<212> TYPE: PRT
<213> ORGANISM: Mus musculus

<400> SEQUENCE: 24

Lys Val Phe Lys Arg Leu Ser
1               5

<210> SEQ ID NO 25
<211> LENGTH: 9
<212> TYPE: PRT
<213> ORGANISM: Mus musculus

<400> SEQUENCE: 25

Phe Gln Gly Ser His Val Pro Tyr Thr
1               5

<210> SEQ ID NO 26
<211> LENGTH: 119
<212> TYPE: PRT
<213> ORGANISM: Mus musculus

<400> SEQUENCE: 26

Asp Val Gln Leu Gln Glu Ser Gly Pro Gly Leu Val Lys Pro Ser Gln
1               5                   10                  15

Ser Leu Ser Leu Thr Cys Thr Val Thr Gly Phe Ser Ile Thr Ser Asp
            20                  25                  30

Tyr Ala Trp Asn Trp Ile Arg Gln Phe Pro Gly Asn Lys Leu Glu Trp
            35                  40                  45

Met Gly Tyr Ile Ser Tyr Lys Tyr Gly Thr Arg Tyr Asn Pro Ser Leu
        50                  55                  60

Lys Gly Arg Ile Ser Ile Thr Arg Asp Thr Ser Lys Asn Gln Phe Phe
65                  70                  75                  80

Leu Gln Leu Asn Ser Leu Thr Thr Glu Asp Thr Ala Ile Tyr Tyr Cys
                85                  90                  95

Ala Arg Arg Gly Thr Asp Gly Tyr Gly Phe Ala Tyr Trp Gly Gln Gly
            100                 105                 110

Thr Leu Val Thr Val Ser Ala
        115

<210> SEQ ID NO 27
<211> LENGTH: 111
<212> TYPE: PRT
<213> ORGANISM: Mus musculus

<400> SEQUENCE: 27

Asp Ile Val Leu Thr Gln Ser Pro Ala Ser Leu Gly Val Ser Leu Gly
1               5                   10                  15

Gln Arg Ala Thr Ile Ser Cys Arg Ala Ser Glu Ser Val Ser Ser Ser
            20                  25                  30

Gly Tyr Ser Tyr Ile His Trp Tyr Gln Gln Arg Pro Gly Gln Pro Pro
        35                  40                  45

Lys Leu Leu Ile Phe Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys
            100                 105                 110

<210> SEQ ID NO 28
<211> LENGTH: 11
<212> TYPE: PRT
<213> ORGANISM: Mus musculus

<400> SEQUENCE: 28

Gly Phe Ser Ile Thr Ser Asp Tyr Ala Trp Asn
1               5                   10

<210> SEQ ID NO 29
<211> LENGTH: 16
<212> TYPE: PRT
<213> ORGANISM: Mus musculus

<400> SEQUENCE: 29

Tyr Ile Ser Tyr Lys Tyr Gly Thr Arg Tyr Asn Pro Ser Leu Lys Gly
1               5                   10                  15

<210> SEQ ID NO 30
<211> LENGTH: 9
<212> TYPE: PRT
<213> ORGANISM: Mus musculus

<400> SEQUENCE: 30

Gly Thr Asp Gly Tyr Gly Phe Ala Tyr

<210> SEQ ID NO 31
<211> LENGTH: 15
<212> TYPE: PRT
<213> ORGANISM: Mus musculus

<400> SEQUENCE: 31

Arg Ala Ser Glu Ser Val Ser Ser Gly Tyr Ser Tyr Ile His
1               5                   10                  15

<210> SEQ ID NO 32
<211> LENGTH: 7
<212> TYPE: PRT
<213> ORGANISM: Mus musculus

<400> SEQUENCE: 32

Leu Ala Ser Asn Leu Glu Ser
1               5

<210> SEQ ID NO 33
<211> LENGTH: 9
<212> TYPE: PRT
<213> ORGANISM: Mus musculus

<400> SEQUENCE: 33

Gln His Ser Arg Glu Leu Pro Leu Thr
1               5

<210> SEQ ID NO 34
<211> LENGTH: 114
<212> TYPE: PRT
<213> ORGANISM: Mus musculus

<400> SEQUENCE: 34

Glu Val Lys Leu Val Glu Ser Gly Gly Asp Leu Val Lys Pro Gly Gly
1               5                   10                  15

Ser Leu Lys Leu Ser Cys Ala Val Ser Gly Phe Ser Leu Asn Thr Tyr
            20                  25                  30

Ala Met Ser Trp Val Arg Gln Thr Pro Glu Gln Arg Leu Glu Trp Val
        35                  40                  45

Ala Ser Ile Ser Thr Asn Gly Ser Thr Tyr His Ser Asp Ser Val Lys
    50                  55                  60

Gly Arg Phe Thr Ile Ser Arg Tyr Asn Ala Arg Asn Ile Leu Tyr Leu
65                  70                  75                  80

Gln Met Ser Ser Leu Arg Ser Glu Asp Ser Ala Ile Tyr Tyr Cys Thr
                85                  90                  95

Arg Leu Arg Gly Phe Asp Tyr Trp Gly Gln Gly Thr Thr Leu Thr Val
            100                 105                 110

Ser Ser

<210> SEQ ID NO 35
<211> LENGTH: 112
<212> TYPE: PRT
<213> ORGANISM: Mus musculus

<400> SEQUENCE: 35

Asp Ile Leu Met Thr Gln Thr Pro Leu Ser Leu Ser Val Ser Leu Gly
1               5                   10                  15

Asp Gln Ala Ser Ile Ser Cys Arg Ser Ser Gln Asn Ile Val His Ser
            20                  25                  30

```
Asn Gly Asn Thr Tyr Leu Glu Trp Tyr Leu Gln Lys Pro Gly Gln Ser
        35                  40                  45

Pro Lys Pro Leu Ile Tyr Lys Leu Ser Lys Arg Phe Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                100                 105                 110

<210> SEQ ID NO 36
<211> LENGTH: 10
<212> TYPE: PRT
<213> ORGANISM: Mus musculus

<400> SEQUENCE: 36

Gly Phe Ser Leu Asn Thr Tyr Ala Met Ser
1               5                   10

<210> SEQ ID NO 37
<211> LENGTH: 16
<212> TYPE: PRT
<213> ORGANISM: Mus musculus

<400> SEQUENCE: 37

Ser Ile Ser Thr Asn Gly Ser Thr Tyr His Ser Asp Ser Val Lys Gly
1               5                   10                  15

<210> SEQ ID NO 38
<211> LENGTH: 8
<212> TYPE: PRT
<213> ORGANISM: Mus musculus

<400> SEQUENCE: 38

Thr Arg Leu Arg Gly Phe Asp Tyr
1               5

<210> SEQ ID NO 39
<211> LENGTH: 16
<212> TYPE: PRT
<213> ORGANISM: Mus musculus

<400> SEQUENCE: 39

Arg Ser Ser Gln Asn Ile Val His Ser Asn Gly Asn Thr Tyr Leu Glu
1               5                   10                  15

<210> SEQ ID NO 40
<211> LENGTH: 7
<212> TYPE: PRT
<213> ORGANISM: Mus musculus

<400> SEQUENCE: 40

Lys Leu Ser Lys Arg Phe Ser
1               5

<210> SEQ ID NO 41
<211> LENGTH: 9
<212> TYPE: PRT
<213> ORGANISM: Mus musculus

<400> SEQUENCE: 41
```

```
Phe Gln Gly Ser His Val Pro Tyr Thr
1               5
```

<210> SEQ ID NO 42
<211> LENGTH: 114
<212> TYPE: PRT
<213> ORGANISM: Mus musculus

<400> SEQUENCE: 42

```
Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Asn Thr Tyr
            20                  25                  30

Ala Met Ser Trp Val Arg Gln Thr Pro Glu Lys Arg Leu Glu Trp Val
        35                  40                  45

Ala Ser Ile Ser Ser Asn Gly Ser Thr Tyr His Pro Glu Ser Val Lys
    50                  55                  60

Gly Arg Phe Thr Ile Ser Arg Asp Ile Ala Arg Asn Ile Leu Asn Leu
65                  70                  75                  80

Gln Met Ser Ser Leu Arg Ser Glu Asp Thr Ala Ile Tyr Tyr Cys Ser
                85                  90                  95

Arg Leu Arg Gly Phe Asp Tyr Trp Gly Gln Gly Thr Thr Leu Thr Val
            100                 105                 110

Ser Ser
```

<210> SEQ ID NO 43
<211> LENGTH: 112
<212> TYPE: PRT
<213> ORGANISM: Mus musculus

<400> SEQUENCE: 43

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Pro Leu Ile Tyr Lys Val Phe Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```

<210> SEQ ID NO 44
<211> LENGTH: 10
<212> TYPE: PRT
<213> ORGANISM: Mus musculus

<400> SEQUENCE: 44

```
Gly Phe Thr Phe Asn Thr Tyr Ala Met Ser
1               5                   10
```

<210> SEQ ID NO 45
<211> LENGTH: 16
<212> TYPE: PRT
<213> ORGANISM: Mus musculus

<400> SEQUENCE: 45

Ser Ile Ser Ser Asn Gly Ser Thr Tyr His Pro Glu Ser Val Lys Gly
1               5                   10                  15

<210> SEQ ID NO 46
<211> LENGTH: 8
<212> TYPE: PRT
<213> ORGANISM: Mus musculus

<400> SEQUENCE: 46

Ser Arg Leu Arg Gly Phe Asp Tyr
1               5

<210> SEQ ID NO 47
<211> LENGTH: 16
<212> TYPE: PRT
<213> ORGANISM: Mus musculus

<400> SEQUENCE: 47

Arg Ser Ser Gln Ser Ile Val His Ser Asn Gly Asn Thr Tyr Leu Glu
1               5                   10                  15

<210> SEQ ID NO 48
<211> LENGTH: 7
<212> TYPE: PRT
<213> ORGANISM: Mus musculus

<400> SEQUENCE: 48

Lys Val Phe Lys Arg Phe Ser
1               5

<210> SEQ ID NO 49
<211> LENGTH: 9
<212> TYPE: PRT
<213> ORGANISM: Mus musculus

<400> SEQUENCE: 49

Phe Gln Gly Ser His Val Pro Tyr Thr
1               5

<210> SEQ ID NO 50
<211> LENGTH: 114
<212> TYPE: PRT
<213> ORGANISM: Mus musculus

<400> SEQUENCE: 50

Glu Val Lys Leu Val Glu Phe Gly Gly Gly Leu Val Glu Pro Arg Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Glu Lys Arg Leu Glu Trp Val
        35                  40                  45

Ala Ser Ile Ala Ser Asn Gly Ser Thr Tyr Tyr Pro Asp Ser Val Arg
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ser
                85                  90                  95

Arg Leu Arg Gly Phe Asp Tyr Trp Gly Gln Gly Ser Thr Leu Thr Val
            100                 105                 110

Ser Ser

<210> SEQ ID NO 51
<211> LENGTH: 112
<212> TYPE: PRT
<213> ORGANISM: Mus musculus

<400> SEQUENCE: 51

Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Ser Leu Leu Ile Tyr Lys Val Phe Lys Arg Leu Ser Gly Val Pro
    50                  55                  60

Asp Arg Phe Ser Gly Ser Gly Ser Gly Thr Glu Phe Thr Leu Lys Ile
65                  70                  75                  80

Asn Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 52
<211> LENGTH: 10
<212> TYPE: PRT
<213> ORGANISM: Mus musculus

<400> SEQUENCE: 52

Gly Phe Thr Phe Ser Thr Tyr Ala Met Ser
1               5                   10

<210> SEQ ID NO 53
<211> LENGTH: 16
<212> TYPE: PRT
<213> ORGANISM: Mus musculus

<400> SEQUENCE: 53

Ser Ile Ala Ser Asn Gly Ser Thr Tyr Tyr Pro Asp Ser Val Arg Gly
1               5                   10                  15

<210> SEQ ID NO 54
<211> LENGTH: 8
<212> TYPE: PRT
<213> ORGANISM: Mus musculus

<400> SEQUENCE: 54

Ser Arg Leu Arg Gly Phe Asp Tyr
1               5

<210> SEQ ID NO 55
<211> LENGTH: 16
<212> TYPE: PRT
<213> ORGANISM: Mus musculus

<400> SEQUENCE: 55

Arg Ser Ser Gln Ser Ile Val His Ser Asn Gly Asn Thr Tyr Leu Glu
1               5                   10                  15

<210> SEQ ID NO 56
<211> LENGTH: 7
<212> TYPE: PRT

<213> ORGANISM: Mus musculus

<400> SEQUENCE: 56

Lys Val Phe Lys Arg Leu Ser
1               5

<210> SEQ ID NO 57
<211> LENGTH: 9
<212> TYPE: PRT
<213> ORGANISM: Mus musculus

<400> SEQUENCE: 57

Phe Gln Gly Ser His Val Pro Tyr Thr
1               5

<210> SEQ ID NO 58
<211> LENGTH: 114
<212> TYPE: PRT
<213> ORGANISM: Mus musculus

<400> SEQUENCE: 58

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Arg Ser Tyr
            20                  25                  30

Ala Val Ser Trp Val Arg Gln Thr Pro Glu Lys Arg Leu Glu Trp Val
        35                  40                  45

Ala Ser Ile Ser Thr Asn Gly Ser Thr Tyr Tyr Pro Asp Ser Met Lys
    50                  55                  60

Gly Arg Phe Thr Ile Ser Arg Asp Thr Ala Arg Asn Ile Leu Tyr Leu
65                  70                  75                  80

Glu Met Asn Ser Leu Arg Ser Glu Asp Thr Ala Met Tyr Tyr Cys Ala
                85                  90                  95

Arg Leu Arg Gly Phe Asp Tyr Trp Gly Gln Gly Thr Pro Leu Thr Val
            100                 105                 110

Ser Ser

<210> SEQ ID NO 59
<211> LENGTH: 112
<212> TYPE: PRT
<213> ORGANISM: Mus musculus

<400> SEQUENCE: 59

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

```
<210> SEQ ID NO 60
<211> LENGTH: 10
<212> TYPE: PRT
<213> ORGANISM: Mus musculus

<400> SEQUENCE: 60

Gly Phe Thr Phe Arg Ser Tyr Ala Val Ser
1               5                   10

<210> SEQ ID NO 61
<211> LENGTH: 16
<212> TYPE: PRT
<213> ORGANISM: Mus musculus

<400> SEQUENCE: 61

Ser Ile Ser Thr Asn Gly Ser Thr Tyr Tyr Pro Asp Ser Met Lys Gly
1               5                   10                  15

<210> SEQ ID NO 62
<211> LENGTH: 7
<212> TYPE: PRT
<213> ORGANISM: Mus musculus

<400> SEQUENCE: 62

Arg Leu Arg Gly Phe Asp Tyr
1               5

<210> SEQ ID NO 63
<211> LENGTH: 16
<212> TYPE: PRT
<213> ORGANISM: Mus musculus

<400> SEQUENCE: 63

Arg Ser Ser Gln Ser Ile Val His Ser Asn Gly Asn Thr Tyr Leu Glu
1               5                   10                  15

<210> SEQ ID NO 64
<211> LENGTH: 7
<212> TYPE: PRT
<213> ORGANISM: Mus musculus

<400> SEQUENCE: 64

Lys Val Ser Lys Arg Phe Ser
1               5

<210> SEQ ID NO 65
<211> LENGTH: 9
<212> TYPE: PRT
<213> ORGANISM: Mus musculus

<400> SEQUENCE: 65

Phe Gln Gly Ser His Val Pro Tyr Thr
1               5

<210> SEQ ID NO 66
<211> LENGTH: 114
<212> TYPE: PRT
<213> ORGANISM: Mus musculus

<400> SEQUENCE: 66

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Leu Ser Asp Tyr
            20                  25                  30
```

```
Ala Met Ser Trp Val Arg Gln Ser Pro Glu Glu Arg Leu Glu Trp Val
             35                  40                  45

Ala Ser Ile Ser Thr Asn Gly Ser Thr Tyr Tyr Pro Asp Ser Val Lys
 50                      55                  60

Gly Arg Phe Thr Ile Ser Arg Asp Asn Ala Arg Asn Ile Leu Ser Leu
 65                  70                  75                  80

Gln Met Ser Ser Leu Arg Ser Glu Asp Thr Ala Ile Tyr Tyr Cys Thr
                 85                  90                  95

Arg Leu Arg Gly Phe Asp Asn Trp Gly Gln Gly Thr Leu Leu Thr Val
            100                 105                 110

Ser Ser

<210> SEQ ID NO 67
<211> LENGTH: 112
<212> TYPE: PRT
<213> ORGANISM: Mus musculus

<400> SEQUENCE: 67

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Asn Ile Val His Ser
             20                  25                  30

Asn Gly Asn Thr Tyr Leu Glu Trp Tyr Leu Gln Lys Ser Gly Gln Ser
         35                  40                  45

Pro Lys Leu Leu Met Tyr Lys Val Ser Lys Arg Leu Ser Gly Val Pro
     50                  55                  60

Asp Arg Phe Ser Gly Arg Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Tyr Thr Phe Gly Gly Gly Thr Lys Leu Glu Ile Lys
            100                 105                 110

<210> SEQ ID NO 68
<211> LENGTH: 10
<212> TYPE: PRT
<213> ORGANISM: Mus musculus

<400> SEQUENCE: 68

Gly Phe Thr Leu Ser Asp Tyr Ala Met Ser
 1               5                  10

<210> SEQ ID NO 69
<211> LENGTH: 16
<212> TYPE: PRT
<213> ORGANISM: Mus musculus

<400> SEQUENCE: 69

Ser Ile Ser Thr Asn Gly Ser Thr Tyr Tyr Pro Asp Ser Val Lys Gly
 1               5                  10                  15

<210> SEQ ID NO 70
<211> LENGTH: 8
<212> TYPE: PRT
<213> ORGANISM: Mus musculus

<400> SEQUENCE: 70

Thr Arg Leu Arg Gly Phe Asp Asn
 1               5
```

```
<210> SEQ ID NO 71
<211> LENGTH: 16
<212> TYPE: PRT
<213> ORGANISM: Mus musculus

<400> SEQUENCE: 71

Arg Ser Ser Gln Asn Ile Val His Ser Asn Gly Asn Thr Tyr Leu Glu
1               5                   10                  15

<210> SEQ ID NO 72
<211> LENGTH: 7
<212> TYPE: PRT
<213> ORGANISM: Mus musculus

<400> SEQUENCE: 72

Lys Val Ser Lys Arg Leu Ser
1               5

<210> SEQ ID NO 73
<211> LENGTH: 9
<212> TYPE: PRT
<213> ORGANISM: Mus musculus

<400> SEQUENCE: 73

Phe Gln Gly Ser His Val Pro Tyr Thr
1               5

<210> SEQ ID NO 74
<211> LENGTH: 8
<212> TYPE: PRT
<213> ORGANISM: Mus musculus

<400> SEQUENCE: 74

Thr Arg Ile Asp Glu Ala Asn Gln
1               5

<210> SEQ ID NO 75
<211> LENGTH: 7
<212> TYPE: PRT
<213> ORGANISM: Mus musculus

<400> SEQUENCE: 75

Arg Ile Asp Glu Ala Asn Gln
1               5

<210> SEQ ID NO 76
<211> LENGTH: 6
<212> TYPE: PRT
<213> ORGANISM: Mus musculus

<400> SEQUENCE: 76

Ile Asp Glu Ala Asn Gln
1               5

<210> SEQ ID NO 77
<211> LENGTH: 5
<212> TYPE: PRT
<213> ORGANISM: Mus musculus

<400> SEQUENCE: 77

Asp Glu Ala Asn Gln
1               5
```